(12) United States Patent
Guerry et al.

(10) Patent No.: US 10,500,261 B2
(45) Date of Patent: *Dec. 10, 2019

(54) SYNTHETIC ANTIGEN CONSTRUCTS AGAINST CAMPYLOBACTER JEJUNI

(71) Applicant: **United

(56) References Cited

U.S. PATENT DOCUMENTS

| | | |
|---|---|---|
| 2010/0297141 A1 | 11/2010 | Savarino |
| 2011/0097357 A1 | 4/2011 | Fernandez et al. |
| 2011/0189236 A1 | 8/2011 | Scott et al. |
| 2011/0274720 A1 | 11/2011 | Wacker et al. |
| 2011/0300173 A1 | 12/2011 | Guerry et al. |
| 2012/0321658 A1 | 12/2012 | Biemans et al. |
| 2014/0141032 A1 | 5/2014 | Guerry et al. |
| 2015/0258201 A1 | 9/2015 | Guerry et al. |
| 2015/0273037 A1 | 10/2015 | Guerry et al. |

FOREIGN PATENT DOCUMENTS

| | | |
|---|---|---|
| WO | 2007/038122 A2 | 4/2007 |
| WO | 2007/148229 A1 | 12/2007 |
| WO | 2009/017666 A1 | 2/2009 |
| WO | 2014/077977 A1 | 5/2014 |
| WO | 2016/073773 A1 | 5/2016 |

OTHER PUBLICATIONS

Corcoran, et al., The Structure of the Lipid Anchor of Campylobacter Jejuni Polysaccharide, FEMS Microbial Let, vol. 257 (2006), 228-235.

Yun, et al., Synthesis of 2'-Azidoethyl Trisaccharide, α-D-Gal-(1→2)-6d-α-D-Altro-Hepp-(1→3)-β-D-GlcNAc, an O-Antigenic Repeating Unit of C. jejuni O:23 and O:36, Arch Pharm Res vol. 27, No. 2, 143-150, 2004.

Penner, et al., Diversity of Lipopolysaccharide Structures in Campylobacter Jejuni, The Journal of Infectious Diseases, 1997; 176(Suppl 2):S135-8.

Ophardt, Virtual Chembook Elmhurst College, 2009, Carbohydrates-Glucose, http://www.elmhurst.edu/~chm/vchembook/543galactose.html Sep. 9, 2008 3:34:55 PM.

Jennings, et al., Immunochemistry of groups A, B, and C memingococcal polysaccharide-tetanus toxoid conjugates, The Journal of Immunology (1981), vol. 127 p. 1011-1018.

Van Alphen, et al, Biological Roles of the O-Methyl Phosphoramidate Capsule Modification in Campylobacter Jejuni, Plos One, published Jan. 30, 2014, vol. 9, Issue 1, e87051, DOI: 10.1371/journal.pone.0087051.

Aspinall, et al., Structures of the O chains from the Lipopolysaccharides of Campylobacter jejuni Serotypes O:23 and O:36, Carbohydrate Research (1992), vol. 231, pp. 13-30.

Kanipes et al, Mutation of waaC Encoding Heptosyltransferase I in Campylobacter jejuni 81-176, Affects the Structure of both Lipooligosaccharide and Capsular Carbohydrate, The Journal of Bacteriology, May 2006, vol. 188, p. 3273-3279.

Karlyshev et al, Analysis of Campylobacter jejuni Capsular Loci Reveals Multiple Mechanisms for the Generation of Structural Diversity and the Ability to Form Complex Heptoses, Molecular Microbiology, Jan. 2005, vol. 55, No. 1, pp. 90-103.

Ritter et al, Induction of antibodies reactive with GM2 ganglioside after immunization with lipopolysaccharides from Camplobacter jejuni, Int. J. Cancer, 1996, vol. 66, pp. 184-190.

Papp-Szabo et al, Cell-Surface a-glucan in Campylobacter jejuni 81-176, Carbohydrate Research vol. 340, Issue 13, pp. 2218-2221, Sep. 26, 2005.

Jiao Y., et al, Synthesis and immunodetection of 6-O-methyl-phosphoramidyl-alpha-D-galactose: a Campylobacter jejuni antigenic determinant, Carbohydrate Research (2015), vol. 418, p. 9-12.

Gaasbeek, et al., Functional Characterization of Excision Repair and RecA-Dependent Recombinantional DNA Repair in Campylobacter Jejuni, Journal of Bacteriology (2009), vol. 191, No. 12, p. 3785-3793.

Aspinall, et al., Lipopolysaccharides of Campylobacter jejuni Serotype O:19: Structures of Core Oligosaccharide Regions from the Serostrain and Two Bacterial Isolates from Patients with the Guillain-Barre Syndrome, (1994) Biochemistry, vol. 33, pp. 241-249.

Aspinall, et al, Chemical structure of the core region of Campylobacter jejuni serotype O:2 lipopolysaccharide, European Journal of Biochemistry (1993), vol. 213, p. 1029-1037.

Aspinall, et al, Chemical structures of the core region of Campylobacter jejuni O:3 lipopolysaccharide and an associated polysaccharide, European Journal of Biochemistry (1995), vol. 231, p. 570-578.

St. Michael, et al, The Structures of the lipooligosaccharide and capsule polysaccharide of Campylobacter jejuni genome sequenced strain NCTC 11168, (2002) European Journal of Biochemistry, vol. 269, pp. 5119-5136.

McNally, et al, The HS:1 serostrain of Campylobacter jejuni has a complex teichoic acid-like capsular polysaccharide with nonstoichiometric fructofuranose branches and O-methyl phosphoramidate groups, FEBS Journal (2005), vol. 272, pp. 4407-4422.

Muldoon, et al, Structures of two polysaccharides of Campylobacter jejuni 81116, Carbohydrate Research (2002), vol. 337, p. 2223-2229.

Hannify, et al, Chemical structure of a polysaccharide from Campylobacter jejuni 176.83 (serotype O:41), containing only furanose sugars, (1999) Carbohydrate Research, vol. 319, pp. 124-132.

Baqar, et al, Safety and immunogenicity of a prototype oral whole-cell killed Campylobacter vaccine administered with a mucosal adjuvant in non-human primates, Vaccine, 2005, vol. 13, No. 1, pp. 22-28.

Roberts, The biochemistry and genetics of capsular polysaccharide production in bacteria, Annual Review of Microbiology, 1996, vol. 50, pp. 285-315.

Maue, et al, The Polysaccharide Capsule of Campylobacter jejuni Modulates the Host Immune Response, Infection and Immunity, Mar. 2013, vol. 831, No. 3, pp. 665-672.

McNally, et al, The HS:19 serostrain of Campylobacter jejuni has a hyaluronic acid-type capsular polysaccharide with a nonstoichiometric sorbose brance and O-methyl phosphoramidate group, The FEBS Journal, vol. 273 (2006), pp. 3975-3989.

Guerry, Ilir Project Title Capsule Vaccines against Campylobacter jejuni, Independent Research Annual Report, attached email dated May 29, 2008.

McNally, et al, Commonality and Biosynthesis of the O-Methyl Phosphoramidate Capsule Modification in Campylobacter jejuni, Journal of Biological Chemistry, vol. 282, No. 39, pp. 28566-28576, published Sep. 28, 2007.

Szmanski, et al, Detection of Conserved N-Linked Gycans and Phase-variable Lipooligosaccharides and Capsules from Campylobacter Cells by Mass Spectrometry and High Resolution Magic Angle Spinning NMR Spectroscopy, The Journal of Biological Chemistry, vol. 278, No. 27, Issue of Jul. 4., pp. 24509-24520, 2003.

Chen, et al., The chemical structure and genetic locus of Campylobacter jejuni CG8486 (serotype HS:4) capsular polysaccharide: the identification of 6-deoxy-D-ido-heptopyranose, Carbohydrate Research, 2008, vol. 343, pp. 1034-1040.

Guerry, et al, Campylobacter polysaccharide capsules: virulence and vaccines, Frontiers in Cellular and Infection Microbiology, Feb. 2012, vol. 2, Article 7, p. 1-11. doi: 10.3389/fcimb.2012.00007.

International Search Report for Application No. PCT/US2015/059315, dated Feb. 8, 2016.

International Search Report for Application No. PCT/US2006/036619, dated Jun. 15, 2007.

Comfort, et al., Biochemical analysis of Thermotoga maritima GH36 alpha-galactosidase (TmGalA) confirms the mechanistic commonality of clan GH-D glycoside hydrolases, Biochemistry (2007), vol. 46, Iss. 11, p. 3319-3330.

Alving, et al., Lipid A and liposomes containing lipid A as antigens and adjuvants, Vaccine (2008), vol. 26, Iss. 24, p. 3036-3045, doi:10.1016/j.vaccine.2007.12.002.

Alving, et al., Adjuvants for human vaccines, Current Opinion in Immunology (2012), vol. 24, Iss. 3, p. 310-315.

Alving, et al., Liposomes containing lipid A: an effective, safe, generic adjuvant system for synthetic vaccines, Expert Rev. Vaccines (2012), vol. 11, No. 6, p. 733-744, doi: 10.1586/erv.12.35.

(56) References Cited

OTHER PUBLICATIONS

Aspinall, et al., Lipopolysaccharides from Campylobacter Jejuni Associated with Guillain-Barre Syndrome Patients Mimic Human Gangliosides in Structure, Infection and Immunity (1994), vol. 62, No. 5, p. 2122-2125.

Bachtiar,et al., Knockout mutagenesis of the kpsE gene of Campylobacter jejuni 81116 and its involvement in bacterium-host interactions, FEMS Immunology and Medical Microbiology (2007), vol. 49, p. 149-154, DOI: http://dx.doi.org/10.1111/j.1574-695X.2006.00182.x.

Bacon et al., A phase-variable capsule is involved in virulence of Campylobacter jejuni 81-176, Molecular Microbiology (2001), vol. 40, No. 3, p. 769-777, DOI: 10.1046/j.1365-2958.2001.02431.x.

Bash, et al., Development and use of a serum bactericidal assay using pooled human complement to assess responses to a meningococcal group A conjugate vaccine in African toddlers, Clinical and Vaccine Immunology (2014), vol. 21, No. 5, p. 755-761.

Bertolo, et al., The design of a capsule polysaccharide conjugate vaccine against Campylobacter jejuni serotype HS15, Carbohydrate Research (2013), vol. 366, p. 45-49.

Blaser, et al., Susceptibility of campylobacter isolates to the bactericidal activity of human-serum, Journal of Infectious Diseases (1985), vol. 151, Iss. 2, p. 227-235.

Cameron, et al, Hyperosmotic stress response of Campylobacter jejuni, Journal of Bacteriology (2012), vol. 194, Iss. 22, p. 6116-6130.

Cameron, et al, High-Frequency Variation of Purine Biosynthesis Genes is a Mechanism of Success in Campylobacter jejuni, mBio (2015), vol. 6, Iss. 5, p. e00612-e00615. Doi:I0.1128/mBio.00612-15.

Champion, et al, Insect infection model for campylobacter jejuni reveals that O-methyl phosphoramidate has insecticidal activity, The Journal of Infectious Diseases (2010), vol. 201, p. 776-782.

Coker, et al., Human Campylobacteriosis in Developing Countries, Emerging Infectious Diseases Journal (2002), vol. 8, p. 237-243.

Epps, et al., Foodborne Campylobacter, Infections, Metabolism, Pathogenesis and Reservoirs, International Journal of Environmental Research and Public Health (2013), vol. 10, p. 6292-6304.

Ewing, et al., Functional Characterization of Flagellin Glycosylation in Campylobacter jejuni 81-176, Journal of Bacteriology (2009), vol. 191, No. 22, p. 7086-7093.

Fattom, et al., Antigenic Determinants of *Staphylococcus aureus* Type 5 and Type 8 Capsular Polysaccharide Vaccines, Infection and Immunity (1998), vol. 66, No. 10, p. 4588-4592.

Gill, et al., Correlation between serum bactericidal activity against Neisseria meningitidis serogroups A, C, W-135 and Y measured using human versus rabbit serum as the complement source, Vaccine (2011), vol. 30, No. 1, p. 29-34.

Grant, et al., Signature-tagged transposon mutagenesis studies demonstrate the dynamic nature of cecal colonization of 2-week-old chickens by Campylobacter jejuni, Applied and Environmental Microbiology (2005), vol. 71, No. 12, p. 8031-8041.

Guerry, et al., Phase Variation of Campylobacter jejuni 81-176 Lipooligosaccharide Affects Ganglioside Mimicry and Invasiveness In Vitro, Infection and Immunity (2002), vol. 70, No. 2, p. 787-793.

Hendrixson, A phase-variable mechanism controlling the Campylobacter jejuni FlgR response regulator influences commensalism, Molecular Microbiology (2006), vol. 61, No. 6, p. 1646-1659.

Karlyshev, et al., Genetic and biochemical evidence of a Campylobacter jejuni capsular polysaccharide that accounts for Penner serotype specificity, Molecular Microbiology (2000), vol. 35, No. 3p. 529-541.

King, et al., Going for baroque at the *Escherichia coli* K1 cell surface, Trends in Microbiology (2007), vol. 15, Iss. 5, p. 196-202.

Kotloff, et al., Burden and aetiology of diarrhoeal disease in infants and young children in developing countries (the Global Enteric Multicenter Study, GEMS): a prospective, case-control study,The Lancet (2013), vol. 382, Iss. 9888, p. 209-222, doi: 10.1016/S0140-6736(13)60844-2.

Knuf, et al., Comparative effects of carrier proteins on vaccine-induced immune response, Vaccine (2011), vol. 29, Iss. 31, p. 4881-4890, doi: 10.1016/j.vaccine.2011.04.053.

Lee, et al., Symptomatic and asymptomatic campylobacter infections associated with reduced growth in peruvian children, PLOS Neglected Tropical Diseases (2013), vol. 7, Iss. 1, p. e2036, Doi:10.1371/journal.pntd.002036.

Lesinski, et al., Vaccines Against Polysaccharide Antigens, Current Drug Targets—Infectious Disorders (2001), vol. 1, No. 3, p. 325-334.

Linton, et al., Phase variation of a b-1,3 galactosyltransferase involved in generation of the ganglioside GM1 lipo-oligosaccharide of Campylobacter jejuni, Molecular Microbiology (2000), vol. 37, Iss. 3, p. 501-514.

Mara, et al., Synthesis and evaluation of phosphoramidate and phosphorothioamidate analogues of amiprophos methyl as potential amtimalarial agents, Bioorganic and Medical Chemistry Letters (2011), vol. 21, Iss. 20., p. 6180-6183, doi:10.1016/j.bmcl.2011.07.088.

Mohawk, et al., High Frequency, Spontaneous motA Mutations in Campylobacter jejuni Strain 81-176, Plos One (2014), vol. 9, p. e88043, doi:10.1371/journallpone.008043.

Molbak, et al., Burden of illness of Campylobacteriosis and sequelae. Editors: I. Nachamkin, C. Szymanski & M. J. Blaser (ed.), 2008. Campylobacter, third edition, p. 151-162. (American Society for Microbiology, Washington, D.C.), ISBN 978-1-55581-437-3, Record No. 20083230309.

Anantha, et al, Evolutionary and functional relationships of colonization factor antigen I and other class 5 adhesive fimbriae of enterotoxigenic *Escherichia coli*, Infection and Immunity (2004), vol. 72, No. 12, p. 7190-7201.

Montgomery, et al., The preparation and rearrangement of phenylglycosides, Journal of the American Chemical Society (1942), vol. 64, No. 3, p. 690-694.

Moran, et al., Serotyping of Campylobacter jejuni based on heat stable antigens: relevance, molecular basis and implications in pathogenesis, Journal of Applied Microbiology (1999), vol. 86, Iss. 3, p. 361-377.

Moran, et al., Molecular mimicry of host structures by lipopolysaccharides of campylobacter and *helicobacter* spp.: implications in pathogenesis, Journal of Endotoxin Research (1996), vol. 3, No. 6, p. 521-531.

Morefield, et al, A Rational, Systematic Approach for the Development of Vaccine Formulations, The APPS Journal (2011), vol. 13, No. 2, p. 191-200.

Nachamkin, I et al., Campylobacter jejuni infection and the association with Guillain-Barre syndrome, p. 155-175, In I. Nachamkin and M. J. Blaser (ed.), Campylobacter, 2nd ed. (2000), ASM Press, Washington, DC.

Nyame, et al., Immunity to schistosomiasis: glycans are potential antigenic targets for immune intervention, Experimental Parasitoogy (2003), vol. 104, p. 1-13.

Oberhelman, et al., Campylobacter infections in developing countries (2000), pp. 139-154, I Nachamkin and M.J. Blaser, Campylobacter, 2nd ed., ASM Press, Washington, DC.

Parkhill, et al., Tthe genome sequence of the food-borne pathogen Campylobacter jejuni reveals hypervariable sequences, In Nature (2000), vol. 403, p. 665-668.

Penner, et al., Passive hemagglutination technique for serotyping *Campylobacter fetus* subsp. jejuni on the basis of soluble heat-stable antigens, Journal of Clinical Microbiology (1980), vol. 12, No. 6, p. 732-737.

Pennie, et al., Susceptibility of Campylobacter jejuni to strain-specific bactericidal activity in sera of infected patients, Infection and Immunity (1986), vol. 52, p. 702-706.

Platts-Mills, et al., Pathogen-specific burdens of community diarrhoea in developing countries: a multisite birth cohort study (MAL-ED), Lancet Glob Health (2015), vol. 3, No. 9, p. e564-575, Doi: 10.1016/S2214-109X (15) 00151-5.

Jordi, et al, Differential decay of RNA of the CFA/I fimbrial operon and control of relative gene expression, Journal of Bacteriology (1993), vol. 175, No. 24, p. 7976-7981.

(56) References Cited

OTHER PUBLICATIONS

Rose, et al., The Campylobacter jejuni NCTC11168 capsule prevents excessive cytokine production by dendritic cells, Medical Microbiology and Immunology (2012), vol. 201, p. 137-144.
Salloway, et al., Miller-Fisher syndrome associated with campylobacter jejuni bearing lipopolysaccharide molecules that mimic human ganglioside GD3, Infection and Immunity (1996), vol. 64, No. 8, p. 2945-2949.
Sorensen, et al., Bacteriophage F336 recognizes the capsular phosphoramidate modification of campylobacter jejuni NCTC 11168 #, Journal of Bacteriology (2011), vol. 193, Iss. 23, p. 6742-6749.
Sorensen, et al., Phase variable expression of capsular polysaccharide modifications allows campylobacter jejuni to avoid bacteriophage infection in chickens, Fronteirs in Cellular and Infection Microbiology (2012), vol. 2, Art. 11, p. 1-11. Doi: 10.3389/fcimb.2012.00011.
Stahl, et al., A novel mouse model of campylobacter jejuni gastroenteritis reveals key pro-inflammatory and tissue protective roles for toll-like receptor signaling during infection, Plos Pathogens (2014), vol. 10, No. 7, e1004264, Doi: 10.1371/journal.ppat.1004264.
Szu, et al., Relation between structure and immunologic properties of the Vi capsular polysaccharide, Infection and Immunity (1991), vol. 59, No. 12, p. 4555-4561.
Thomas, et al., Comparative variation within the genome of campylobacter jejuni NCTC 11168 in human and murine hosts, Plos One (2014), vol. 9, Iss. 2, e88229, Doi:10.1371/journal.pone.0088229.
Townsend, et al., Evaluation and validation of a serum bactericidal antibody assay for Haemophilus influenzae type b and the threshold of protection, Vaccine (2014), vol. 32, Iss. 43, p. 5650-5656.
Yao, et al., Molecular cloning and site-specific mutagenesis of a gene involved in arylsulfatase production in campylobacter jejuni, Journal of Bacteriology (1996), vol. 178, No. 11, p. 3335-3338.
Yao, et al., Construction of new campylobacter cloning vectors and a new mutational cat cassette, Gene (1993), vol. 130, Iss. 1, p. 127-130.
Calix, et al., Elucidation of Structural and Antigenic Properties of Pneumococcal Serotype 11A, 11B, 11C, and 11F Polysaccharide Capsules, Journal of Bacteriology, (2011), vol. 193, No. 19, p. 5271-5278.
Maue, et al, A capsule conjugate vaccine approach to prevent diarrheal disease caused by campylobacter jejuni, Human Vaccines Immunotherapeutics (2014), Col. 10, No. 6, p. 1499-1504.
Boylan, et al, Nucleotide sequence of the gene encoding the major subunit of CS3 fimbriae of entertoxigenic *Escherichia coli*, Infection and Immunity (1988), vol. 56, No. 12, p. 3297-3300.
Roy, et al, Crystal structure of enterotoxigenic *Escherichia coli* colonization factor CS6 reveals a novel type of functional assembly, Molecular Microbiology (2012), DOI: 10.1111/mmi.12044.
Rasko, et al, UniProtKB/TrEMBL Accession No. B3HIR3_ECOLX, Sep. 2, 2008 [online].
Rasko, et al, GenBankAccession No. CP000795, *Escherichia coil* E24377A plasmid pETEC_80, complete sequence, Aug. 13, 2007 [online].
Sakellaris, et al, A conserved residue in the tip proteins of CS1 and CFA/I pili of enterotoxigenic *Escherichia coli* that is essential for adherence, PNAS (1999), vol. 96, No. 22, p. 12828-12832.
Soto, et al, Bacterial adhesions: Common themes and variations in architecture and assembly, Journal of Bacteriology (1999), vol. 181, No. 4, p. 1059-1071.
Yu, et al, Assembly of cholera toxin-antigen fusion proteins in transgenic potato, Transgenics (2001), vol. 3 (2-4), p. 153-162.
Lee, et al, Plant-synthesized *E. coli* CFA/I fimbrial protein protects Caco-2 cells from bacterial attachment, Vaccine (2004), vol. 23, p. 222-231.
Allos, Association between Campylobacter Infection and Guillain-Barre Syndrome, The Journal of Infectious Diseases, 1997:176(Suppl 2):S125-128.
Jerome, et al, Standing genetic variation in contingency loci drives the rapid adaptation of campylobacter jejuni to a novel host, PLoS ONE, Jan. 2011, vol. 6, Iss 1, e16399.
International Preliminary Report on Patentability for Application No. PCT/2015/059315, dated May 18, 2017.
Supplementary European Search Report in EP15856653 dated Apr. 26, 2018.
Ashmus, R. et al., Organic Letters, vol. 16, No. 9, Apr. 16, 2014, pp. 2518-2521.
Poly, F. et al., J. Clinical Microbiology, vol. 49, No. 5, Mar. 16, 2011, pp. 1750-1757.
Redkyna, O., "A Vaccine against Campylobacter jejuni Serotype HS:5", Thesis presented to the University of Guelph (Canada) for Master of Science in Chemistry, Dec. 2013.
Pequegnat, B. et al., Journal of Bacteriology, vol. 199, Issue 14, Jul. 1, 2017, e00027-17.
Pequegnat, B., "Polysaccharide Vaccines for Enteric Pathogens: The Next Generation Multivalent Diarrhea Vaccine" Thesis presented to the University of Guelph (Canada) for degree of Philosophical Doctorate in Chemistry, May 2016.
International Search Report in PCT/US2016/060361 dated Jan. 9, 2017.
Written Opinion of the International Searching Authority in PCT/US2016/060361 dated Jan. 9, 2016.
Riazi et al., PLoS One, vol. 8, No. 12, pp. e83928, Dec. 31, 2013.
Tsubokura et al., Clin. Exp. Immunol. vol. 106, pp. 451-455, Jun. 1, 1997.

\* cited by examiner

Figure 1
Serotype
HS1
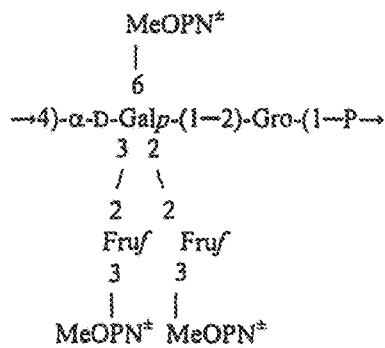
HS4
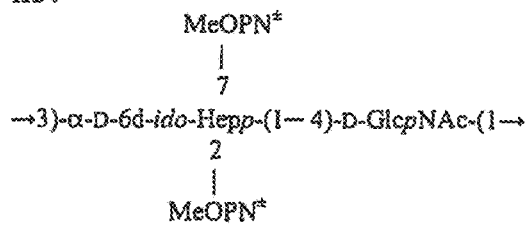
HS3
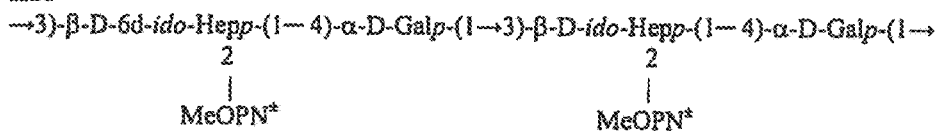
HS23/36
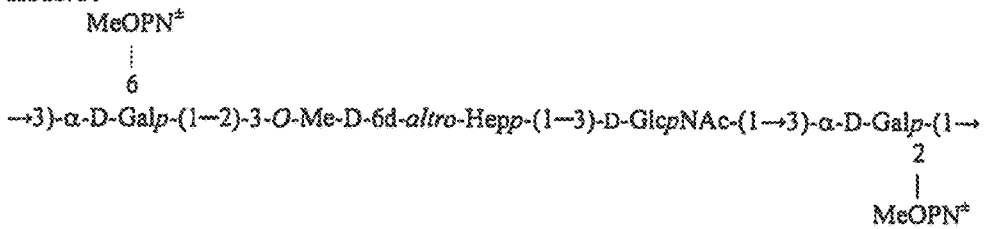

Scheme 1

Scheme 2

Scheme 2a

FIG. 6B

Structure of MeOPN-modified monosaccharide in each CPS     Spot of MeOPN-6-Gal     Detecting antiserum Scheme 4

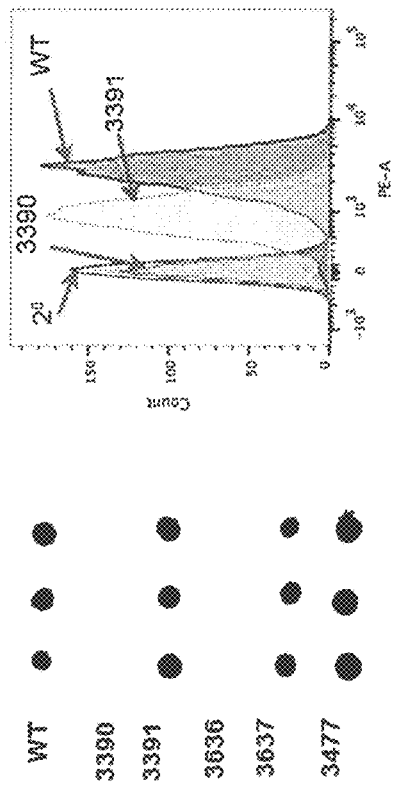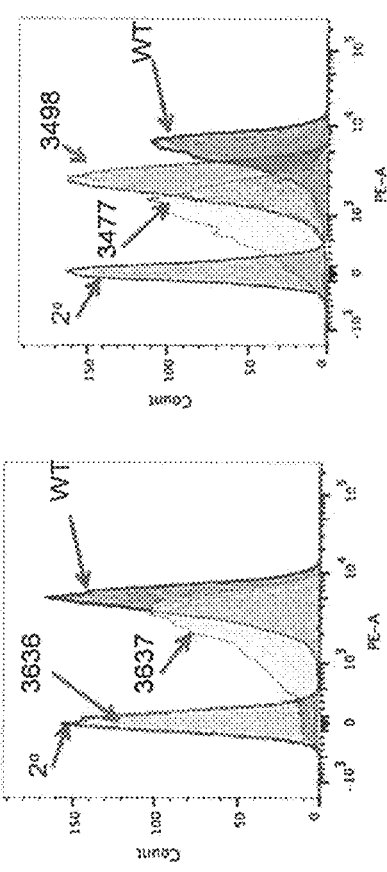

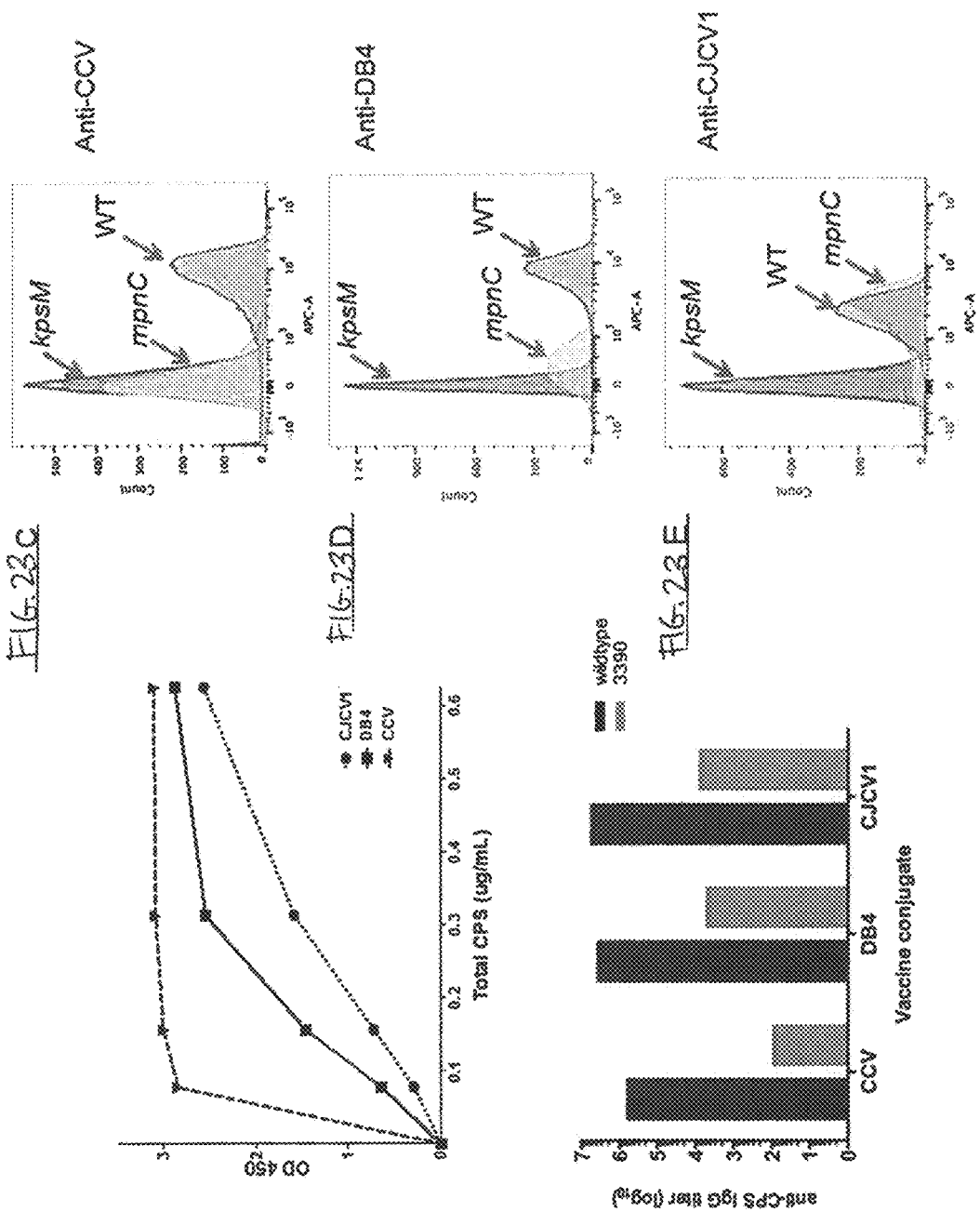

SYNTHETIC ANTIGEN CONSTRUCTS AGAINST CAMPYLOBACTER JEJUNI

CROSS REFERENCE TO RELATED APPLICATIONS

The present application is a Continuation-In-Part of co-pending U.S. Utility patent application Ser. No. 14/933,793 filed Nov. 5, 2015, which claims the benefit of U.S. Provisional Patent Application No. 62/075,399 filed Nov. 5, 2014, and the benefit of U.S. Provisional Patent Application No. 62/127,935 filed Mar. 4, 2015 the entire disclosures of which are incorporated by reference herein.

SEQUENCE LISTING

The instant application contains a Sequence Listing which has been submitted in ASCII format via EFS-Web and is hereby incorporated by reference in its entirety. Said ASCII copy, created on Oct. 5, 2016 is named "103281CIP_ST25.txt" and is 4.52 kilobytes in size.

FIELD OF THE INVENTION

The inventive subject matter of the instant invention relates to immunogenic synthetic constructs capable of inducing an immune response against *Campylobacter jejuni* (*C. jejuni*) in a subject. The inventive subject matter of the instant invention also relates to compositions comprising the immunogenic synthetic constructs as well as methods of inducing an immune response against *C. jejuni* in a subject.

BACKGROUND OF THE INVENTION

Diarrheal diseases are a major cause of morbidity and mortality in the developing world. Among the most frequent bacterial causes of diarrhea are enterotoxigenic *Escherichia coli* (ETEC), *Shigella* species, and *C. jejuni*. Indeed, *C. jejuni* is estimated to cause 2.5 million cases of gastroenteritis annually in the United States and greater than 400 million cases worldwide. In developing countries, *C. jejuni* gastroenteritis is primarily a pediatric disease. The symptoms of *C. jejuni* gastroenteritis include diarrhea, abdominal pain, fever and sometimes vomiting. Stools usually contain mucus, fecal leukocytes and blood, although watery diarrhea is also observed. The disease is zoonotic, and wild and domesticated birds represent a major reservoir. *C. jejuni* is a major foodborne infection, most often being associated with contaminated poultry, but major outbreaks have been associated with water or raw milk contamination.

In addition to causing gastroenteritis, *C. jejuni* can also cause several undesirable post-infectious conditions, including inflammatory bowel syndrome, and a spondyloarthropathy known as Reiter's Syndrome. Moreover, recent studies have indicated an association between *C. jejuni* infections and malnutrition and growth stunting in young children in resource-limited settings.

Another possible debilitating complication of *C. jejuni* infection is the development of Guillain-Barré Syndrome (GBS), a post-infectious polyneuropathy that can result in paralysis (Allos, B. M., J. Infect. Dis 176 (Suppl 2):S125-128 (1997).) *C. jejuni* is one of a limited number of bacteria that can endogenously synthesize sialic acid, a nine carbon sugar that is found in mammalian cells. The association between *C. jejuni* and GBS is reportedly due to molecular mimicry between the sialic acid containing-outer core of the lipooligosaccharide (LOS) present in *C. jejuni* and human gangliosides (Moran, et al., J. Endotox. Res. 3: 521 (1996).) It is believed that antibodies generated by a human subject against the LOS cores of *C. jejuni* may cause an undesirable autoimmune response to neural tissue in the subject. Indeed, studies suggest that LOS synthesis in *Campylobacter* is controlled by a number of genes, including genes encoding enzymes involved in the biosynthesis of sialic acid. The sialic acid is then incorporated into LOS. This is consistent with the observed molecular mimicry of LOS and human gangliosides in GBS. (Aspinall, et al., Eur. J. Biochem., 213: 1029 (1993); Aspinall, et al., Infect. Immun. 62: 2122-2125 (1994); Aspinall, et al., Biochem 33: 241 (1994); Salloway et al., Infect. Immun., 64: 2945 (1996).)

*C. jejuni* is a Gram-negative bacterium, having surface capsular polysaccharides (CPSs) that are involved in colonization and invasion and against which serum antibodies are generated. Recent analysis of the *Campylobacter* genome sequence has resulted in the identification of a complete set of capsule transport genes similar to those seen in type II/III capsule loci in the Enterobactericeae (Parkhill et al., Nature, 403: 665 (2000); Karlyshev et al., Mol. Microbiol., 35: 529 (2000).) Subsequent genetic studies in which site-specific mutations were made in several capsule transport genes indicate that the capsule is the major serodeterminant of the Penner serotyping scheme (Karlyshev et al., Mol. Microbiol., 35: 529 (2009).) The Penner scheme is one of two major serotyping schemes of *campylobacters* and was originally thought to be based on lipopolysaccharide O side chains (Moran and Penner, J. Appl. Microbiol., 86:361 (1999).) It is now believed that the structures previously described as O side chains are, in fact, polysaccharide capsules. Interestingly, although *C. jejuni* capsular moieties are important in serodetermination, and despite over 47 Penner serotypes of *C. jejuni* having been identified, it is believed that most *Campylobacter* diarrheal disease is caused by only a limited number of these serotypes. Therefore, only selected strains of *C. jejuni*, predicated on epidemiological studies, may provide suitable candidate strains for development of potential vaccine compositions.

Several immunogenic CPS-$CRM_{197}$ conjugates associated with prevalent *C. jejuni* serotypes have been created. (Monteiro et al., (2009) *Infect. Immun.* 77, 1128-1136; Bertolo, L, et al. (2012) *Carbohy Res* 366; 45-49.) An immunogenic *C. jejuni* CPS conjugate vaccine capable of protecting nonhuman primates against *C. jejuni* diarrhea has been developed. (Monteiro et al., (2009) *Infect. Immun.* 77, 1128-1136, U.S. Pat. No. 9,084,809.) U.S. Pat. No. 9,084,809 describes, inter alia, an anti-*C. jejuni* immunogenic composition composed of a capsule polysaccharide polymer of *C. jejuni* strain 81-176 (also referred to herein as serotype HS23/36) that is capable of inducing an immune response in BALB/c mice. This reference teaches that the HS23/36 capsule polysaccharide comprises trisaccharides of galactose, 3-O-methyl-6-deoxy-altro-heptose and N-acetyl glucosamine; specifically, the immunogenic polysaccharide polymer comprises a repeating trisaccharide structure having the formula [→3)-α-D-Gal-(1→2)-6d-3-O-Me-α-D-altro-Hep-(1→3)-β-D-GlcNAc-(1→] containing an O-methyl-phosphoramidate at the O-2 position of Gal. Notwithstanding the promise of prototype vaccines, and despite the importance of this organism to human disease, there are yet no licensed, commercially available vaccines against *C. jejuni*. Thus, there currently remains a need for improved immunogenic compositions and methods for preventing or ameliorating diseases associated with *C. jejuni* infection.

BRIEF SUMMARY OF THE INVENTION

In a first aspect, the present invention relates to an immunogenic synthetic construct capable of inducing an immune response against *Campylobacter jejuni* (*C. jejuni*) in a subject, wherein said immunogenic synthetic construct comprises one or more monosaccharides comprising one or more MeOPN moieties. In a particular embodiment, the MeOPN moieties are selected from the group consisting of MeOPN-2-Gal, MeOPN-4-Gal, and MeOPN-6-Gal. In a particular embodiment, the immunogenic synthetic constructs comprise one or more MeOPN-6-Gal, MeOPN-4-Gal, and/or MeOPN-2-Gal monosaccharides.

In yet another aspect, the invention relates to compositions comprising an immunogenic synthetic construct capable of inducing an immune response against *C. jejuni* in a subject, wherein said immunogenic synthetic construct comprises one or more monosaccharides comprising one or more MeOPN moieties. In a particular embodiment, the MeOPN moieties are selected from the group consisting of MeOPN-2-Gal, MeOPN-4-Gal, and MeOPN-6-Gal. In a particular embodiment, the immunogenic synthetic construct comprises one or more MeOPN-6-Gal, MeOPN-4-Gal, and/or MeOPN-2-Gal monosaccharides.

In a further aspect, the invention relates to methods of inducing an immune response against *C. jejuni* in a subject comprising administering to the subject an effective amount of an immunogenic synthetic construct, wherein said immunogenic synthetic construct comprises one or more monosaccharides comprising one or more MeOPN moieties. In a particular embodiment, the MeOPN moieties are selected from the group consisting of MeOPN-2-Gal, MeOPN-4-Gal, and MeOPN-6-Gal. In a particular embodiment, the immunogenic synthetic construct comprises one or more MeOPN-6-Gal, MeOPN-4-Gal, and/or MeOPN-2-Gal monosaccharides. In a particular embodiment, the methods may further comprise administering one or more boosting doses of the immunogenic synthetic construct. In particular embodiments, the effective amount is an amount from about 0.1 µg to about 10 mg of immunogenic synthetic construct.

In a further aspect, the invention relates to methods of inducing an immune response against *C. jejuni* in a subject comprising administering to the subject an effective amount of a composition comprising an immunogenic synthetic construct, wherein the immunogenic synthetic construct comprises one or more monosaccharides comprising one or more MeOPN moieties. In a particular embodiment, the MeOPN moieties are selected from the group consisting of MeOPN-2-Gal, MeOPN-4-Gal, and MeOPN-6-Gal. In a particular embodiment, the immunogenic synthetic construct comprises one or more MeOPN-6-Gal, MeOPN-4-Gal, and/or MeOPN-2-Gal monosaccharides. In a particular embodiment, the methods may further comprise administering one or more boosting doses of the immunogenic synthetic construct. In particular embodiments, the effective amount is an amount from about 0.1 µg to about 10 mg of immunogenic synthetic construct.

In various additional aspects, the invention relates to an immunogenic synthetic construct for use in inducing an immune response against *C. jejuni* in a subject, wherein said immunogenic synthetic construct comprises one or more monosaccharides comprising one or more MeOPN moieties. In a particular embodiment, the MeOPN moieties are selected from the group consisting of MeOPN-2-Gal, MeOPN-4-Gal, and MeOPN-6-Gal. In a particular embodiment, the immunogenic synthetic construct comprises one or more MeOPN-6-Gal, MeOPN-4-Gal, and/or MeOPN-2-Gal monosaccharides. In another aspect, the invention relates to use of an immunogenic synthetic construct for inducing an immune response against *C. jejuni* in a subject wherein said immunogenic synthetic construct comprises one or more monosaccharides comprising one or more MeOPN moieties. In a particular embodiment, the MeOPN moieties are selected from the group consisting of MeOPN-2-Gal, MeOPN-4-Gal, and MeOPN-6-Gal. In a particular embodiment, the immunogenic synthetic construct comprises one or more MeOPN-6-Gal, MeOPN-4-Gal, and/or MeOPN-2-Gal monosaccharides. In another aspect, the invention relates to use of an immunogenic synthetic construct in the manufacture of a medicament for inducing an immune response against *C. jejuni* in a subject, wherein said immunogenic synthetic construct comprises one or more monosaccharides comprising one or more MeOPN moieties. In a particular embodiment, the MeOPN moieties are selected from the group consisting of MeOPN-2-Gal, MeOPN-4-Gal, and MeOPN-6-Gal. In a particular embodiment, the immunogenic synthetic construct comprises one or more MeOPN-6-Gal, MeOPN-4-Gal, and/or MeOPN-2-Gal monosaccharides.

In an additional aspect, the invention relates to a composition comprising an immunogenic synthetic construct for use in inducing an immune response against *C. jejuni* in a subject, wherein the immunogenic synthetic construct comprises one or more monosaccharides comprising one or more MeOPN moieties. In a particular embodiment, the MeOPN moieties are selected from the group consisting of MeOPN-2-Gal, MeOPN-4-Gal, and MeOPN-6-Gal. In a particular embodiment, the immunogenic synthetic construct comprises one or more MeOPN-6-Gal, MeOPN-4-Gal, and/or MeOPN-2-Gal monosaccharides. In another aspect, the invention relates to use of a composition comprising an immunogenic synthetic construct for inducing an immune response against *C. jejuni* in a subject, wherein the immunogenic synthetic construct comprises one or more monosaccharides comprising one or more MeOPN moieties. In a particular embodiment, the MeOPN moieties are selected from the group consisting of MeOPN-2-Gal, MeOPN-4-Gal, and MeOPN-6-Gal. In a particular embodiment, the immunogenic synthetic construct comprises one or more MeOPN-6-Gal, MeOPN-4-Gal, and/or MeOPN-2-Gal monosaccharides. In another aspect, the invention relates to use of a composition comprising an immunogenic synthetic construct in the manufacture of a medicament for inducing an immune response against *C. jejuni* in a subject, wherein the immunogenic synthetic construct comprises one or more monosaccharides comprising one or more MeOPN moieties. In a particular embodiment, the MeOPN moieties are selected from the group consisting of MeOPN-2-Gal, MeOPN-4-Gal, and MeOPN-6-Gal. In a particular embodiment, the immunogenic synthetic construct comprises one or more MeOPN-6-Gal, MeOPN-4-Gal, and/or MeOPN-2-Gal monosaccharides.

In an additional aspect, the invention relates to a pharmaceutical composition comprising an immunogenic synthetic construct for use in inducing an immune response against *C. jejuni* in a subject, wherein the immunogenic synthetic construct comprises one or more monosaccharides comprising one or more MeOPN moieties. In a particular embodiment, the MeOPN moieties are selected from the group consisting of MeOPN-2-Gal, MeOPN-4-Gal, and MeOPN-6-Gal. In a particular embodiment, the immunogenic synthetic construct comprises one or more MeOPN-6-Gal, MeOPN-4-Gal, and/or MeOPN-2-Gal monosaccharides. In another aspect, the invention relates to use of a pharmaceutical composition comprising an immunogenic synthetic construct for inducing an immune response against *C. jejuni* in a subject, wherein the immunogenic synthetic construct comprises one or more monosaccharides comprising one or more MeOPN moieties. In a particular embodiment, the MeOPN moieties are selected from the group consisting of MeOPN-2-Gal, MeOPN-4-Gal, and MeOPN-6-Gal. In a particular embodiment, the immunogenic synthetic construct comprises one or more MeOPN-6-Gal, MeOPN-4-Gal, and/or MeOPN-2-Gal monosaccharides. In another aspect, the invention relates to use of a pharmaceutical composition comprising an immunogenic synthetic construct in the manufacture of a medicament for inducing an immune response against *C. jejuni* in a subject, wherein the immunogenic synthetic construct comprises one or more monosaccharides comprising one or more MeOPN moieties. In a particular embodiment, the MeOPN moieties are selected from the group consisting of MeOPN-2-Gal, MeOPN-4-Gal, and MeOPN-6-Gal. In a particular embodiment, the immunogenic synthetic construct comprises one or more MeOPN-6-Gal, MeOPN-4-Gal, and/or MeOPN-2-Gal monosaccharides.

In an additional aspect, the present invention is directed to methods of synthesizing the immunogenic synthetic constructs of the instant invention as described in detail herein.

In various embodiments of the aforementioned aspects, the immunogenic synthetic construct may be conjugated to a carrier compound, e.g., a carrier protein. In a particular embodiment, the carrier protein contains at least one T-cell epitope. In a particular embodiment, the carrier protein is $CRM_{197}$.

In additional embodiments of the aforementioned aspects, the composition is a pharmaceutical composition. In a particular embodiment, the pharmaceutical composition is a vaccine formulation.

In particular embodiments, the pharmaceutical compositions and the vaccine formulations may comprise an immune-effective amount of one or more adjuvants. In particular embodiments, the adjuvant is selected from the group consisting of toll-like receptor ligands, aluminum phosphate, aluminum hydroxide, monophosphoryl lipid A, liposomes, and derivatives and combinations thereof. In further embodiments, the pharmaceutical compositions and vaccine formulations comprise one or more additional immunoregulatory agents. In a particular embodiment, the immunoregulatory agent is a substance selected from the group consisting of antigens of one or more strains of *C. jejuni*, antigens of ETEC, *Shigella* lipopolysaccharide structures, and unconjugated carrier proteins.

In particular embodiments, the methods of inducing an immune response against *C. jejuni* in a subject comprise administering the construct conjugated to a protein carrier. In a particular embodiment, the protein carrier is $CRM_{197}$. In another particular embodiment, the method further comprises administering the construct or conjugate with an immune-effective amount of one or more adjuvants. In a particular embodiment, the adjuvant is selected from the group consisting of toll-like receptor ligands, aluminum phosphate, aluminum hydroxide, monophosphoryl lipid A, liposomes, and derivatives and combinations thereof. In particular embodiments of the aforementioned aspects, the subject is a human.

In another aspect, the present invention is directed to a method of treating, preventing, or ameliorating a *C. jejuni* bacterial infection in a subject in need thereof comprising administering to the subject one or more doses of immunoglobulins, wherein said immunoglobulins recognize one or more MeOPN moieties in the capsule of said *C. jejuni* bacteria. In one embodiment, the MeOPN moieties are selected from the group consisting of MeOPN-2-Gal, MeOPN-4-Gal, and MeOPN-6-Gal. In a particular embodiment, the MeOPN moiety is MeOPN-4-Gal.

BRIEF DESCRIPTION OF THE DRAWINGS

FIG. 1 depicts the CPS repeating blocks of serotype complexes HS1, HS3, HS4, and HS23/36 and the strain specific heptose units and O-methyl phosphoramidate (MeOPN) linkages. Abbreviations: "±", MeOPN moieties in non-stoichiometric amounts; Gal, galactose; Gro, glycerol; Fru, fructose; Hep, heptose; GlcpNAc, N-acetyl-D-glucosamine. The existence of MeOPN-6-Gal in strain HS23/36 is based on the discovery reported herein.

FIG. 6A and FIG. 6B depict location of some possible MeOPN moieties and capsule cross-reactivity to MeOPN-6-Gal with antibodies to multiple conjugate vaccines. FIG. 6A depicts the structure of possible MeOPN modified monosaccharides on MeOPN-6 Gal in the CPS of the HS 23/36 serotype of *C. jejuni*. All "R" groups present can stand for either H or MeOPN, i.e., each site of modification (Gal-2 or Gal-6) can be substituted with either H or MeOPN. FIG. 6B depicts the structure of MeOPN modified monosaccharide in the CPSs of the indicated serotypes of *C. jejuni*, HS: 4, HS:1, and HS:3. In order to test for capsule cross-reactivity, a spot of MeOPN-6-Gal was combined with the indicated detecting anti-CRM$_{197}$ conjugate antiserum (indicated on the right side of the blot). Data indicate that antibodies to HS23/36, HS4 and HS1 serotypes of *C. jejuni* can react with the synthetic MeOPN-6-Gal construct.

FIG. 10A depicts gel electrophoresis of CRM$_{197}$ and MeOPN→6-β-D-Gal CRM$_{197}$ (compound 14); FIG. 10B depicts Western blot of MeOPN→6-β-D-Gal CRM$_{197}$ (compound 14) with *C. jejuni* HS23/36 whole cell antisera; and FIG. 10C depicts the MALDI-TOF/MS of MeOPN→6-β-D-Gal CRM$_{197}$ (compound 14.) The MeOPN-6-Gal-CRM$_{197}$ vaccine gave a major peak of mass 61,781.206. The mass for CRM$_{197}$ in a similar MALDI experiment was 57,967 daltons (not shown.) Thus, the mass difference was about 3,814 daltons. Since the mass of MeOPN-6-Gal and the linker is 461 daltons (data not shown), this indicates that approximately 8 MeOPN-6-Gal-linker moieties were added per CRM$_{197}$ molecule.

FIG. 16B provides the blot of the construct. The gel and blot were prepared using conventional methods as described in Example 7.

FIG. 22A, FIG. 22B, FIG. 22C, and FIG. 22D depict the characterization of monoclonal DB3. FIG. 22A: Dot blot of whole cells of wildtype 81-176 and various mutants detected with DB3. FIG. 22B: Flow cytometry of wildtype, 3390, and 3391 with DB3. FIG. 22C: Flow cytometry of wildtype, 3636 and 3637 with DB3. FIG. 22D: Flow cytometry of wildtype, 3477, and 3498 with DB3. The peak labeled "2°" in FIGS. 22B, 22C and 22D shows binding of the secondary antibody alone.

FIG. 23A, FIG. 23B, FIG. 23C, FIG. 23D, and FIG. 23E depict the variation of MeOPN levels of different batches of conjugate vaccines. FIG. 23A: DB3 ELISA of three different batches of 81-176-CRM197 conjugate vaccines. FIG. 23B: Endpoint titers of rabbit polyclonal hyperimmune sera to capsules purified from wildtype 81-176 (black bars) and the mpnC mutant (3390; gray bars). FIGS. 23C-E: Flow cytometry comparing binding of rabbit hyperimmune serum against conjugate CCV (FIG. 23C), DB4 (FIG. 23D) and CJCV1, (FIG. 23E) to wildtype 81-176, 3390, the mpnC mutant and 3469, the kpsM mutant.

FIG. 28A: Titer of rabbit polyclonal serum to an 81-176-CRM$_{197}$ and mutants conjugate vaccine. FIG. 28B: Titer of 5 pools of human sera purchased commercially (Sigma Aldrich, St. Louis, Mo.). The pool shown as the diamond symbol is the pool used in FIG. 24.

DETAILED DESCRIPTION

Figure 2:
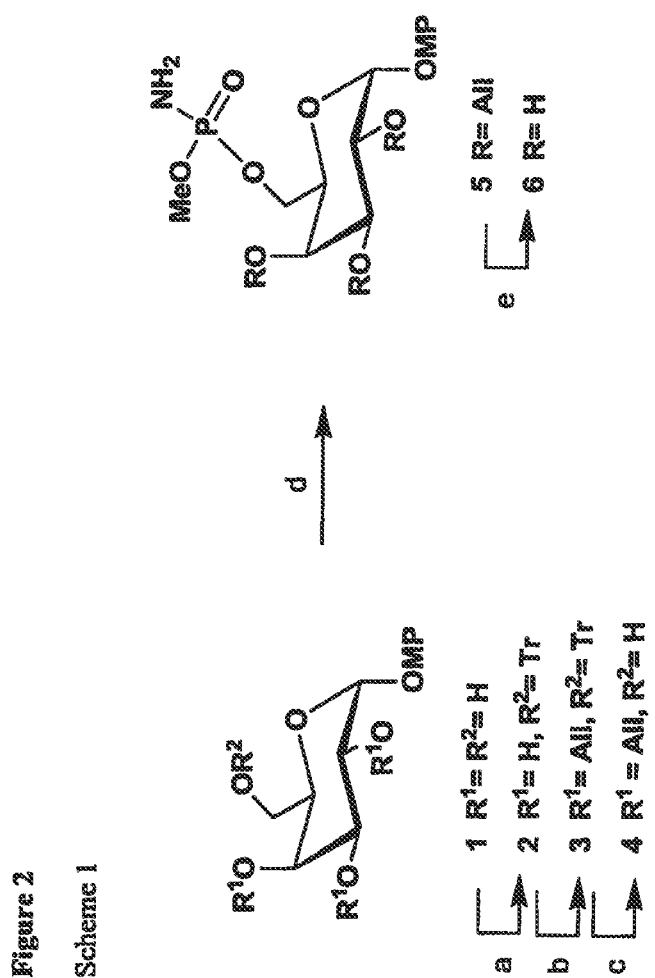
FIG. 2 depicts synthesis of the p-methoxyphenyl glycoside of the MeOPN→6-Gal construct (O-Me-phosphoramidate galactoside), MeOPN→6-α-D-Galp-(1→OMP ("Scheme 1".) The reagents and conditions employed in the steps indicated therein are as follows; (a) TrCl, pyridine, 95%; (b) AllBr, NaH, DMF, 0° C., 89%; (c) 80% AcOH, 80° C., 78%; (d) $PCl_2(O)OMe$, $Et_3N$, $CH_2Cl_2$, then $NH_3(g)$, 19%; (e) $PdCl_2$, MeOH, 39%. Tr, trityl; All, allyl; DMF, dimethyl formamide; OMP, 4-methoxyphenyl group.

While the specification concludes with the claims particularly pointing out and distinctly claiming the invention, it is believed that the present invention will be better understood from the following description.

All percentages and ratios used herein are by weight of the total composition unless otherwise indicated herein. All temperatures are in degrees Celsius unless specified otherwise. All measurements made are at 25° C. and normal pressure unless otherwise designated. The present invention can "comprise" (open ended) or "consist essentially of" the components of the present invention as well as other ingredients or elements described herein. As used herein, "comprising" means the elements recited, or their equivalent in structure or function, plus any other element or elements which are not recited. The terms "having", "containing", and "including" are also to be construed as open ended unless the context suggests otherwise. As used herein, "consisting essentially of" means that the invention may include ingredients in addition to those recited in the claim, but only if the additional ingredients do not materially alter the basic and novel characteristics of the claimed invention.

All ranges recited herein include the endpoints, including those that recite a range "between" two values. Terms such as "about," "generally," "substantially," and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value. Unless otherwise indicated, as used herein, "a" and "an" include the plural, such that, e.g., "a MeOPN-6-Gal monosaccharide" can mean at least one MeOPN-6-Gal monosaccharide, as well as a plurality of MeOPN-6-Gal monosaccharides, i.e., more than one MeOPN-6-Gal monosaccharide.

Where used herein, the term "and/or" when used in a list of two or more items means that any one of the listed characteristics can be present, or any combination of two or more of the listed characteristics can be present. For example, if a vaccine formulation against C. jejuni is described as containing characteristics A, B, and/or C, the vaccine formulation against C. jejuni can contain A feature alone; B alone; C alone; A and B in combination; A and C in combination; B and C in combination; or A, B, and C in combination. The entire teachings of any patents, patent applications or other publications referred to herein are incorporated by reference herein as if fully set forth herein.

Until recently, MeOPN-2-Gal was thought to be the only MeOPN moiety on CPS Gal in C. jejuni strain 81-176 (otherwise referred to herein as serotype HS23/26.) (Kanipes et al., (2006) J Bacteriol. 188, 3273-3279.) By performing genetic and structural analyses of C. jejuni strain HS23/36, however, the inventors have surprisingly discovered a second distinct MeOPN at the O-6-position of the CPS Galactose (MeOPN-6-Gal), and more recently, a third distinct MeOPN moiety at the 4 position of Galactose (MeOPN-4-Gal). As reported herein, the inventors have discovered that, although present in non-stoichiometric amounts, CPS epitopes containing MeOPN units are key C. jejuni immunogenic markers. Moreover, by performing comprehensive immunological analyses of multivalent conjugate vaccines using native CPSs of C. jejuni HS23/36, the inventors have discovered that MeOPN modified polysaccharides are immunogenic and immunodominant over unmodified polysaccharides. Moreover, data provided hereinbelow indicate that MeOPN-4-Gal appears to be a major modification responsible for resistance to complement-mediated killing.

In view of the foregoing, the present invention is directed to immunogenic synthetic constructs capable of inducing an immune response against C. jejuni in a subject. Specifically, in contrast to previous anti-C. jejuni immunogenic polysaccharide constructs or CPS conjugate vaccines, the instant invention is directed to immunogenic synthetic constructs against C. jejuni comprising one or more methyl phosphoramidyl monosaccharides, i.e., an immunogenic synthetic construct comprising one or more O-methyl phosphoramidate (MeOPN) moieties, including but not limited to, MeOPN at the 2 position, 4 position, and/or the 6 position of galactose.

In a particular embodiment, as specifically described in detail herein, the immunogenicity and efficacy of a synthetic MeOPN→6 Gal construct against C. jejuni has surprisingly been discovered. Thus, in various aspects, the invention includes synthetic saccharide constructs that comprise one or more synthetic MeOPN→6 Gal monosaccharides, compositions comprising these synthetic saccharide constructs, and methods of using these synthetic saccharide constructs. In addition, in view of the recent unexpected discovery of MeOPN-4-Gal epitopes in the capsule of C. jejuni disclosed herein, the instant invention also includes synthetic constructs that comprise one or more MeOPN→4 Gal monosaccharides, compositions comprising these synthetic saccharide constructs, and methods of using these synthetic saccharide constructs.

As used herein, the term "monosaccharide" refers to a single sugar residue, including derivatives therefrom. As one of skill in the art will appreciate, within the context of an oligosaccharide, an individual monomer unit is a monosaccharide which may be bound through a hydroxyl group to another monosaccharide.

In a particular embodiment, the synthetic saccharide constructs of the instant invention are conjugated to a carrier protein. Compositions, e.g., pharmaceutical anti-C. jejuni formulations, including vaccine formulations, comprising the synthetic constructs (unconjugated or conjugated to a carrier protein) are contemplated herein. Also contemplated herein are methods of inducing an immune response against C. jejuni in a subject comprising administering to the subject an effective amount of a synthetic construct and/or a composition of the instant invention, e.g., a vaccine formulation, comprising a synthetic construct in conjugated and/or unconjugated forms.

The immunogenic synthetic constructs and conjugates of the instant invention are believed to offer multiple advantages over previous conjugate vaccines made from purified C. jejuni capsule polysaccharides. For example, data indicate that MeOPN moieties are phase variable in C. jejuni, thus the level of this epitope normally present in vaccine formulations obtained from purified capsules can vary. As a result of this natural variability, different preparations from the same strain of C. jejuni may have different levels of this MeOPN epitope, and thus different immunogenicity. In contrast, by using a synthetic approach, a pharmaceutical formulation (e.g., a vaccine formulation) comprising a desired level of MeOPN epitopes can be obtained, and provides the advantage that the potential immunogenicity of the vaccine may be controlled. In addition, as evident from the examples provided herein, the synthetic C. jejuni monosaccharide construct antigens of the instant invention may have broader coverage than polysaccharides, thus potentially reducing the valency required for a vaccine against C. jejuni. Thus, it is contemplated herein that the synthetic constructs disclosed herein are antigenic determinants that can be used as effective antigens in a vaccine formulation in which a single epitope could cross-protect across more than one C. jejuni serotype. Moreover, since the use of the synthetic constructs of the instant invention eliminates the need to grow C. jejuni (a fastidious organism) and to purify the capsule, the synthetic constructs are more cost-effective and thus provide a commercial advantage and improvement compared to other vaccines which use purified CPS.

In addition to the foregoing, the synthetic constructs of the instant invention are not only immunogenic, but also provide the advantage that the synthetic approach precludes concerns about development of autoimmunity because the method does not require purification of capsules away from C. jejuni lipooligosaccharides (LOS) which often contains structures that mimic human gangliosides structurally and can induce an autoimmune response that results in Guillain Barré Syndrome.

As understood by one of skill in the art, "MeOPN→6 Gal", "MeOPN-6-Gal", "MeOPN-6-Gal construct" and like terms refer to a galactose monosaccharide which is modified to include an O-methyl phosphoramidate moiety at the O-6 position of the galactose monosaccharide. As understood herein, the synthetic MeOPN-6-Gal construct may comprise various other "R" groups in addition to the MeOPN moiety. The term encompasses constructs of various modified forms, e.g., MeOPN→6-α-D-Galp-(1→OMP, i.e., 4-Methoxyphenyl 6-O-methyl-phosphoramidate-α-D-galactopyranoside; as well as activated forms including a linker, e.g., as MeOPN→6-β-D-Galp-(1→O(CH$_2$)$_5$NH$_2$, i.e., 5-Aminopentanyl 6-O-methylphosphoramidate-β-D-galactopyranoside. Similarly, "MeOPN-2-Gal" and like terms refers to an O-methyl phosphoramidate moiety at the O-2 position of the galactose monosaccharide, while "MeOPN-4-Gal" and like terms refers to an O-methyl phosphoramidate moiety at the O-4 position of the galactose monosaccharide. As understood herein, synthetic MeOPN-2-Gal and MeOPN-4-Gal constructs may also comprise various other "R" groups in addition to the MeOPN moiety, and the terms encompass constructs of various modified forms such as discussed above regarding MeOPN-6-Gal.

As understood herein, an "immunogenic synthetic construct" or more simply "synthetic construct", and like terms, refer to an in vitro, i.e., chemically produced, non-naturally occurring ("man-made") compound comprising one or more monosaccharides comprising one or more MeOPN moieties capable of inducing an immune response against *Campylobacter jejuni* (*C. jejuni*) in a subject. As used herein, "synthetic" refers to material which is substantially or essentially free from components, such as endotoxins, glycolipids, unrelated oligosaccharides, etc., which normally accompany a compound when it is isolated. In a particular embodiment, the immunogenic synthetic construct comprises one or more MeOPN→6 Gal monosaccharides which can elicit an immune response to *C. jejuni* in a subject. In another embodiment, the immunogenic synthetic construct comprises one or more MeOPN→4 Gal monosaccharides which can elicit an immune response to *C. jejuni* in a subject. In yet another embodiment, the immunogenic synthetic construct comprises one or more MeOPN→2 Gal monosaccharides which can elicit an immune response to *C. jejuni* in a subject. As discussed above, the MeOPN monosaccharides may also comprise various other "R" groups in addition to the MeOPN moiety or moieties.

As contemplated herein, in a particular embodiment, the immunogenic synthetic construct of the instant invention comprises one or more synthetic MeOPN monosaccharides selected from the group consisting of MeOPN-2-Gal, MeOPN-4-Gal, and MeOPN-6-Gal. In another embodiment, the construct may be further chemically associated in combination with one or more other saccharides, and/or chemical linkers. For example, it is contemplated herein that a synthetic construct of the present invention can comprise MeOPN-2-Gal, MeOPN-4-Gal, and/or MeOPN-6-Gal alone or in combination with one or more other monosaccharides. Monosaccharides found in the CPS of *C. jejuni* are particularly contemplated herein, e.g., one or more of fructose, galactose, glucose, or heptose monosaccharides, and optionally substituted with one or more additional MeOPN moieties, or other antigens against *C. jejuni*.

As discussed below in detail, it is contemplated herein that the synthetic constructs of the instant invention, including synthetic constructs comprising one or more MeOPN→6 Gal, MeOPN→4 Gal, and/or MeOPN→2 Gal monosaccharides, may be activated and conjugated to a carrier protein or may be used in an unconjugated form. In a particular embodiment, when conjugated to a carrier protein, the synthetic construct may be referred to herein as a "conjugate vaccine" or as a "conjugate."

As used herein, "a subject" includes an animal, including but not limited to birds and mammals. Human beings are also encompassed in this term. As particularly contemplated herein, subjects include, e.g., any animal or human that has been infected with, or is at risk of being infected with, *C. jejuni*. A subject may be naïve, or non-naïve with regard to *C. jejuni* exposure. In particular, suitable subjects (patients) include, but are not limited to, farm animals (e.g., chickens) as well as non-human primates and human patients.

As understood herein, a synthetic construct of the instant invention may be administered to a subject in order to induce an immune response in the subject and thus prevent and/or ameliorate one or more pathological conditions associated with *C. jejuni* in the subject. As understood herein, the concept of "inducing" an immune response in a subject refers to triggering a humoral and/or cellular immune response in the subject. Thus, "in a sufficient amount to elicit an immune response" or "in an effective amount to stimulate an immune response" (e.g., to MeOPN moieties present in a preparation) and like terms means an amount that is capable of producing a detectable difference between an immune response indicator measured before and after administration of a particular antigen preparation. Immune response indicators include but are not limited to: antibody titer or specificity, as detected by an assay such as enzyme-linked immunoassay (ELISA), bactericidal assay (e.g., to detect serum bactericidal antibodies), flow cytometry, immunoprecipitation, Ouchter-Lowry immunodiffusion; binding detection assays of, for example, spot, Western blot or antigen arrays; cytotoxicity assays, and the like.

The concept of "treating, preventing and/or ameliorating" a *C. jejuni* infection, and/or one or more pathological conditions associated with *C. jejuni*, encompasses, e.g., averting or hindering the onset or development of a pathological condition associated with *C. jejuni* infection, as well as curing, retarding, and/or reducing the severity of one or more pathological conditions associated with *C. jejuni*.

As used herein, the term "one or more pathological conditions associated with *C. jejuni*" refers to an undesirable condition in a subject caused by infection with *C. jejuni* ("campylobacteriosis".) As contemplated herein, such pathological conditions include clinical conditions and diseases which may arise in a subject upon infection with *C. jejuni*, as well as conditions which may develop in a subject as a consequence of a previous instance of campylobacteriosis. These conditions are familiar to one of skill in the art and include, but are not limited to, *campylobacter* gastroenteritis, Reiter's Syndrome, inflammatory bowel syndrome, and Guillain-Barré Syndrome (GBS.)

Synthesis of the synthetic constructs of the instant invention, including, e.g., the controlled synthesis and introduction of MeOPN to a simple sugar, activation of the resulting synthetic construct, addition of a chemical linker, and conjugation of a carrier protein, may be performed using commercially available materials and methodologies familiar to one or skill in the art, e.g., a carbohydrate chemist. Particular methods of compound synthesis (synthesis schemes) are described in detail in the below examples. It is contemplated herein that the methods of synthesizing the compounds disclosed in the below examples and synthesis schemes are included among the aspects of the instant invention.

As understood by one of skill in the art, the chemical synthesis of a monosaccharide may be achieved using well-established procedures in carbohydrate chemistry; however, monosaccharides for use as starting compounds in the disclosed synthesis schemes may be obtained from a variety of commercial vendors and chemically modified by one of skill in the art to arrive at the immunogenic synthetic construct of the instant invention, e.g., according to, but not limited to, the synthesis schemes disclosed herein. Published chemical modifications include, but are not limited to, the method for the synthesis of 4-methoxyphenyl-α-D-galactopyranoside proposed in Comfort, et al., Biochem. 46: 3319-

3330 (2007.) Briefly, 4-methoxyphenyl-α-D-galactopyranoside may be synthesized from D-galactose by acetylation, glycosidation with 4-methoxyphenol, followed by Zemplén deacetylation according to published methods. (Montgomery et al. (1942) *J. Am. Chem. Soc.* 64, 690-694.)

Similarly, various strategies for the synthesis and introduction of MeOPN to a monosaccharide are familiar to one of skill in the art. For example, a particular method is described in Mara et al, *Bioorg. Med. Chem. Lett.* 6180-6183 (2011.) This reference describes a reaction with ethyl dichlorophosphate followed by reaction with protected amines.

As discussed above, the synthetic construct of the instant invention may be chemically activated in order to add one or more chemical linking group(s) capable of reacting with a carrier protein. As contemplated herein, the activation of a construct of the instant invention may be performed according to conventional methods familiar to one of skill in the art. Such methods include, e.g., the use of cyanylating reagents such as 1-cyano-4-dimethylamino pyridinium tetrafluoroborate (CDAP); carbodiimides, hydrazides, active esters, p-nitrobenzoic acid, N-hydroxysuccinimide, and trimethylsilyl trifluoromethanesulfonate (TMSOTf.) Activating the construct may also be achieved by reacting the saccharide with 2,2,6,6-tetramethylpiperidin-1-oxyl (TEMPO.) See, e.g., US Pub. No. 2014/0141032.

While the immunogenic synthetic constructs of the instant invention may be administered to a subject in an unconjugated form, it is contemplated herein that upon synthesis, the construct may be chemically activated and chemically conjugated in vitro to one or more carrier molecules, e.g., one or more T cell-dependent carrier proteins, prior to administration in order to provide an enhanced immune response. Indeed, as appreciated by one of skill in the art, children are only capable of mounting an IgM response in the face of polysaccharide antigens; adults are capable of generating an IgG, IgA and IgM response. Thus, by linking a carrier protein to the synthetic construct, the immune response triggered in vivo by the construct will change from a T-cell independent response to one which is T-cell dependent. As such, the immune response that is triggered is enhanced and thus markedly different than what might otherwise be produced in vivo by an unconjugated construct.

In a particular embodiment, the carrier molecule is a carrier protein. As used herein, a "carrier protein" refers to a protein, or an analog or fragment thereof, which in a particular embodiment ideally contains at least one T-cell epitope. Suitable carrier proteins for use with the instant invention are familiar to one of skill in the art and are commercially available and/or may be created and purified by one of skill in the art using conventional methods. For example, carrier proteins for use with the instant invention include bacterial toxins that are immunologically effective carriers and that have been rendered safe by chemical or genetic means for administration to a subject. Examples include, but are not limited to, inactivated bacterial toxins such as diphtheria toxoid, $CRM_{197}$, tetanus toxoid, pertussis toxoid, *E. coli* heat labile enterotoxin (LT), the binding component of *E. coli* heat labile enterotoxin (LTB), *E. coli* adhesins and/or fimbriae, and exotoxin A from *Pseudomonas aeruginosa*. Bacterial outer membrane proteins such as, e.g., outer membrane complex c (OmpC), porins, transferrin binding proteins, pneumococcal surface protein A (PspA), pneumococcal adhesin protein (PsaA), or pneumococcal surface proteins BVH-3 and BVH-11 can also be used. Other proteins, such as protective antigen (PA) of *Bacillus anthracis*, ovalbumin, keyhole limpet hemocyanin (KLH), human serum albumin, bovine serum albumin (BSA) and purified protein derivative of tuberculin (PPD) can also be used.

In a particular embodiment, the carrier protein is selected from the group consisting of inactivated bacterial toxins, bacterial outer membrane proteins, protective antigen (PA) of *Bacillus anthracis*, ovalbumin, keyhole limpet hemocyanin (KLH), human serum albumin, bovine serum albumin (BSA) and purified protein derivative of tuberculin (PPD.) In a particular embodiment, the inactivated bacterial toxin is selected from the group consisting of diphtheria toxoid, cross-reactive material 197 ($CRM_{197}$), tetanus toxoid, pertussis toxoid, the binding component of *E. coli* heat labile enterotoxin (LTB), *E. coli* adhesins and/or fimbriae, and exotoxin A from *Pseudomonas aeruginosa*. In a particular embodiment, the carrier protein is the inactivated bacterial toxin $CRM_{197}$. In another particular embodiment, the bacterial outer membrane protein is selected from the group consisting of outer membrane complex c (OmpC), porins, transferrin binding proteins, pneumococcal surface protein A (PspA), pneumococcal adhesin protein (PsaA), pneumococcal surface protein BVH-3, and pneumococcal surface protein BVH-11. Such carrier proteins are available from a variety of commercial vendors.

It is also contemplated herein that proteins from ETEC may be used as carrier molecules. Possible ETEC protein carriers include, but are not limited to, the B subunit of the heat labile enterotoxin, and fimbrial subunits. The latter includes subunits of various ETEC colonization factors such as, e.g., CfaI (CfaE and/or CfaB), CS6 (CssB and/or CssA), CS3 (CstG and/or CstH), CS17 (CsbA and/or CsbD) and CS1 (CooA.) Further examples of ETEC proteins and details regarding the use of ETEC proteins as possible carrier molecules can be found, e.g., in US 2015/0258201 A1, the entire contents of which are incorporated by reference herein.

As contemplated herein, a carrier protein may be linked to more than one synthetic construct in order to enhance the immunogenicity of the construct against *C. jejuni*. In one embodiment, multiple synthetic MeOPN-6-Gal constructs are linked to a single carrier protein. In a particular embodiment, a conjugate vaccine of the instant invention comprising a MeOPN-6-Gal:$CRM_{197}$ ratio (w/w) of at least 8:1 or more is envisioned herein. In another embodiment, multiple synthetic MeOPN-4-Gal and/or β-GlcNAc-(1-3)-[MeOPN-4]-Gal constructs are linked to a single carrier protein. In a particular embodiment, a conjugate vaccine of the instant invention comprising a MeOPN-4-Gal:$CRM_{197}$ ratio (w/w) of at least 8:1 or more is envisioned herein.

After conjugation, free and conjugated saccharide constructs can be separated using a variety of conventional methods. Purification methods are familiar to one of skill in the art and include, e.g., ultrafiltration, size exclusion chromatography, density gradient centrifugation, hydrophobic interaction chromatography, and/or ammonium sulfite fractionation.

Possible methods of conjugating an activated monosaccharide or saccharide construct of the instant invention to a carrier protein are familiar to one of skill in the art and include, e.g., reductive amination of a monosaccharide involving the coupling of the resulting amino group with one end of an adipic acid linker group, and then coupling a protein to the other end of the adipic acid linker group; cyanylation conjugation, wherein the saccharide construct is activated either by cyanogens bromide (CNBr) or by 1-cyano-4-dimethylammoniumpyridinium tetrafluoroborate (CDAP) to introduce a cyanate group to the hydroxyl group, which forms a covalent bond to the amino or hydrazide group upon addition of the protein component; and a carbodiimide reaction, wherein carbodiimide activates the carboxyl group on one component of the conjugation reaction, and the activated carbonyl group reacts with the amino or hydrazide group on the other component. If necessary, these reactions may also be employed to activate the components of the carrier protein prior to the conjugation reaction. As contemplated herein, in a particular embodiment, a process involving the introduction of amino groups into the monosaccharide (e.g., by replacing terminal =O groups with —NH$_2$) followed by derivatization with an adipic diester (e.g., adipic acid N-hydroxysuccinimido diester) and reaction with carrier protein may be used.

It is also contemplated herein that the synthetic construct may be linked directly to the carrier protein. Direct linkages to the protein may comprise oxidation of the monosaccharide followed by reductive amination with the protein using conventional methods.

The synthetic constructs of the instant invention, e.g., comprising one or more MeOPN-6-Gal monosaccharides, MeOPN-4-Gal monosaccharides and/or MeOPN-2-Gal monosaccharides may further comprise one or more additional saccharides, as well as one or more additional chemical compounds or moieties or fragments or derivatives thereof. A variety of chemical compounds can serve as a chemical backbone to link the various components of an immunogenic synthetic construct of the instant invention, and/or to link the synthetic construct as a whole to one or more carrier proteins. Compounds that may be used to make a polymeric construct or conjugate include, e.g., modified starch moieties, cyclodextrin, and nigeran.

As particularly contemplated herein, the construct may comprise additional saccharides, moieties, or compounds which may be incorporated for a variety of reasons, e.g., to increase the chemical stability of the synthetic construct and/or to enhance the delivery or bioavailability of the construct. In a particular embodiment, it is contemplated herein that additional saccharides, moieties, and compounds may be chemically associated with one or more MeOPN-6-Gal, MeOPN-4-Gal, and/or MeOPN-2-Gal constructs either directly or indirectly through one or more linkers or other compounds, in order to enhance the immunogenicity of the synthetic construct against *C. jejuni* in a subject. Thus, additional saccharides for use in a synthetic construct of the instant invention include, but are not limited to, monosaccharides present in the capsule of various *C. jejuni* strains, e.g., galactose or other modified forms thereof, including fructose, glucose, heptose, N-acetyl galactosamine, N-acetyl glucosamine, glucitol, glucose or modified forms or derivatives thereof, including monosaccharides containing one or more MeOPN moieties, including but not limited to MeOPN-2-Gal, MeOPN-4-Gal, and MeOPN-6-Gal. Such saccharides may be used in an amount and in combination with one or more other MeOPN monosaccharides which may enhance the immunogenicity of the synthetic construct against *C. jejuni*. For example, FIG. 1 lists the CPS repeating blocks and specific heptose units and MeOPN linkages of *C. jejuni* serotype complexes HS1, HS3, HS4, and HS23/36.

Figure 15:
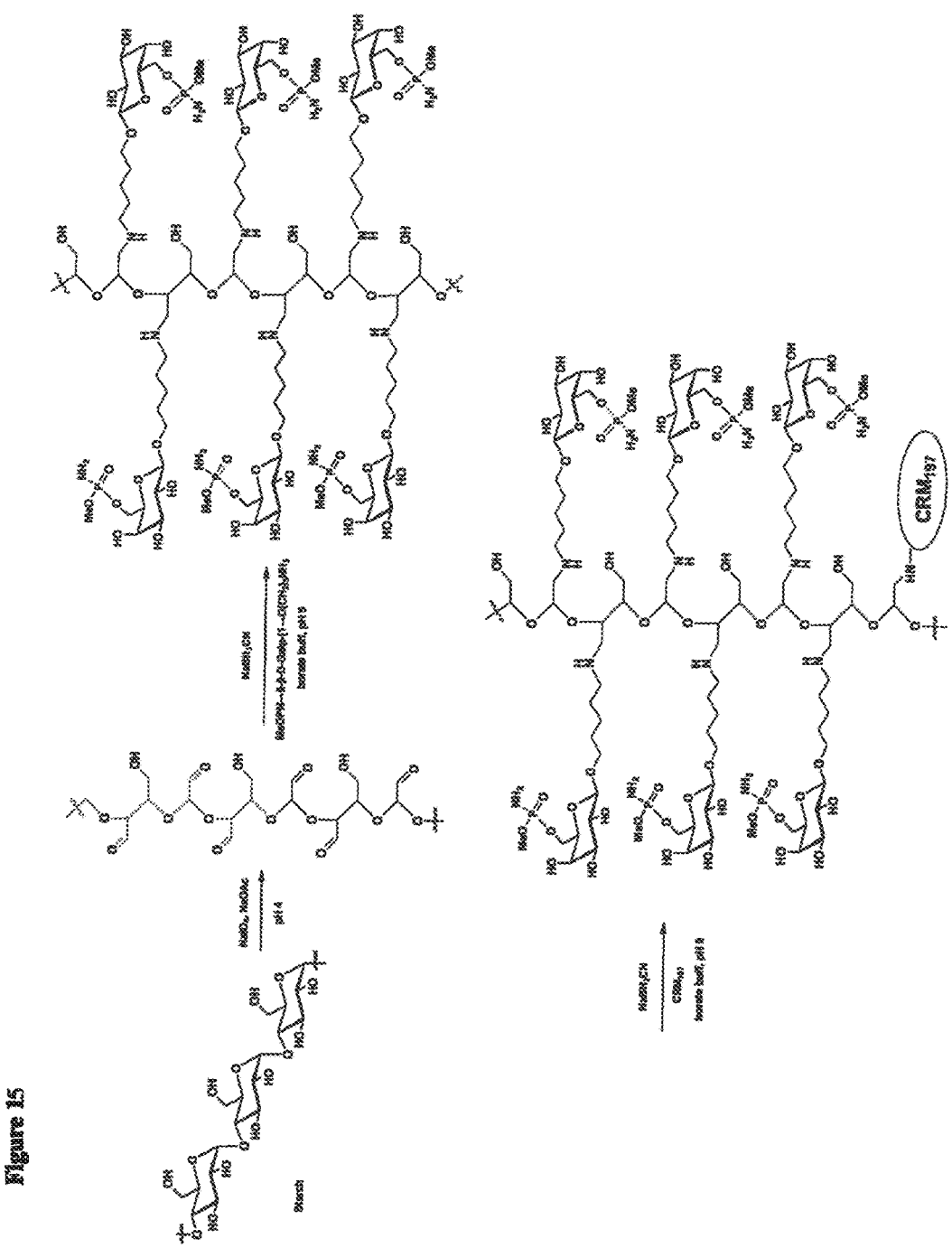
FIG. 15 depicts the synthesis of a synthetic polymeric conjugate of the invention comprising multiple MeOPN-6-Gal monosaccharides chemically associated using a starch backbone which is equipped with a linker and conjugated to the carrier protein, CRM$_{197}$.
Figure 18:
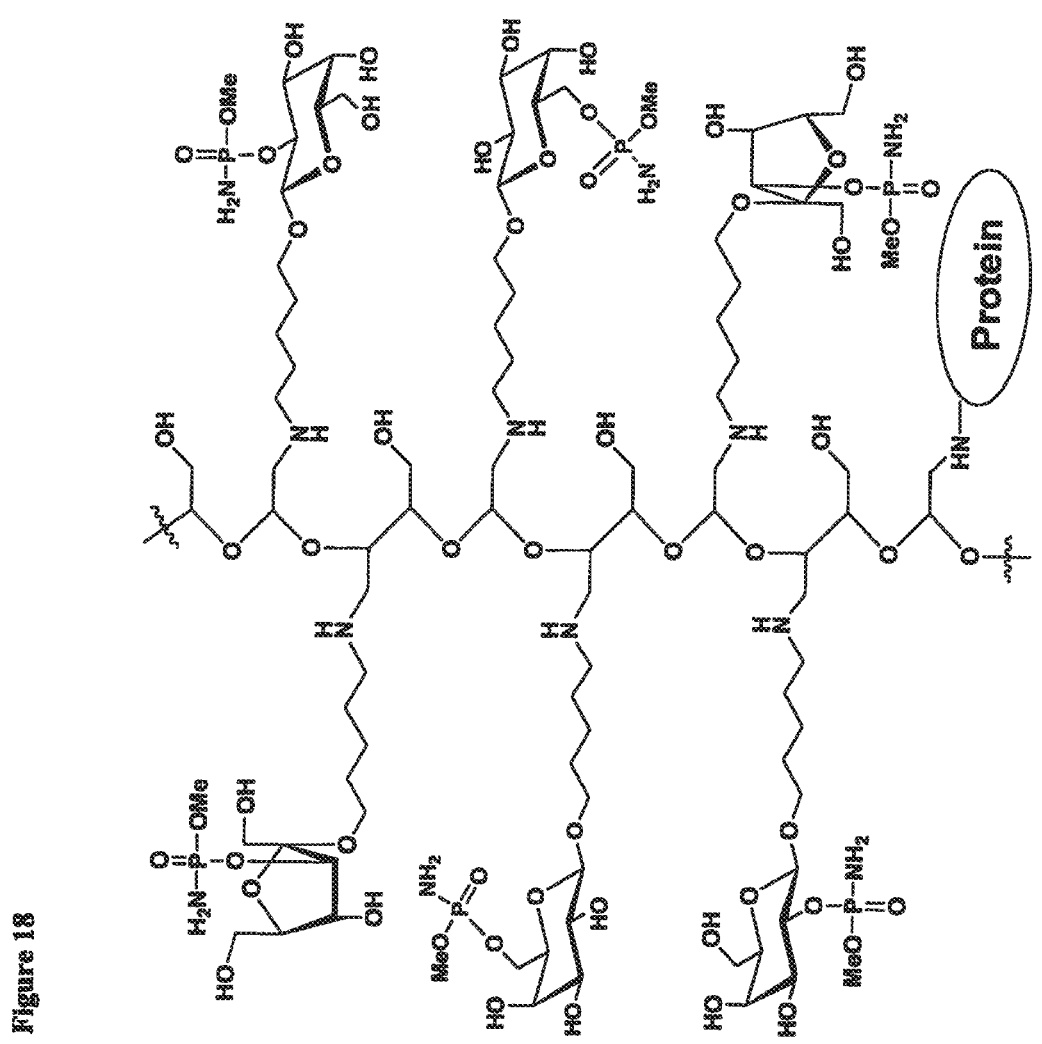
FIG. 18 depicts another synthetic polymeric construct of the invention comprising multiple MeOPN-6-Gal monosaccharides chemically associated with other saccharides using a starch backbone and which is equipped with a linker and conjugated to a carrier protein. Specifically, as depicted, the synthetic polymer comprises multiple MeOPN-6-Gal, MeOPN-2-Gal, and MeOPN-1-Fru monosaccharides.

In view of the foregoing, as provided in the below examples, FIG. 15 depicts a synthetic polymeric construct which comprises more than one MeOPN-6-Gal monosaccharide; FIG. 18 depicts a synthetic polymeric construct which comprises more than one MeOPN-6-Gal monosaccharide and also comprises additional monosaccharides MeOPN-2-Gal and MeOPN-1-Fru. It is contemplated herein that the presence of these additional components in a construct or conjugate of the instant invention will enhance the immunogenicity of the construct or conjugate against *C. jejuni*. In a particular embodiment, it is contemplated herein that these and other synthetic constructs of the instant invention may be modified to include one or more MeOPN-4-Gal epitopes.

As understood herein, "associated" includes any manner of chemical combination, e.g., the synthetic construct may comprise several synthetic MeOPN-6-Gal, MeOPN-4-Gal, and/or MeOPN-2-Gal monosaccharides chemically joined in a chain as a polymer, or in various combinations with any number of one or more other saccharides. Such construct may be further conjugated to a carrier protein.

As contemplated herein, the methods of the instant invention are directed to inducing an immune response against *C. jejuni* in a subject comprising administering an effective amount of the immunogenic synthetic construct to the subject. In particular embodiments, the construct is administered to the subject in the form of a composition comprising the synthetic construct as an active pharmaceutical ingredient, e.g., a pharmaceutical composition, more particularly, as a vaccine formulation comprising the synthetic construct linked to a carrier protein. Thus, as used herein, an "effective amount" can refer to the amount of the immunogenic synthetic construct alone or in a composition, including in a pharmaceutical composition comprising one or more other active pharmaceutical agents or excipients.

Moreover, as understood herein, an "effective amount" refers to an immunologically effective amount of the immunogenic synthetic construct (conjugated or unconjugated) suitable to elicit an immune response in the subject. As discussed above, an "immune response" encompasses triggering a humoral and/or cellular immune response in the subject. As a result, a meaningful clinical benefit to the subject is provided. Such benefit may be, e.g., preventing, ameliorating, treating, inhibiting, and/or reducing one of more pathological conditions associated with campylobacteriosis or related sequelae. Thus, the methods of the present invention can be considered therapeutic methods, preventative and/or prophylactic methods. In a particular embodiment, it is contemplated herein that the immunogenic synthetic constructs and/or conjugates of the instant inventions may be administered to a subject and thus prevent diarrhea and/or other form of gastroenteritis caused by *C. jejuni* in the subject.

One of skill in the art will appreciate that the administration of the synthetic construct of the instant invention encompasses the use of the constructs and/or the compositions, e.g., vaccine formulations, of the instant invention to generate immunity in a subject if later challenged by infection with *C. jejuni*. It is further understood herein, however, that the synthetic constructs, conjugates, compositions, vaccine formulations and methods of the present invention do not necessarily provide total immunity to *C. jejuni* and/or totally cure or eliminate all disease symptoms.

Suitable effective amounts of the immunogenic synthetic constructs of the instant invention can be readily determined by those of skill in the art and will depend upon the age, weight, species (if non-human) and medical condition of the subject to be treated, and whether the construct is administered in a conjugated or unconjugated form. One of skill in the art will appreciate that doses may be determined empirically, and can also vary depending on the adjuvant used. For example, initial information may be gleaned in laboratory experiments, and an effective amount for humans subsequently determined through conventional dosing trials and routine experimentation.

As contemplated herein, in a particular embodiment an effective amount of the construct or conjugate for vaccination against *C. jejuni* infection may be from between about 1 µg or less to about 100 µg or more per kg body weight. As a general guide, a suitable amount of a construct or conjugate of the invention can be an amount between from about 0.1 µg to about 10 mg per dosage amount with or without an adjuvant. Moreover, immunization comprising administering one or more boosting doses may be performed using between from about 0.1 µg to about 10 mg per dose with or without adjuvant.

It is contemplated herein that the constructs and compositions of the instant invention may be administered to a subject by a variety of routes according to conventional methods, including but not limited to parenteral (e.g., by intracisternal injection and infusion techniques), intradermal, transmembranal, transdermal (including topical), intramuscular, intraperitoneal, intravenous, intra-arterial, intralesional, subcutaneous, oral, and intranasal (e.g., inhalation) routes of administration. Administration can also be by continuous infusion or bolus injection.

In addition, the compositions of the instant invention can be administered in a variety of dosage forms. These include, e.g., liquid preparations and suspensions, including preparations for parenteral, subcutaneous, intradermal, intramuscular, intraperitoneal or intravenous administration (e.g., injectable administration), such as sterile isotonic aqueous solutions, suspensions, emulsions or viscous compositions that may be buffered to a selected pH. In a particular embodiment, it is contemplated herein that the constructs and compositions of the instant invention are administered to a subject as an injectable, including but not limited to injectable compositions for delivery by intramuscular, intravenous, subcutaneous, or transdermal injection. Such compositions may be formulated using a variety of pharmaceutical excipients, carriers or diluents familiar to one of skill in the art.

In another particular embodiment, the synthetic immunogenic constructs and compositions of the instant invention may be administered orally. Oral formulations for administration according to the methods of the present invention may include a variety of dosage forms, e.g., solutions, powders, suspensions, tablets, pills, capsules, caplets, sustained release formulations, or preparations which are time-released or which have a liquid filling, e.g., gelatin covered liquid, whereby the gelatin is dissolved in the stomach for delivery to the gut. Such formulations may include a variety of pharmaceutically acceptable excipients familiar to one of skill in the art, including but not limited to mannitol, lactose, starch, magnesium stearate, sodium saccharine, cellulose, and magnesium carbonate.

In a particular embodiment, it is contemplated herein that a composition for oral administration may be a liquid formulation. Such formulations may comprise a pharmaceutically acceptable thickening agent which can create a composition with enhanced viscosity which facilitates mucosal delivery of the immunogen, e.g., by providing extended contact with the lining of the stomach. Such viscous compositions may be made by one of skill in the art employing conventional methods and employing pharmaceutical excipients and reagents, e.g., methylcellulose, xanthan gum, carboxymethyl cellulose, hydroxypropyl cellulose, and carbomer.

Other dosage forms suitable for nasal or respiratory (mucosal) administration, e.g., in the form of a squeeze spray dispenser, pump dispenser or aerosol dispenser, are contemplated herein. Dosage forms suitable for rectal or vaginal delivery are also contemplated herein. The constructs, conjugates, and compositions of the instant invention may also be lyophilized and may be delivered to a subject with or without rehydration using conventional methods.

As understood herein, the methods of the instant invention comprise administering the immunogenic synthetic construct to a subject according to various regimens, i.e., in an amount and in a manner and for a time sufficient to provide a clinically meaningful benefit to the subject. Suitable administration regimens for use with the instant invention may be determined by one of skill in the art according to conventional methods. For example, it is contemplated herein that an effective amount may be administered to a subject as a single dose, a series of multiple doses administered over a period of days, or a single dose followed by a boosting dose thereafter, e.g., several years later. The term "dose" or "dosage" as used herein refers to physically discrete units suitable for administration to a subject, each dosage containing a predetermined quantity of the synthetic construct and/or conjugate as the active pharmaceutical ingredient calculated to produce a desired response.

The administrative regimen, e.g., the quantity to be administered, the number of treatments, and effective amount per unit dose, etc. will depend on the judgment of the practitioner and are peculiar to each subject. Factors to be considered in this regard include physical and clinical state of the subject, route of administration, intended goal of treatment, as well as the potency, stability, and toxicity of the particular construct, conjugate or composition. As understood by one of skill in the art, a "boosting dose" may comprise the same dosage amount as the initial dosage, or a different dosage amount. Indeed, when a series of immunizations is administered in order to produce a desired immune response in the subject, one of skill in the art will appreciate that in that case, an "effective amount" may encompass more than one administered dosage amount.

As contemplated herein, the compositions of the instant invention, and particularly pharmaceutical compositions and vaccines of the instant invention, are preferably sterile and contain an amount of the construct and/or conjugate vaccine in a unit of weight or volume suitable for administration to a subject. The volume of the composition administered to a subject (dosage unit) will depend on the method of administration and is discernible by one of skill in the art. For example, in the case of an injectable, the volume administered typically may be between 0.1 and 1.0 ml, preferably approximately 0.5 ml.

As understood by one of skill in the art, the term "composition" as used herein encompasses pharmaceutical compositions. As understood herein, a "pharmaceutical composition" of the instant invention comprises an active agent, e.g., an immunogenic synthetic construct (unconjugated or conjugated to a carrier protein or combination thereof) or an antibody preparation, in combination with one or more pharmaceutically acceptable excipients, carriers, or diluents. The term "pharmaceutically acceptable" is used to refer to a non-toxic material that is compatible with a biological system such as a cell, cell culture, tissue, or organism.

Examples of pharmaceutically acceptable excipients, carriers and diluents are familiar to one of skill in the art and can be found, e.g., in *Remington's Pharmaceutical Sciences* (latest edition), Mack Publishing Company, Easton, Pa. For example, pharmaceutically acceptable excipients include, but are not limited to, wetting or emulsifying agents, pH buffering substances, binders, stabilizers, preservatives, bulking agents, adsorbents, disinfectants, detergents, sugar alcohols, gelling or viscosity enhancing additives, flavoring agents, and colors. Pharmaceutically acceptable carriers include macromolecules such as proteins, polysaccharides, polylactic acids, polyglycolic acids, polymeric amino acids, amino acid copolymers, trehalose, lipid aggregates (such as oil droplets or liposomes), and inactive virus particles. Pharmaceutically acceptable diluents include, but are not limited to, water, saline, and glycerol.

As understood by one of skill in the art, the type and amount of pharmaceutically acceptable additional components included in the pharmaceutical compositions of the instant invention may vary, e.g., depending upon the desired route of administration and desired physical state, solubility, stability, and rate of in vivo release of the composition. For example, for administration by intravenous, cutaneous, subcutaneous, or other injection, a vaccine formulation is typically in the form of a pyrogen-free, parenterally acceptable aqueous solution of suitable pH and stability, and may contain an isotonic vehicle as well as pharmaceutical acceptable stabilizers, preservatives, buffers, antioxidants, or other additives familiar to one of skill in the art.

In a particular embodiment, pharmaceutical compositions in the form of a vaccine formulation comprising the immunogenic synthetic constructs and/or conjugates of the instant invention, alone or in combination with other active agents and/or pharmaceutically acceptable excipients, are contemplated for administration to a subject as provided herein. Both monovalent vaccines (e.g., designed to immunize against a single antigen or single microorganism), and polyvalent (or multivalent) vaccines (e.g., designed to immunize against two or more strains of the same microorganism, or against two or more microorganisms) are contemplated herein. In one embodiment, a vaccine formulation of the instant invention is a polyvalent formulation. In a particular embodiment, the vaccine formulations of the instant invention may be a polyvalent formulation against one or more strains of C. jejuni, including but not limited to, serotypes HS 23/36, HS1, HS2, HS3, HS4, and HS5/31. It is also contemplated herein that a polyvalent formulation of the instant invention may be directed against one or more strains of C. jejuni and/or other bacterial strain including those which have MeOPN-containing capsules.

For example, data provided herein demonstrate that antibodies to HS23/36, HS4 and HS1 strains of C. jejuni can react with a synthetic MeOPN-6-Gal construct. Thus, in one embodiment, it is contemplated herein that one of skill in the art, using conventional methods and without undue experimentation, could develop a multivalent vaccine formulation comprising the synthetic MeOPN-6-Gal construct disclosed herein which should cover at least these three major capsule types of C. jejuni. It is contemplated herein that a multivalent synthetic construct comprising MeOPN-6-Gal may further include MeOPN-2-Gal and/or MeOPN-4-Gal moieties.

It is also contemplated that a multivalent vaccine formulation of the instant invention may comprise multiple synthetic constructs comprising one or more of the MeOPN moieties such as disclosed herein. Specifically, it is further contemplated herein that additional multivalent formulations comprising one or more immunogenic synthetic constructs of the instant invention could be developed which cover the strains of C. jejuni which account for a majority of worldwide cases of campylobacteriosis. Such formulations might be produced, for example, by synthesizing additional constructs comprising capsular monosaccharides from C. jejuni strains of relevance in this regard and testing such synthetic constructs for immunogenicity (including possible cross reactivity) against such strains of C. jejuni. In a particular embodiment, such synthetic constructs may comprise one or more monosaccharides comprising one or more MeOPN moieties including, e.g., one or more MeOPN-6-Gal moieties, one or more MeOPN-4-Gal moieties, and/or one or more MeOPN-2-Gal moieties. A synthetic construct comprising MeOPN-2-Gal is contemplated herein.

A multivalent vaccine formulation of the instant invention may comprise a single synthetic construct designed to cover more than one strain of C. jejuni, and/or may comprise a synthetic construct designed specifically against a single particular strain of C. jejuni. In addition, one of skill in the art will appreciate that synthetic constructs may be produced which are immunogenic not only against more than one strain of C. jejuni, but also against more than one type of bacterium, e.g., ETEC or Shigella, by chemically linking various different antigenic components against these additional bacteria to an immunogenic construct against C. jejuni. See, e.g., US 2015/0258201.

The formulation of the vaccines of the present invention can be accomplished using art recognized methods. For example, in addition to an immunologically effective amount of the construct or conjugate vaccine, a "vaccine formulation" of the instant invention may further comprise one or more non-immunogenic components, e.g., one or more pharmaceutically acceptable excipients, carriers, diluents, stabilizers, preservatives, buffers, and disinfectants as discussed above. To this end, one of skill in the art will appreciate that the development of a robust and stable vaccine formulation will ideally employ various excipients and formulation parameters that will provide stability to the antigen and thus prevent aggregation, loss of protein structure, and/or chemical degradation such as oxidation and deamidation. One of skill in the art using routine experimentation and conventional methods can determine the particular pH, buffers, and stabilizers that are well suited for the development of robust and stable vaccine formulations of the instant invention. See, e.g., Morefield, G. (2011) The APPS Journal, 13: 191-200.

In addition, the pharmaceutical compositions, and particularly the vaccine formulations of the instant invention, may further comprise an immune-effective amount of one or more adjuvants. As understood by one of skill in the art, an adjuvant is a substance that aids a subject's immune response to an antigen (i.e., a humoral and/or cell-mediated immune response). An adjuvant can be used to increase the immunogenic efficacy of a vaccine, and may also have the ability to increase the stability of a vaccine formulation. Thus, faster and longer lasting immune responses may be possible in viva through the addition of an adjuvant to a vaccine formulation. See, e.g., Stills, ILAR J (2005) 46:280-293, the contents of which are incorporated by reference herein.

As understood herein, an "immune-effective amount" of an adjuvant is understood as that amount which helps elicit an immune response to an antigen, e.g., by increasing the efficacy of a vaccine, and/or increasing the stability of a vaccine formulation. The amount required may vary depending on the adjuvant and the antigen, and may be discerned without undue experimentation by one of skill in the art.

Adjuvants suitable for use with the compositions of the instant invention are familiar to one of skill in the art and are available from a variety of commercial vendors. These include, for example, glycolipids; chemokines; compounds that induce the production of cytokines and chemokines; interferons; inert carriers, such as alum, bentonite, latex, and acrylic particles; pluronic block polymers; depot formers;

surface active materials, such as saponin, lysolecithin, retinal, liposomes, and pluronic polymer formulations; macrophage stimulators, such as bacterial lipopolysaccharide; alternate pathway complement activators, such as insulin, zymosan, endotoxin, and levamisole; non-ionic surfactants; poly(oxyethylene)-poly(oxypropylene) tri-block copolymers; trehalose dimycolate (TDM); cell wall skeleton (CWS); complete Freund's adjuvant; incomplete Freund's adjuvant; macrophage colony stimulating factor (M-CSF); tumor necrosis factor (TNF); 3-O-deacylated MPL; CpG oligonucleotides; polyoxyethylene ethers, polyoxyethylene esters, aluminum, Poly[di(carboxylatophenoxy)phosphazene] (PCPP), monophosphoryl lipid A, QS-21, cholera toxin and formyl methionyl peptide.

In one embodiment, the adjuvant may be selected from the group consisting of antigen delivery systems (e.g. aluminum compounds or liposomes), immunopotentiators (e.g. toll-like receptor ligands), or a combination thereof (e.g., AS01 or ASO4.) These substances are familiar to one of skill in the art. In a particular embodiment, an adjuvant for use in the compositions and methods of the instant invention is selected from the group consisting of toll-like receptor ligands, aluminum phosphate, aluminum hydroxide, monophosphoryl lipid A, liposomes, and derivatives and combinations thereof. See, e.g., Alving, C. et al., 2012, *Expert Rev Vaccines* 11, 733-44; Alving, C. et al. (2012) *Curr Opin Immunol* 24, 310-5; Alving C. and Rao, M, (2008) *Vaccine* 26, 3036-3045; U.S. Pat. Nos. 6,090,406; 5,916,588.

In addition to the immunogenic synthetic construct and/or conjugate, the compositions of the instant invention may further comprise one or more other active pharmaceutical ingredient, including but not limited to, additional immunoregulatory agents. As understood herein, an immunoregulatory agent is a substance that can induce, potentiate, activate or otherwise stimulate the immune system of the subject. These immunoregulatory agents include, for example, substances selected from the group consisting of antigens of one or more strains of *C. jejuni*, antigens of ETEC, *Shigella* lipopolysaccharide structures, and unconjugated carrier proteins. (See, e.g., US 2015/0258201 A1.) They may be used in immune-effective amounts easily discernable by one of skill in the art without undue experimentation.

In addition, the compositions and vaccines of the instant invention may be administered alone or in combination with other vaccines, and/or other therapeutic or immunoregulatory agents. Such additional vaccines and agents may be administered to a subject in any manner, e.g., before, after, or concurrently with the immunogenic synthetic constructs and compositions of the instant invention. They may be used in immune-effective/therapeutically effective amounts easily discernable by one of skill in the art without undue experimentation.

The immunogenic synthetic constructs described herein can be included in an immunogenic formulation (e.g., a vaccine formulation) against *C. jejuni* and administered to a subject for inducing an immune response against *C. jejuni*. Thus, the instant invention contemplates methods of inducing an immune response to *C. jejuni* in a subject, and particularly, methods of inducing an immune response in a subject that provides protective immunity from the gastrointestinal and other debilitating effects associated with *campylobacter* enteritis.

As an example, it is contemplated herein that a method of the instant invention comprises administering an immunogenic composition comprising one or more synthetic constructs of the instant invention, wherein the construct is optionally conjugated to a carrier molecule, preferably to a carrier protein molecule such as $CRM_{197}$. The method may further comprise one or more subsequent steps comprising administering one or more boosting doses of a composition comprising the same immunogen administered in the first step.

As understood by one of skill in the art, optimal methods for inducing protective immunity in humans are preceded by studies in animals such as in mice and monkeys. Thus, for each vaccine formulation comprising a synthetic construct of the instant invention, a limited amount of experimentation is required to ascertain the optimal effective dose ranges. For example, in one embodiment, it is contemplated herein that the range of a unit dose of immunogenic synthetic construct may be from about 0.1 μg to 10 mg per dose in a range of buffer solutions. Optionally, subsequent to a priming dose, one or more, e.g., 2 to 4 boosting doses may also be administered with a unit dose range of from about 0.1 μg to 10 mg of immunogen in a buffered aqueous solution.

Thus, a method of inducing an immune response in a subject against *C. jejuni* may comprise the steps of: (a.) administering an immunogenic composition comprising one or more synthetic constructs of the instant invention, wherein the construct is conjugated to a carrier molecule, preferably to a earlier protein molecule, and the composition administered at a dose range of 0.1 μg to 10 mg per dose with or without an adjuvant; and (b) optionally administering a boosting dose of the composition as described in step (a), with or without adjuvant, at a dose range of 0.1 μg to 10 mg per dose.

It is contemplated herein that depending on the route of administration, the vaccine formulation can be administered with or without any of a number of adjuvants such as those described herein. An immune-enhancing amount of adjuvant to be administered may vary depending on the particular adjuvant, and can be ascertained by one of skill in the art without undue experimentation.

Moreover, as discussed herein, the method may be performed using a synthetic construct that is conjugated to a carrier protein or using an unconjugated synthetic construct. The method may comprise the use of any of a number of carrier molecules discussed above. As an example, $CRM_{197}$ can be used. ETEC proteins may also be used as carrier proteins as discussed above, e.g., as disclosed in US 2015/0258201 A1.

The construct:carrier protein ratio (w/w) may be 1:1, or may be such that more than one construct is linked to a single carrier protein, e.g., from 2:1 to 10:1 or more; particularly, at least 8:1. As one of skill in the art will appreciate, a single carrier molecule may be conjugated to a large number of synthetic constructs, e.g., hundreds or even thousands of constructs per carrier molecule. An appropriate ratio best suited to inducing and/or enhancing an immune response in a subject may be discerned by one of skill in the art without undue experimentation.

Indeed, as contemplated herein, one of skill in the art could optimize the immunogenicity of a synthetic construct for use in the methods of the instant invention by using different combinations of synthetic constructs, including constructs and conjugates comprising more than one MeOPN modified monosaccharide, adjuvants, carrier proteins, additional immunoregulatory agents, and routes of administration. For example, it is contemplated herein that different ETEC proteins may be used in various combinations with the immunogenic synthetic constructs of the instant invention to produce a construct with enhanced immunogenicity, not only to *C. jejuni* but also to other bacterial pathogens. To this end, the teachings of US2015/0258201 A1 are incorporated by reference herein in its entirety. Moreover, a composition of the instant invention, e.g., pharmaceutical formulations, and particularly vaccine formulations of the instant invention can be administered in a variety of ways, e.g., orally, nasally, subcutaneously, intradermally, transdermally, transcutaneously intramuscularly, or rectally. Methods of administration and dosing regimens best suited to producing an immune response in a subject may be discerned by one of skill in the art using conventional methods and without undue experimentation.

The present invention further provides an antibody preparation against one or more MeOPN moieties found in the capsule of C. jejuni, including but not limited to MeOPN-2-Gal, MeOPN-4-Gal and MeOPN-6-Gal. In various embodiments, the antibody preparation may include any member from the group consisting of polyclonal antibody, monoclonal antibody, mouse monoclonal IgG antibody, humanized antibody, chimeric antibody, fragment thereof, or combination thereof. The invention further contemplates a hybridoma cell producing a monoclonal antibody directed against any of the MeOPN moieties described herein. In a particular embodiment, the invention is directed to a monoclonal antibody directed against MeOPN-2-Gal, MeOPN-4-Gal, or MeOPN-6-Gal.

In another embodiment, the present invention provides pharmaceutical compositions comprising one or more anti-MeOPN antibodies or functional fragments thereof, and a physiologically acceptable vehicle. In a particular embodiment, the invention provides a pharmaceutical composition comprising an antibody and a physiologically acceptable vehicle for use in a method for providing passive immunity or treatment against one or more C. jejuni serotypes. As used herein, "passive immunity" refers to the administration of antibodies to a subject, whereby the antibodies are produced in a different subject (including subjects of the same and different species) such that the antibodies attach to the surface of the bacteria and cause the bacteria to be phagocytosed or killed.

The pharmaceutical compositions and antibodies of the instant invention may be prepared by one of skill in the art using conventional methods. For example, antisera to one or more MeOPN moieties and/or synthetic constructs of the instant invention may be generated in New Zealand white rabbits by 3-4 subcutaneous injections over 13 weeks. A pre-immune bleed may generate about 5 mL of baseline serum from each rabbit. For example, a prime injection of antigen may be administered as an emulsion in complete Freund's adjuvant (CFA). Subsequent injections may be given at three week intervals in incomplete Freund's adjuvant (IFA). Rabbits may be bled every two weeks commencing one week after the third immunization. Approximately 25-30 mL of serum per rabbit may be generated from each bleeding event and frozen at −80° C. Serum may be analyzed by ELISA against the corresponding MeOPN/synthetic construct or purified polysaccharide capsule containing MeOPN using conventional methods. In addition, antisera from later bleeds may be affinity purified using conventional methods.

It is contemplated herein that the pharmaceutical antibody compositions of the instant invention may be used in a method for providing passive immunity against C. jejuni infections in a subject in need thereof. Thus, in a particular embodiment, the present invention includes methods of preventing, treating or ameliorating an infection by one or more strains or serotypes of C. jejuni in a subject by administering to the subject an effective amount of a pharmaceutical antibody composition of the instant invention. As understood herein, an effective amount may vary depending upon factors such as the subject's age, weight and species. In general, the dosage of antibody may be in a range from about 1-10 mg/kg body weight. In a particular embodiment, the antibody is a humanized antibody of the IgG or the IgA class.

One of skill in the art will appreciate that the administration of the pharmaceutical compositions and antibodies of the instant invention may be either prophylactic (prior to anticipated exposure to a C. jejuni infection) or therapeutic (after the initiation of the infection, e.g., at or shortly after the onset of symptoms.) Administration may include, e.g., oral or systemic methods, for example, subcutaneous, intramuscular or intravenous methods of administration discussed above.

The invention also provides a kit comprising immune-effective amounts of the immunogenic synthetic constructs and/or compositions of the instant invention. In a particular embodiment, the kit may comprise a conjugate vaccine and instructions for administering the conjugate vaccine to a subject. In another embodiment, the kit may comprise an antibody composition as described herein. The kit can optionally also contain effective amounts of one or more other therapeutic or immunoregulatory agents. The kit can optionally contain one or more diagnostic tools and instructions for use. For example, a composition comprising two or more vaccines can be included, or separate pharmaceutical compositions containing different vaccines, antibodies, or therapeutic agents. The kit can also contain separate doses of a conjugate vaccine and/or antibodies for serial or sequential administration. The kit can contain suitable delivery devices, e.g., syringes, inhalation devices, and the like, along with instructions for administrating the compositions. The kit can optionally contain instructions for storage, reconstitution (if applicable), and administration of any or all therapeutic agents included. The kits can include a plurality of containers reflecting the number of administrations to be given to a subject. If the kit contains a first and second container, then a plurality of these can be present.

Although the invention herein has been described with reference to particular embodiments, it is to be understood that these embodiments, and examples provided herein, are merely illustrative of the principles and applications of the present invention. It is therefore to be understood that numerous modifications can be made to the illustrative embodiments and examples, and that other arrangements can be devised without departing from the spirit and scope of the present invention as defined by the appended claims. All patent applications, patents, literature and references cited herein are hereby incorporated by reference in their entirety.

EXAMPLES

Example 1

Synthesis of p-Methoxyphenyl and Aminopentyl Glycosides of the MeOPN→6-Gal Construct: MeOPN→6-α-D-Galp-(1→OMP and MeOPN→6-β-D-Galp-(1→O(CH$_2$)$_5$NH$_2$ Previously, using conventional methods and mass spectrometry, we detected a non-stoichiometric MeOPN unit at the 2 position of galactose (MeOPN-2-Gal) in C. jejuni 81-176 CPS, with a $^{31}$P resonance similar to that depicted in FIG. 20A (peak Y) (Kanipes M I, et al. (2006.) *J. Bacteriol.*

188:3273-3279.) We confirmed this MeOPN-2-Gal linkage by NMR (FIG. 21A) through the detection of a cross-peak between the $^{31}$P resonance Y ($\delta_P$ 14.45) of MeOPN and H-2 ($\delta_H$ 4.52) of the galactose unit in a $^1$H-$^{31}$P correlation experiment. In some 81-176 CPS preparations, albeit of lower intensity, the $^{31}$P NMR spectrum displayed an additional resonance at $\delta_P$ 14.15 (designated peak Z) (FIG. 20B). A similar peak was also observed in another 81-176 CPS preparation (a mutant in gene CJJ81176_1420) that exhibited a cross-peak between the phosphorous of MeOPN and H-6 resonances of some of the CPS galactose units, which resonated very near the methyl resonances of MeOPN ($\delta_H$ 3.75 to 3.81) (FIG. 21B). The NMR data suggested that peak Z in 81-176 corresponded to a non-stoichiometric placement of MeOPN at position 6 of galactose (MeOPN-6-Gal.). These data and additional genetic studies are described in greater detail in Example 8 below.

In order to test the potential of a prototype synthetic monosaccharide anti-*C. jejuni* vaccine, p-methoxyphenyl and aminopentyl glycosides of MeOPN→6-Gal constructs, i.e., MeOPN→6-α-D-Galp-(1→OMP and MeOPN→6-β-D-Galp-(1→O(CH$_2$)$_5$NH$_2$, respectively, were synthesized. Specifically, as provided below and as depicted in FIG. 2 and FIG. 3, MeOPN→6-α-D-Galp construct may be synthesized as the p-methoxyphenyl (OMP) glycoside, MeOPN→6-α-D-Galp-(1→OMP (FIG. 2, Scheme 1) and then equipped with an aminopentyl linker at C-1 (as the β anomer) MeOPN→6-β-D-Galp-(1→O(CH$_2$)$_5$NH$_2$ for conjugation to a carrier protein (FIG. 3, Scheme 2.)

Figure 3:
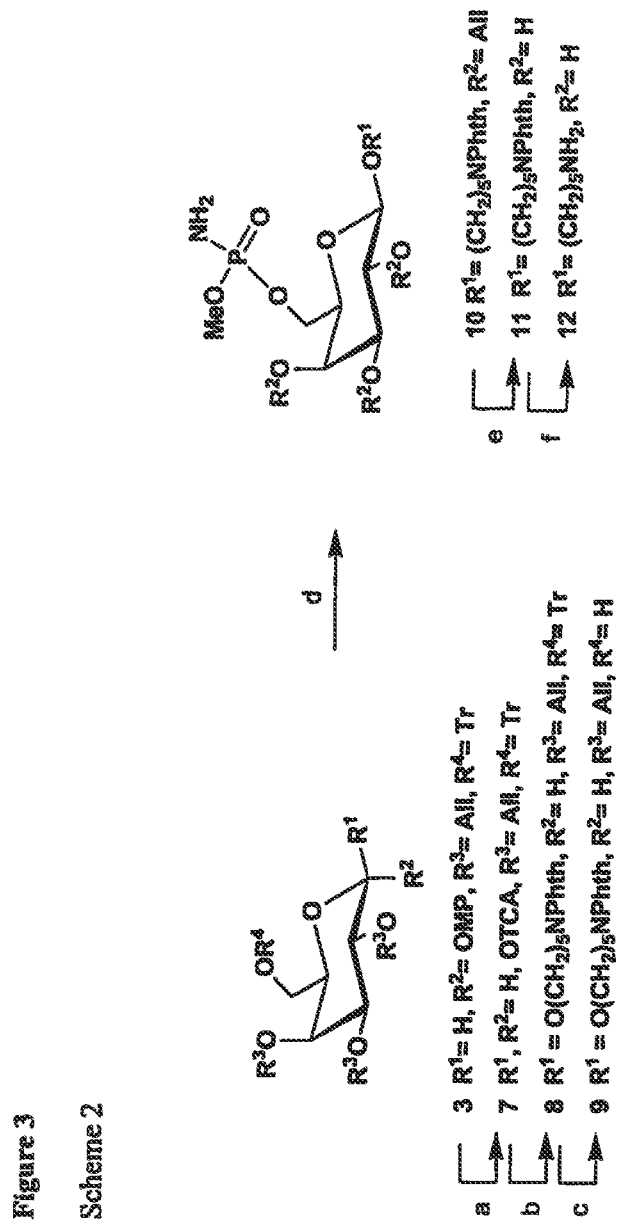
FIG. 3 depicts synthesis of the aminopentyl glycoside of the MeOPN→6-Gal construct (O-Me-phosphoramidate galactoside), MeOPN→6-β-D-Galp-(1→O(CH$_2$)$_5$NH$_2$ ("Scheme 2".) The reagents and conditions employed in the steps indicated therein are as follows: (a) CAN, $CH_3CN$, $H_2O$, 0° C.; then $CCl_3CN$, $K_2CO_3$, $CH_2Cl_2$, 57% over 2 steps; (b) HO(CH$_2$)$_5$NPhth, TMSOTf, $CH_2Cl_2$, 65%; (c) 80% AcOH, 80° C., 78%; (d) $PCl_2(O)OMe$, $Et_3N$, $CH_2Cl_2$, then $NH_{3(g)}$, 27%; (e) $PdCl_2$, MeOH, 75%, (f) $H_2NNH_2$, EtOH, 82%. CAN, cerium ammonium nitrate; TMSOTf, trimethylsilyl trifluoromethanesulfonate; Tr, trityl; All, allyl; OMP, 4-methoxyphenyl group; OTCA, trichloroacetimidate.

Summary Synthesis of MeOPN→6-α-D-Galp-(1→OMP (FIG. 2, Scheme 1)

Since MeOPN can be readily removed in mild acidic media, a suitable synthetic strategy circumventing such conditions was needed. As a starting compound, 4-methoxyphenyl-α-D-galactopyranoside was synthesized according to published methods. (See, Comfort, et al., *Biochem.* 46:3319-3330 (2007).) Briefly, 4-methoxyphenyl-α-D-galactopyranoside was synthesized from D-galactose by acetylation, glycosidation with 4-methoxyphenol, followed by Zemplén deacetylation according to published methods. (Montgomery et al, (1942) *J. Am. Chem. Soc.* 64, 690-694).

Starting from 4-methoxyphenyl-α-D-galactopyranoside (compound 1), a trityl group was selectively introduced to the 6-position. Originally, benzoylation was performed on compound 2, but the extensive migration observed during the introduction of MeOPN required the elucidation of a more suitable protecting group. Allyl groups were thus selected to protect the C-2, C-3 and C-4 positions which were resistant to migration. The allyl groups were later deprotected with catalytic hydrogenolysis, yielding compound 3, which proved to be compatible with the MeOPN modification. Next, the trityl group was removed giving compound 4 exposing 6-OH for modification.

The strategy for the introduction of MeOPN is similar to a published reaction. (See Mara et al, *Bioorg. Med. Chem. Lett.* 6180-6183 (2011.) Compound 4 was treated with commercially available methyl dichlorophosphate in the presence of triethyl amine, followed by ammonolysis. Due to the dual chiral nature of the newly introduced MeOPN, product 5 was collected as a mixture of two diastereoisomers. $^{31}$P NMR was able to confirm that product 5 was indeed a 1:1 mixture of two diastereoisomers, revealing two phosphorus signals at 10.5 ppm. $^1$H NMR also revealed two sets of signals with two anomeric and two OCH$_3$ signals (data not shown.)

Figure 13A:
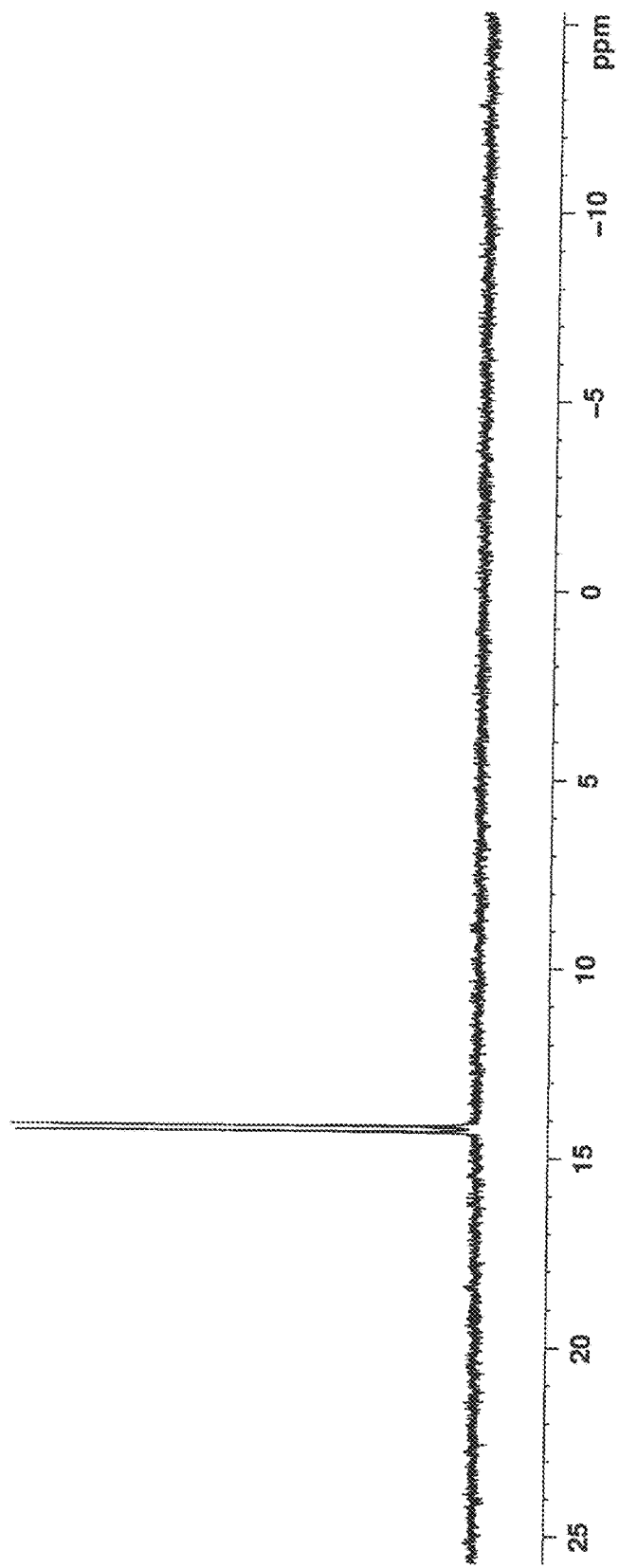
FIG. 13A depicts $^{31}$P NMR spectra and FIG. 13B depicts the $^1$H NMR (B) spectra of MeOPN→6-α-D-Galp-(1→OMP performed using conventional methods.
Figure 13B:
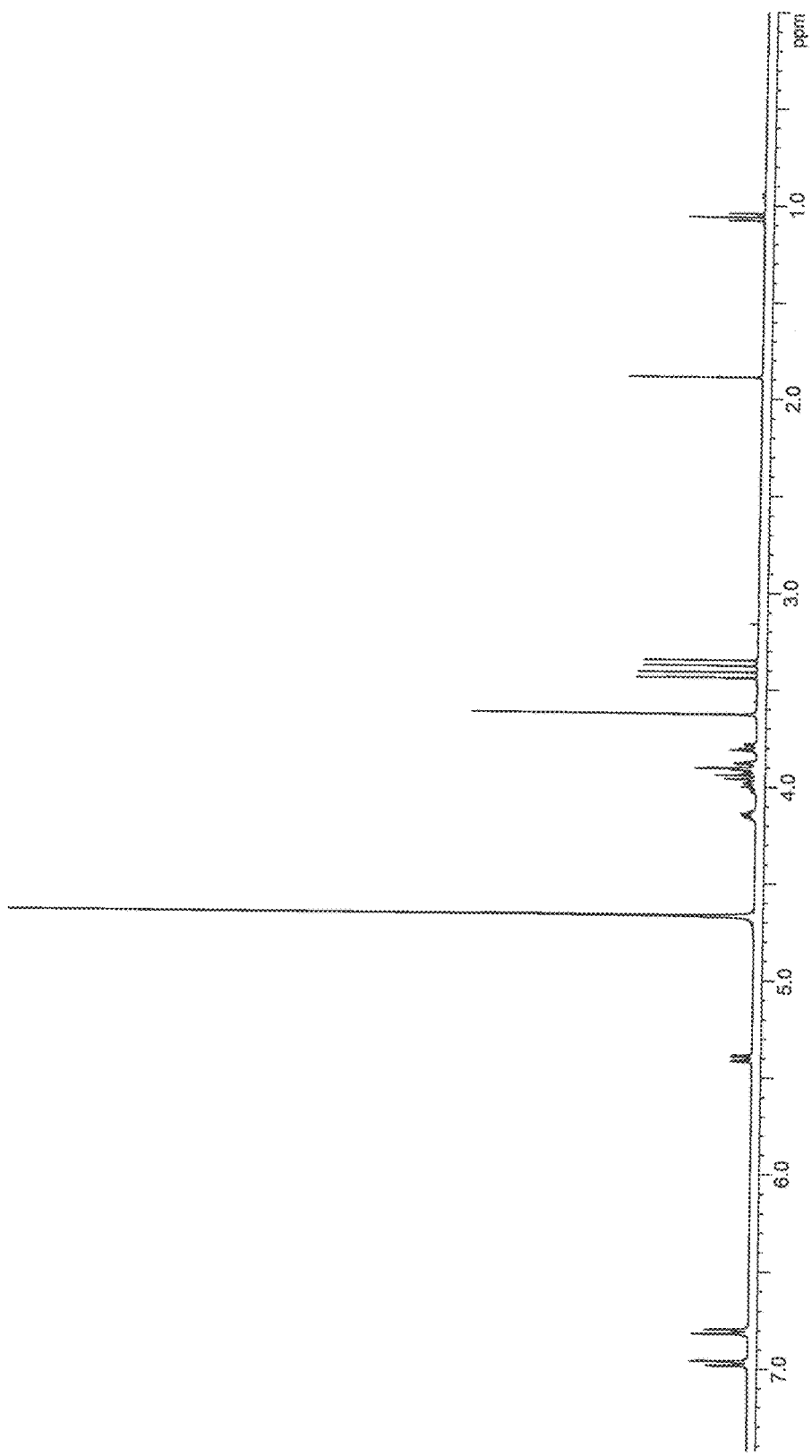

The reaction yielded a mixture of side products, the most abundant being the replacement of the O-methyl group by a second NH$_2$. Removal of the allyl group with palladium (II) chloride generated product 6. Similar to compound 5, a mixture of diastereoisomers was observed by $^1$H and $^{31}$P NMR. See FIG. 13 which depicts $^{31}$P NMR (A) and $^1$H NMR (B) spectra of MeOPN→6-α-D-Galp-(1→OMP performed using conventional methods.

A 2D $^1$H-$^{31}$P HMBC NMR experiment was able to confirm that the MeOPN was introduced to the O-6 position, showing correlation signals between phosphorous with both H-6 signals and OCH$_3$.

Summary Synthesis of MeOPN→6-β-D-Galp-(1→O(CH$_2$)$_5$NH$_2$ (FIG. 3, Scheme 2)

After successfully designing a strategy for the MeOPN modification, the construct was joined to a linker in order to make a vaccine conjugate. First, the 4-methoxyphenyl (OMP) was removed from galactoside (compound 3 in FIG. 2.) The corresponding hemiacetal was converted into the trichloroacetimidate donor (compound 7). The 5-amino-N-phthalimido-pentanyl linker was then introduced with TMSOTf as the activator at 0° C. Compound 8 was collected with 65% in the β and 29% in the α anomer. The removal of trityl group afforded compound 9 with a free hydroxyl group for the introduction of MeOPN. Using the procedure described above, phosphoramidate (compound 10) was collected as a mixture of two diastereoisomers. Allyl and phthalimido protecting groups were subsequently removed giving compound 11 and then compound 12.

Materials and Methods:

The compounds were synthesized using conventional methods and all chemicals were purchased from commercial suppliers and used as received. Molecular sieves were activated by heating with a heating mantle under reduced pressure. Thin layer chromatography (TLC) was carried out on TLC silica gel F$_{254}$. Sugar compounds were visualized by UV light or by charring with 10% H$_2$SO$_4$ in ethanol. Flash chromatography was performed with silica gel P60, (43-60 μm, 230-400 mesh.) $^1$H NMR and $^{13}$C NMR spectra were recorded with Bruker 400 or 600 MHz spectrometers (Bruker Daltonics Inc, Billerica, Mass.) The proton signal of residual, non-deuterated solvent (δ 7.24 ppm for CHCl$_3$) was used as internal reference for $^1$H spectra. For $^{13}$C spectra, the chemical shifts are reported relative to the solvent (δ 77.1 ppm for CDCl$_3$.) Chemical shifts are reported in parts per million (ppm.) Coupling constants are reported in Hertz (Hz.) The following abbreviations are used to indicate the multiplicities; s, singlet; d, doublet; t, triplet; m, multiplet. Optical rotations were measured on a Rudolph Research Autopol III automatic polarimeter (Rudolph Research Analytical, Hackettstown, N.J.) and concentration (c) is expressed in g/100 ml. High-resolution mass spectra for the synthetic compounds were recorded by electron spray ionization mass spectroscopy (time of flight analyzer.)

4-Methoxyphenyl 6-O-trityl-α-D-galactopyranoside (Compound 2)

To a solution of compound 1 (2.7 g, 9.3 mmol) dissolved in pyridine (40 mL), trityl chloride (3.1 g, 11 mmol) was added and the reaction mixture was stirred at 60° C. for 3 days. The reaction mixture was then concentrated and purified with flash chromatography (1:1 EtOAc-hexanes) to yield compound 2 (4.7 g, 95%.) $^1$H NMR (400 MHz, CDCl$_3$): δ 7.44-7.20 (m, 15H, Ar—H); 7.11-6.83 (m, 4H, MeOC$_6$H$_4$); 5.51 (d, 1H, J=3.6 Hz, H-1); 4.05-3.93 (m, 4H, H-2, H-3, H-4, H-5); 3.79 (s, 3H, OCH$_3$); 3.54-3.32 (m, 2H, H-6.) $^{13}$C NMR (100 MHz, CDCl$_3$): δ 155.3, 151.2, 150.6, 144.3, 143.8, 143.7, 143.6, 129.1, 128.6, 128.0, 127.9, 127.8, 127.5, 127.3, 127.1, 127.0, 118.5, 117.9, 114.6, 114.5, 114.4 (Ar); 98.4 (C-1); 87.0, 71.2, 70.0, 69.3 (C-2, C-3, C-4, C-5); 63.6 (C-6); 55.6 (CH$_3$.) HRMS (ESI): Calcd. For C$_{32}$H$_{32}$O$_7$ [M+Na]$^+$: 551.2046, found: 551.2021.

4-Methoxyphenyl 2,3,4-tri-O-allyl-6-O-trityl-α-D-galactopyranoside (Compound 3)

A solution of compound 2 (4.7 g, 8.8 mmol) dissolved in DMF (60 mL) with allyl bromide (4.6 mL, 53 mmol) was cooled to 0° C. Sodium hydride, 60% dispersion in mineral oil (1.2 g, 29 mmol) was added and the reaction mixture was stirred for 1 h at 0° C. The reaction was then quenched with MeOH (10 mL), poured into ice-cold water (100 mL) and extracted with EtOAc (3×100 mL.) The organic layer was dried over Na$_2$SO$_4$ and concentrated. Purification by flash chromatography eluting with 1:7 EtOAc-hexanes gave compound 3 (5.1 g, 89%.) [α]$_D^{25}$=+132.6° (c+0.1, CHCl$_3$); $^1$H NMR (400 MHz, CDCl$_3$): δ 7.38-7.18 (m, 15H, Ar—H); 7.10-6.75 (m, 4H, MeOC$_6$H$_4$); 6.00-5.53 (m, 3H, CH$_2$—CH=CH$_2$); 5.42 (d, 1H, J=3.2 Hz, H-1); 5.33-4.98 (m, 6H, CH$_2$—CH=CH$_2$); 4.37-3.72 (m, 13H, CH$_2$—CH=CH$_2$, H-2, H-3, H-4, H-5, OCH$_3$); 3.38 (m, 1H, H-6a); 3.01 (m, 1H, H-6b.) $^{13}$C NMR (100 MHz, CDCl$_3$): δ 155.0, 151.0, 143.9 (Ar); 135.2, 135.1, 135.0 (CH$_2$—CH=CH$_2$); 128.6, 127.8, 127.0, 119.0, 117.4, 117.3, 116.4, 114.4 (CH$_2$—CH=CH$_2$, Ar); 97.5 (C-1); 86.8; 78.2 (C-2); 77.4 (C-4); 76.1 (C-5); 73.9, 72.5, 71.9 (CH$_2$—CH=CH$_2$); 70.4 (C-3) 63.3 (C-6); 55.6 (OCH$_3$.) HRMS (ESI): Calcd. For C$_{41}$H$_{44}$O$_7$ [M+Na]$^+$; 671.2985, found: 671.2970.

4-Methoxyphenyl 2,3,4-tri-O-allyl-α-D-galactopyranoside (Compound 4)

A solution of compound 3 (300 mg, 0.46 mmol) in 80% aqueous AcOH (5 mL) was stirred at 80° C. for 1.5 h. The reaction mixture was concentrated before purification by flash chromatography (1:6 EtOAc-hexanes) giving compound 4 (147 mg, 78%.) $^1$H NMR (400 MHz, CDCl$_3$): δ 7.02-6.78 (m, 4H, MeOC$_6$H$_4$); 5.95-5.89 (m, 3H, CH$_2$—CH=CH$_2$); 5.50 (d, 1H, J=3.5 Hz, H-1); 5.35-5.12 (m, 6H, CH$_2$—CH=CH$_2$); 4.42 (dd, 1H, J$_1$=3.2 Hz, J$_2$=9.3 Hz, H-3); 4.27-3.89 (m, 10H, CH$_2$—CH=CH$_2$, H-2, H-4, H-5, OH); 3.81 (m, 1H, H-6a); 3.74 (s, 3H, OCH$_3$); 3.70 (m, 1H, H-6b.) $^{13}$C NMR (100 MHz, CDCl$_3$): δ 155.1, 150.9 (Ar); 135.0, 134.9 (CH$_2$—CH=CH$_2$); 118.6, 118.0, 117.4, 116.6, 114.5 (CH$_2$—CH=CH$_2$, Ar); 97.5 (C-1); 78.2, 75.9, 74.0, 72.6, 72.0, 71.0 (CH$_2$—CH=CH$_2$, C-2, C-3, C-4, C-5); 62.7 (C-6); 55.6 (OCH$_3$.) HRMS (ESI): Calcd. For C$_{22}$H$_{30}$O$_7$ [M+Na]$^+$: 429.1890, found: 429.1891.

4-Methoxyphenyl 2,3,4-tri-O-allyl-6-O-methyl-phosphramidate-α-D-galactopyranoside (Compound 5)

To a solution of compound 4 (65 mg, 0.16 mmol) and methyl dichlorophosphate (150 μL, 1.3 mmol) dissolved in CH$_2$Cl$_2$ (3 mL) with molecular sieves, Et$_3$N (175 μL, 1.3 mmol) was added drop-wise. The reaction mixture was stirred at room temperature for 5 hours. Upon completion of the reaction as judged by TLC, ammonia gas was injected into the reaction mixture through a needle. After 10 min, the reaction mixture was filtered and concentrated. Purification with column chromatography (1:1 EtOAc-hexanes) yielded compound 5 (15 mg, 19%.) $^1$H NMR (400 MHz, CDCl$_3$): δ 7.04-6.77 (m, 4H, MeOC$_6$H$_4$); 5.99-5.85 (m, 3H, CH$_2$—CH=CH$_2$); 5.48 (2d, 1H, J=3.6 Hz, H-1); 5.36-5.10 (m, 6H, CH$_2$—CH=CH$_2$); 4.41 (m, 1H, H-3); 4.29-4.10 (m, 8H, CH$_2$—CH=CH$_2$, H-2, H-4); 3.95-3.86 (m, 3H, H-5, H-6); 3.73 (s, 3H, OCH$_3$); 3.57 (2d, 3H, J=11.4 Hz, OCH$_3$); 2.75, 2.56 (2d, 2H, NH$_2$.) $^{13}$C NMR (100 MHz, CDCl$_3$): δ 155.2, 155.0, 150.9 (Ar); 135.0, 134.9 (CH$_2$—CH=CH$_2$); 128.9, 128.3, 118.8, 118.5, 117.7, 117.5, 117.4, 116.6, 114.5, 114.4 (CH$_2$—CH=CH$_2$, Ar); 97.6, 97.2 (C-1); 78.1, 75.8, 74.4, 74.0, 72.7, 71.9, 70.5, 70.4, 70.0, 69.9, 68.5, 65.5, (CH$_2$—CH=CH$_2$, C-2, C-3, C-4, C-5, C-6); 55.7, 53.3, 53.2 (OCH$_3$.) HRMS (ESI): Calcd. For C$_{23}$H$_{34}$NO$_9$P [M+H]$^+$: 500.2050, found: 500.2035.

4-Methoxyphenyl 6-O-methyl-phosphoramidate-α-D-galactopyranoside (Compound 6)

To a solution of compound 5 (17.0 mg) dissolved in MeOH (1 mL), PdCl$_2$ (5.0 mg) was added and the reaction mixture was stirred at room temperature for 3 h. The reaction mixture was then filtered and concentrated. Purification with column chromatography (pure EtOAc) yielded compound 6 (5.1 mg, 39%.) $^1$H NMR (400 MHz, D$_2$O): δ 6.98-6.80 (m, 4H, MeOC$_6$H$_4$); 5.39 (2d, 1H, J=3.6 Hz, H-1); 4.13 (m, 1H, H-3); 4.01-3.85 (m, 4H, H-4, H-5, H-6); 3.78 (m, 1H, H-2); 3.63 (OCH$_3$); 3.41 (2d, 3H, J=11.4 Hz, OCH$_3$.) $^{13}$C NMR (100 MHz, D$_2$O): δ 154.6, 150.0, 149.9, 119.3, 119.1, 114.9 (Ar); 98.1, 97.9 (C-1); 70.3, 70.2, 70.0, 69.1, 68.8, 67.8, 65.8 (C-2, C-3, C-4, C-5, C-6); 55.6 (OCH$_3$); 53.6, 53.5, 53.4 (OCH$_3$.) HRMS (ESI): Calcd. For C14H23NO9P [M+H]$^+$ cal. 380.1111, found 380.1110.

2,3,4-Tri-O-allyl-6-O-trityl-α,β-D-galactopyranosyl trichloroacetimidate (Compound 7)

To a solution of compound 3 (5.0 g, 7.7 mmol) dissolved in CH$_3$CN (480 mL) and H$_2$O (120 mL), cerium ammonium nitrate (12.8 g, 23 mmol) was added and the reaction mixture was stirred for 20 min at 0° C. The mixture was then diluted with brine (200 mL) and extracted with EtOAc (3×300 mL.) The organic layer was washed with saturated aq. Na$_2$CO$_3$ and water, dried over Na$_2$SO$_4$, concentrated and purified with column chromatography (1:6 EtOAc-hexanes.) The resulting hemiacetal (3.3 g, 6.1 mmol) was dissolved in anhydrous CH$_2$Cl$_2$ (120 ml) and CCl$_3$CN (310 μL, 30 mmol) and K$_2$CO$_3$ (420 mg, 30 mmol) were added. The reaction mixture was stirred at room temperature overnight before it was filtered through Celite® and concentrated. Purification with flash chromatography (1:4 EtOAc-hexanes with 1% Et$_3$N by volume) gave compound 7 as an α,β-mixture (3.6 g, 57% over 2 steps) (compounds 7A and 7B.)

7A: $^1$H NMR (400 MHz, CDCl$_3$): δ 8.52 (s, 1H, NH); 7.42-7.18 (m, 15H, Ar—H); 6.46 (d, 1H, J=3.6 Hz, H-1); 6.00-5.61 (m, 3H, CH$_2$—CH=CH$_2$); 5.39-4.98 (m, 6H, CH$_2$—CH=CH$_2$); 4.32-3.84 (m, 10H, CH$_2$—CH=CH$_2$, H-2, H-3, H-4, H-5); 3.35 (m, 1H, H-6a); 3.09 (m, 1H, H-6b); $^{13}$C NMR (100 MHz, CDCl$_3$): δ 161.3, 160.8, 143.9, 143.7, 135.2, 135.0, 134.9, 134.8, 134.1, 133.8, 128.8, 128.6, 127.8, 127.1, 127.0 (Ar, CH$_2$—CH=CH$_2$); 117.9, 117.4, 117.3, 116.7, 116.5 (CH$_2$—CH=CH$_2$); 104.0 (C-1); 86.8 (C-3); 86.7 (C-2); 83.8 (C-3); 82.6 (C-4); 76.7 (C-4); 75.3, 74.1, 72.5, 72.2, 71.8, 71.0 ($CH_2$—CH=$CH_2$, C-5); 61.9 (C-6.) HRMS (ESI): Calcd. For $C_{36}H_{38}Cl_3NO_6$ [M+Na]$^+$: 708.1663, found: 708.1673.

7B: $^1$H NMR (400 MHz, CDCl$_3$): δ 8.59 (s, 1H, NH); 7.41-7.18 (m, 15H, Ar—H); 5.90 (m, 2H, $CH_2$—CH=$CH_2$); 5.62 (m, 2H, H-1, $CH_2$—CH=$CH_2$); 5.35-5.01 (m, 6H, $CH_2$—CH=$CH_2$); 4.31-3.83 (m, 6H $CH_2$—CH=$CH_2$); 3.83 (m, 1H, H-5); 3.76 (dd, 1H, $J_1$=8.2 Hz, $J_2$=9.7 Hz, H-3); 3.62 (t, 1H, J=5.9 Hz, H-2), 3.48-3.39 (m, 2H, H-4, H-6a); 3.12 (dd, 1H, $J_1$=7.2 Hz, $J_2$=9.3 Hz, H-6b.) $^{13}$C NMR (100 MHz, CDCl$_3$): δ 161.5, 143.8 (Ar); 135.4, 134.9, 134.8 ($CH_2$—CH=$CH_2$); 128.7, 128.6, 128.0, 127.9, 127.1 (Ar); 117.3, 117.0, 116.8 ($CH_2$—CH=$CH_2$); 98.5 (C-1); 86.8 (C-2); 81.6 (C-3); 77.8 (C-5); 74.6 (C-3) 74.2, 73.8, 73.3, 72.0 ($CH_2$—CH=$CH_2$, C-4); 62.4 (C-6.) HRMS (ESI): Calcd. For $C_{36}H_{38}Cl_3NO_6$ [M+Na]$^+$: 708.1663, found: 708.1673.

5-Amino-N-phthalimido-pentanyl2,3,4-tri-O-allyl-6-O-trityl-β-D-galactopyranoside (Compound 8)

Trichloroacetimidate (compound 7, both anomers) (1.1 g, 1.6 mmol) and 5-amino-N-phthalimido-pentanol (560 mg, 2.4 mmol) were dissolved in anhydrous CH$_2$Cl$_2$ (25 mL) and the reaction mixture was cooled to 0° C. TMSOTf (15 μL, 0.080 mmol) was added drop-wise and the reaction mixture was stirred for 15 min at 0° C. The reaction was then neutralized with Et$_3$N (15 μL) and concentrated. Purification with flash chromatography (1:8 EtOAc-hexanes) gave compound 8 (783 mg, 65%.) $^1$H NMR (400 MHz, CDCl$_3$): δ 7.80-7.67 (m, 4H, phthalimido protons); 7.41-7.19 (m, 15H, Ar—H); 5.98-5.59 (m, 3H, $CH_2$—CH=$CH_2$), 5.33-4.94 (m, 6H, $CH_2$—CH=$CH_2$); 4.30-3.84 (m, 8H, $CH_2$—CH=$CH_2$, H-1, linker-CHH); 3.77 (d, 1H, J=2.9 Hz, H-5); 3.62 (t, 2H, J=7.3 Hz, linker-CH$_2$); 3.45-3.35 (m, 4H, H-2, H-4, H-6a, linker-CHH); 3.29 (dd, 1H, $J_1$=3.0 Hz, $J_2$=9.8 Hz, H-3); 3.13 (dd, 1H, $J_1$=9.4 Hz, $J_2$=10.1 Hz, H-6b); 1.65 (m, 4H, linker-CH$_2$); 1.40 (m, 2H, linker-CH$_2$.) $^{13}$C NMR (100 MHz, CDCl$_3$); 168.4, 143.8 (Ar); 135.7, 135.3, 135.2 ($CH_2$—CH=$CH_2$); 133.9, 132.1, 128.7, 127.9, 127.1, 123.2 (Ar); 116.8, 116.5 ($CH_2$—CH=$CH_2$); 103.7 (C-1); 86.8; 81.5 (C-1); 79.2 (C-2); 73.9, 73.6, 73.4, 73.3 (C-5, C-4, $CH_2$—CH=$CH_2$); 71.9, 69.4 (linker); 62.5 (C-6); 37.9, 29.2, 28.4, 23.4 (linker.) HRMS (ESI): Calcd. For $C_{47}H_{51}NO_8$ [M+Na]$^+$: 780.3513, found 780.3489.

5-Amino-N-phthalimido-pentanyl 2,3,4-tri-O-allyl-β-D-galactopyranoside (Compound 9)

A solution of compound 8 (493 mg, 0.65 mmol) dissolved in 80% aqueous AcOH (10 mL) was stirred at 80° C. for 1 h. The reaction mixture was concentrated before purification by flash chromatography (1:1 EtOAc-hexanes) giving compound 9 (260 mg, 78%.) $^1$H NMR (400 MHz, CDCl$_3$): δ 7.81-7.66 (m, 4H, phthalimido protons); 5.92-5.82 (m, 3H, $CH_2$—CH=$CH_2$); 5.30-5.10 (m, 6H, $CH_2$—CH=$CH_2$); 4.37-4.02 (m, 6H, $CH_2$—CH=$CH_2$); 4.22 (d, 1H, J=7.7 Hz, H-1); 3.88 (m, 2H, H-6a, linker-CHH); 3.69-3.60 (m, 4H, H-4, H-6b, linker-CH$_2$); 3.51-3.42 (m, 2H, H-2, linker-CHH); 3.39 (m, 1H, H-5); 3.28 (dd, 1H, $J_1$=3.0 Hz, $J_2$=9.8 Hz, H-3); 2.09 (m, 1H, 6-OH); 1.65 (m, 4H, linker-CH$_2$); 1.40 (m, 2H, linker-CH$_2$.) $^{13}$C NMR (100 MHz, CDCl$_3$): δ 168.5 (phthalimido C=O); 135.3, 135.0, 133.9 ($CH_2$—CH=$CH_2$); 132.1, 123.2 (phthalimido); 117.8, 116.7, 116.6 ($CH_2$—CH=$CH_2$); 103.9 (C-1); 81.6 (C-3); 79.1 (C-2); 74.6 (C-5) 74.0 (C-4); 73.7, 73.6 ($CH_2$—CH=$CH_2$); 72.1, 69.6 (linker); 62.5 (C-6); 37.8, 29.2, 28.3, 23.3 (linker.) HRMS (ESI): Calcd. For $C_{28}H_{37}NO_8$ [M+Na]$^+$: 538.2417, found 538.2403.

5-Amino-N-phthalimido-pentanyl2,3,4-tri-O-allyl-6-O-methylphosphramidate-β-D-galactopyranoside (Compound 10)

To a solution of compound 9 (400 mg, 0.78 mmol) and methyl dichlorophosphate (0.70 mL, 6.0 mmol) dissolved in CH$_2$Cl$_2$ (15 mL) with molecular sieves, Et$_3$N (0.70 mL, 5.0 mmol) was added drop-wise. The reaction mixture was stirred at room temperature for 12 hours. Upon completion of the reaction as judged by TLC, ammonia gas was injected into the reaction mixture through a needle. After 10 min, the reaction mixture was filtered and concentrated. Purification with column chromatography (9:1 EtOAc-MeOH) yielded compound 10 (129 mg, 27%.) $^1$H NMR (400 MHz, CDCl$_3$): 7.80-7.68 (phthalimido protons); 5.88 (m, 3H, $CH_2$—CH=$CH_2$); 5.30-5.10 (m, 6H, $CH_2$—CH=$CH_2$); 4.23-4.10 (m, 9H, $CH_2$—CH=$CH_2$, H-1, linker-CH$_2$); 3.82 (m, 1H, H-5); 3.71-3.39 (m, 9H, OCH$_3$, H-4, H-2, H-6a, H-6b, linker-CH$_2$); 3.28 (m, 1H, H-3); 2.87 (dd, 2H, $J_1$=5.3 Hz $J_2$=13.0 Hz, NH$_2$); 1.66 (m, 4H, linker-CH$_2$); 1.38 (m, 2H, linker-CH$_2$.) $^{13}$C NMR (100 MHz, CDCl$_3$): δ 168.5 (Ar); 135.4, 135.2, 134.9 ($CH_2$—CH=$CH_2$); 133.9, 132.1, 123.2 (Ar); 117.5, 117.2, 116.8, 116.7, 116.6 ($CH_2$—CH=$CH_2$); 103.8 (C-1); 81.4 (C-3); 78.9 (C-2); 74.0, 73.8, 73.3, 73.2, 73.0, 72.9, 72.1 ($CH_2$—CH=$CH_2$, C-5, C-4); 69.8, 69.7 (C-6) 65.3; 65.0, 64.9 (linker) 53.4, 53.3 (OCH$_3$); 37.9, 29.7, 29.2, 28.3 (linker.) HRMS (ESI): Calcd. For $C_{29}H_{41}N_2O_{10}P$ [M+H]$^+$: 609.2578, found 609.2585.

5-Amino-N-phthalimido-pentanyl6-O-methylphosphramidate-β-D-galactopyranoside (Compound 11)

To a solution of compound 10 (95 mg, 0.16 μmol) dissolved in MeOH (4 mL), PdCl$_2$ (20 mg) was added and the reaction mixture was stirred at room temperature for 4 h. The reaction mixture was then filtered and concentrated. Purification with column chromatography (9:1 EtOAc-MeOH) gave compound 11 (57 mg, 75%.) $^1$H NMR (400 MHz, D$_2$O): δ 7.64 (m, 4H, phthalimido protons); 4.23 (d, 1H, J=8.0 Hz, H-1); 4.01 (m, 2H, H-6); 3.78-3.70 (m, 3H, H-4, H-5, linker-CHH)); 3.59-3.45 (m, 7H, OCH$_3$, linker-CH$_2$ linker-CHH, H-3); 3.33 (dd, 1H, $J_1$=8.0 Hz, $J_2$=9.8 Hz, H-2); 1.51 (m, 4H, linker-CH$_2$); 1.22 (m, 2H, linker-CH$_2$.) $^{13}$C NMR (100 MHz, D$_2$O): 170.9, 134.5, 133.9, 131.3, 126.0, 123.1 (Ar); 102.6 (C-1); 73.2 (C-5); 72.5 (C-3); 71.9 (C-2); 70.3, 70.2 (linker); 68.1 (C-4); 65.4 (C-6); 53.6 (OCH$_3$); 48.7; 37.6 (linker); 28.2; 27.2, 22.3 (linker.) HRMS (ESI): Calcd. For $C_{20}H_{29}N_2O_{10}P$ [M+H]$^+$; 489.1639, found 489.1624.

5-Amino-pentanyl 6-O-methylphosphramidate-β-D-galactopyranoside (Compound 12)

To a solution of compound 11 (23 mg, 0.047 μmol) dissolved in 95% EtOH (1 mL), hydrazine monohydrate (16 μL, 0.33 μmol) was added and the reaction mixture was stirred at room temperature overnight. The reaction mixture was then concentrated and purification with column chromatography (3:1 EtOAc-MeOH) gave compound 12 (14 mg, 82%.) $^1$H NMR (400 MHz, D$_2$O): δ 4.27 (d, 1H, J=7.1 Hz, H-1); 4.03 (m, 2H, linker-CH$_2$); 3.81-3.75 (m, 3H, H-4, H-5, H-6a); 3.61-3.48 (m, 5H, OCH$_3$, H-3, H-6b); 3.36 (dd, 1H, $J_1$=7.9, $J_2$=9.9 Hz, H-2); 2.82 (t, 2H, J=7.5 Hz, linker-$CH_2$); 1.52 (m, 4H, linker-$CH_2$); 1.30 (m, 2H, linker-$CH_2$.) $^{13}C$ NMR (100 MHz, $D_2O$): δ 102.6 (C-1); 73.2 (C-5); 72.5 (C-3); 70.5 (C-2); 70.1 (C-6); 68.1 (C-4); 60.0 (linker); 48.7 ($OCH_3$); 39.2, 28.0, 26.3, 22.0, 21.9 (linker.) HRMS (ESI): Calcd. For $C_{12}H_{27}N_2O_8P$ [M+H]$^+$: 359.1584, found 359.1587.

Figure 4:
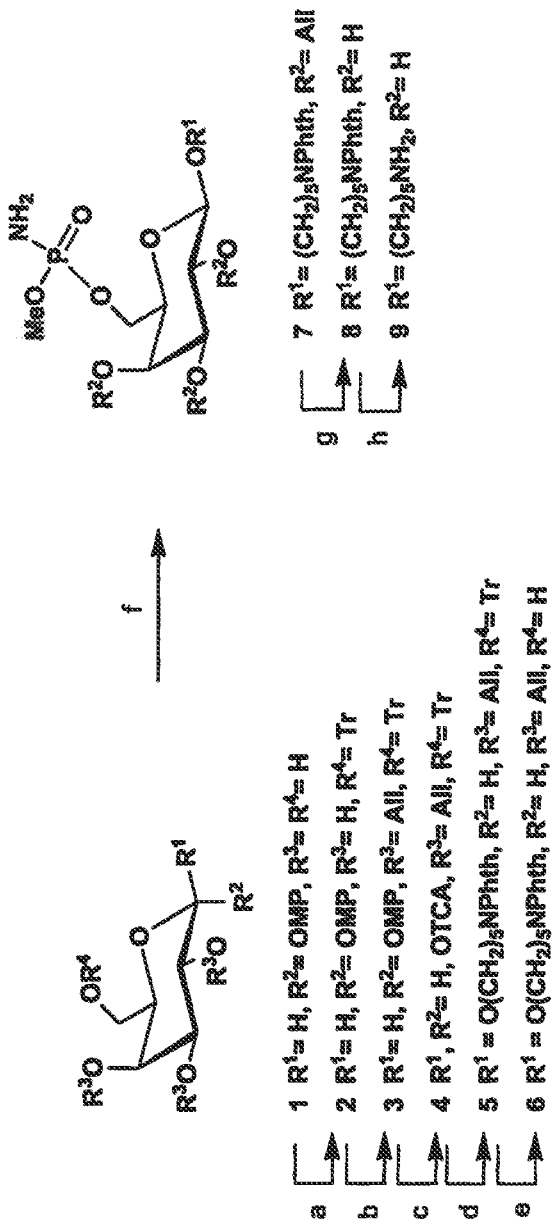
FIG. 4 depicts another scheme for the synthesis of the aminopentyl glycoside of the MeOPN→6-Gal construct (O-Me-phosphoramidate galactoside), MeOPN→6-β-D-Galp-(1→O(CH$_2$)$_5$NH$_2$ ("Scheme 2a".) The reagents and conditions employed in the steps indicated therein are as follows: (a) TrCl, pyridine, 95%; (b) AllBr, NaH, DMF, 0° C., 89%; (c) CAN, $CH_3CN$, $H_2O$, 0° C.; then $CCl_3CN$, $K_2CO_3$, $CH_2Cl_2$, 57% over 2 steps; (d) HO(CH$_2$)$_5$NPhth, TMSOTf, $CH_2Cl_2$, 65%; (e) 80% AcOH, 80° C., 78%; (f) $PCl_2O_2Me_2$, $Et_3N$, $CH_2Cl_2$, then $NH_3(g)$, 27%; (g) $PdCl_2$, MeOH, 75%, (h) $H_2NNH_2$, EtOH, 82%. CAN, cerium ammonium nitrate; TMSOTf, trimethylsilyl trifluoromethanesulfonate; Tr, trityl; All, allyl; OMP, 4-methoxyphenyl group; OTCA, trichloroacetimidate.

The synthesis of the structure MeOPN→6-β-D-Galp-(1→O(CH$_2$)$_5$NH$_2$ can also be depicted as set forth in FIG. 4, Scheme 2a, and is summarized below:

Starting from a previously reported compound (Comfort, et al., Biochem. 46: 3319-3330 (2007)), 4-methoxyphenyl-α-D-galactopyranoside (see Scheme 2a, compound 1), trityl group was selectively introduced to C-6. Originally, benzoylation was performed on compound 2 (Scheme 2a, compound 2), however, extensive migration observed during the introduction of MeOPN lead to the elucidation of a more suitable protecting group. Therefore, allyl groups were selected to protect the C-2, C-3 and C-4 positions which were resistant to migration. Allyl groups were later deprotected with catalytic hydrogenolysis which proved to be compatible with the MeOPN modification.

After allyl groups were installed, an amino-pentanyl linker was introduced to the anomeric position as a site for conjugation. Starting from galactoside (Scheme 2a, compound 3), 4-methoxyphenyl group (OMP) was first removed with cerium ammonium nitrate (CAN.) The corresponding hemiacetal was then converted into trichloroacetimidate donor (see Scheme 2a, compound 4.) 5-Amino-N-phthalimido-pentanyl linker was then introduced with TMSOTf as activator at 0° C. Compound 5 was collected with 65% as the β anomer and 29% as the α anomer. The removal of trityl group gave compound 6 with a free 6-hydroxyl group for modification.

The strategy for the introduction of MeOPN group is similar to a reaction proposed by Mara et al, Bioorg. Med. Chem. Lett. 6180-6183 (2011.) Compound 6 was treated with commercially available methyl dichlorophosphate in the presence of triethyl amine, followed by ammonolysis. Due to the chirality nature of the newly introduced MeOPN (R and S), compound 7 was collected as a mixture of two diastereoisomers. $^1$H NMR was able to confirm that compound 7 was indeed a 1:1 mixture of two diastereoisomers, revealing two sets of signals throughout the spectrum, such can be seen for anomeric and O-Me signals. The reaction yielded a mixture of side products, the most abundant being the O-Me group being replaced by a second NH$_2$, accounting for the poor yield of this reaction.

Allyl and phthalimido protecting groups were removed with palladium (II) chloride and hydrazine respectively, generating compound 8 and compound 9. Similar to compound 7, a mixture of diastereoisomers is apparent in NMR. Although not optically pure, the $^{31}$P NMR result agrees with native MeOPN-containing polysaccharides, having a phosphorous signals around 14 ppm. $^{31}$H-$^{31}$P HMBC NMR experiment was able to confirm that the MeOPN was introduced to the O-6 position, showing correlation signal with O-Me as well as the H-6 signals (data not shown.)

The details of the above synthesis of MeOPN→6-β-D-Galp-(1→O(CH$_2$)$_5$NH$_2$ is provided below and in Scheme 2a:

4-Methoxyphenyl 6-O-trityl-α-D-galactopyranoside (Scheme 2a, Compound 2)

To a solution of compound 1 (2.7 g, 9.3 mmol) dissolved in pyridine (40 mL), trityl chloride (3.1 g, 11 mmol) was added and the reaction mixture was stirred at 60° C. for 3 days. The reaction mixture was then concentrated and purified with flash chromatography (1:1 EtOAc-hexanes) to yield compound 2 (4.7 g, 95%.) $[α]_D^{25}$=+91.2° (c=0.21, CHCl$_3$); $^1$H NMR (400 MHz, CDCl$_3$): δ 7.44-7.20 (m, 15H, Ar—H); 7.11-6.83 (m, 4H, MeOC$_6$H$_4$); 5.51 (d, 1H, J=3.6 Hz, H-1); 4.05-3.93 (m, 4H, H-2, H-3, H-4, H-5) 3.79 (s, 3H, OCH$_3$); 3.54-3.32 (m, 2H, H-6.) $^{13}$C NMR (100 MHz, CDCl$_3$): δ 155.3, 151.2, 150.6, 144.3, 143.8, 143.7, 143.6, 129.1, 128.6, 128.0, 127.9, 127.8, 127.5, 127.3, 127.1, 127.0, 118.5, 117.9, 114.6, 114.5, 114.4 (Ar); 98.4 (C-1); 87.0, 71.2, 70.0, 69.3 (C-2, C-3, C-4, C-5); 63.6 (C-6); 55.6 (CH$_3$.) HRMS (ESI): Calcd. For C$_{32}$H$_{32}$O$_7$ [M+Na]$^+$: 551.2046, found: 551.2021.

4-Methoxyphenyl 2,3,4-tri-O-allyl-6-O-trityl-α-D-galactopyranoside (Scheme 2a, Compound 3)

A solution of compound 2 (4.7 g, 8.8 mmol) dissolved in DMF (60 mL) with allyl bromide (4.6 mL, 53 mmol) was cooled to 0° C. Sodium hydride, 60% dispersion in mineral oil (1.2 g, 29 mmol) was added and the reaction mixture was stirred for 1 h at 0° C. The reaction was then quenched with MeOH (10 mL), poured into ice-cold water (100 mL) and extracted with EtOAc (3×100 mL.) The organic layer was dried over Na$_2$SO$_4$ and concentrated. Purification by flash chromatography eluting with 1:7 EtOAc-hexanes gave compound 3 (see scheme 1, structure 3) (5.1 g, 89%) $^1$H NMR (400 MHz, CDCl$_3$): δ 7.38-7.18 (m, 15H, Ar—H); 7.10-6.75 (m, 4H, MeOC$_6$H$_4$); 6.00-5.53 (m, 3H, CH$_2$—CH=CH$_2$); 5.42 (d, 1H, J=3.2 Hz, H-1); 5.33-4.98 (m, 6H, CH$_2$—CH=CH$_2$); 4.37-3.72 (m, 13H, CH$_2$—CH=CH$_2$, H-2, H-3, H-4, H-5, OCH$_3$); 3.38 (m, 1H, H-6a); 3.01 (m, 1H, H-6b.) $^{13}$C NMR (100 MHz, CDCl$_3$): δ 155.0, 151.0, 143.9 (Ar); 135.2, 135.1, 135.0 (CH$_2$—CH=CH$_2$); 128.6, 127.8, 127.0, 119.0, 117.4, 117.3, 116.4, 114.4 (CH$_2$—CH=CH$_2$, Ar); 97.5 (C-1); 86.8; 78.2 (C-2); 77.4 (C-4); 76.1 (C-5); 73.9, 72.5, 71.9 (CH$_2$—CH=CH$_2$); 70.4 (C-3) 63.3 (C-6); 55.6 (OCH$_3$.) HRMS (ESI): Calcd. For C$_{41}$H$_{44}$O$_7$ [M+Na]$^+$: 671.2985, found: 671.2970.

2,3,4-Tri-O-allyl-6-O-trityl-α,β-D-galactopyranosyl trichloroacetimidate (Scheme 2a, Compound 4)

To a solution of compound 3 (5.0 g, 7.7 mmol) dissolved in CH$_3$CN (480 mL) and H$_2$O (120 mL), cerium ammonium nitrate (12.8 g, 23 mmol) was added and the reaction mixture was stirred for 20 min at 0° C. The mixture was then diluted with brine (200 mL) and extracted with EtOAc (3×300 mL.) The organic layer was washed with saturated aq. Na$_2$CO$_3$ and water, dried over Na$_2$SO$_4$, concentrated and purified with column chromatography (1:6 EtOAc-hexanes.) The resulting hemiacetal (3.3 g, 6.1 mmol) was dissolved in anhydrous CH$_2$Cl$_2$ (120 ml) and CCl$_3$CN (310 μL, 30 mmol) and K$_2$CO$_3$ (420 mg, 30 mmol) were added. The reaction mixture was stirred at room temperature overnight before it was filtered through Celite® and concentrated. Purification with flash chromatography (1:4 EtOAc-hexanes with 1% Et$_3$N by volume) gave compound 4 as an α,β-mixture (3.6 g, 57% over 2 steps.)

5-Amino-N-phthalimido-pentanyl 2,3,4-tri-O-allyl-6-O-trityl-β-D-galactopyranoside (Scheme 2a, Compound 5)

Trichloroacetimidate (compound 4) (1.1 g, 1.6 mmol) and 5-amino-N-phthalimido-pentanol (560 mg, 2.4 mmol) were dissolved in anhydrous $CH_2Cl_2$ (25 mL) and the reaction mixture was cooled to 0° C. TMSOTf (15 μL, 0.080 mmol) was added drop-wise and the reaction mixture was stirred for 15 min at 0° C. The reaction was then neutralized with $Et_3N$ (15 μL) and concentrated. Purification with flash chromatography (1:8 EtOAc-hexanes) gave compound 5 (783 mg, 65%.) $^1H$ NMR (400 MHz, $CDCl_3$): δ 7.80-7.67 (m, 4H, phthalimido protons); 7.41-7.19 (m, 15H, Ar—H); 5.98-5.59 (m, 3H, $CH_2$—CH=$CH_2$); 5.33-4.94 (m, 6H, $CH_2$—CH=$CH_2$); 4.30-3.84 (m, 8H, $CH_2$—CH=$CH_2$, H-1, linker-CHH); 3.77 (d, 1H, J=2.9 Hz, H-5); 3.62 (t, 2H, J=7.3 Hz, linker-$CH_2$); 3.45-3.35 (m, 4H, H-2, H-4, H-6a, linker-CHH); 3.29 (dd, 1H, $J_1$=3.0 Hz, $J_2$=9.8 Hz, H-3); 3.13 (dd, 1H, $J_1$=9.4 Hz, $J_2$=10.1 Hz, H-6b); 1.65 (m, 4H, linker-$CH_2$); 1.40 (m, 2H, linker-$CH_2$.) $^{13}C$ NMR (100 MHz, $CDCl_3$): 168.4, 143.8 (Ar); 135.7, 135.3, 135.2 ($CH_2$—CH=$CH_2$); 133.9, 132.1, 128.7, 127.9, 127.1, 123.2 (Ar); 116.8, 116.5 ($CH_2$—CH=$CH_2$); 103.7 (C-1); 86.8; 81.5 (C-1); 79.2 (C-2); 73.9, 73.6, 73.4, 73.3 (C-5, C-4, $CH_2$—CH=$CH_2$); 71.9, 69.4 (linker); 62.5 (C-6); 37.9, 29.2, 28.4, 23.4 (linker.) HRMS (ESI): Calcd. For $C_{47}H_{51}NO_8$ [M+Na]$^+$: 780.3513, found 780.3489.

5-Amino-N-phthalimido-pentanyl 2,3,4-tri-O-allyl-β-D-galactopyranoside (Scheme 2a, Compound 6)

A solution of compound 5 (493 mg, 0.65 mmol) dissolved in 80% aqueous AcOH (10 mL) was stirred at 80° C. for 1 h. The reaction mixture was concentrated before purification by flash chromatography (1:1 EtOAc-hexanes) giving compound 6 (260 mg, 78%.) $^1H$ NMR (400 MHz, $CDCl_3$): δ 7.81-7.66 (m, 4H, phthalimido protons); 5.92-5.82 (m, 3H, $CH_2$—CH=$CH_2$); 5.30-5.10 (m, 6H, $CH_2$—CH=$CH_2$); 4.37-4.02 (m, 6H, $CH_2$—CH=$CH_2$); 4.22 (d, 1H, J=7.7 Hz, H-1); 3.88 (m, 2H, H-6a, linker-CHH); 3.69-3.60 (m, 4H, H-4, H-6b, linker-$CH_2$); 3.51-3.42 (m, 2H, H-2, linker-CHH); 3.39 (m, 1H, H-5); 3.28 (dd, 1H, $J_1$=3.0 Hz, $J_2$=9.8 Hz, H-3); 2.09 (m, 1H, 6-OH); 1.65 (m, 4H, linker-$CH_2$); 1.40 (m, 2H, linker-$CH_2$.) $^{13}C$ NMR (100 MHz, $CDCl_3$); δ 168.5 (phthalimido C=O); 135.3, 135.0, 133.9 ($CH_2$—CH=$CH_2$); 132.1, 123.2 (phthalimido); 117.8, 116.7, 116.6 ($CH_2$—CH=$CH_2$); 103.9 (C-1); 81.6 (C-3); 79.1 (C-2); 74.6 (C-5) 74.0 (C-4); 73.7, 73.6 ($CH_2$—CH=$CH_2$); 72.1, 69.6 (linker); 62.5 (C-6); 37.8, 29.2, 28.3, 23.3 (linker.) HRMS (ESI): Calcd. For $C_{28}H_{37}NO_8$ [M+Na]$^+$: 538.2417, found 538.2403.

5-Amino-N-phthalimido-pentanyl 2,3,4-tri-O-allyl-6-O-methylphosphoramidate-β-D-galactopyranoside (Scheme 2a, Compound 7)

To a solution of compound 6 (400 mg, 0.78 mmol) and methyl dichlorophosphate (0.70 mL, 6.0 mmol) dissolved in $CH_2Cl_2$ (15 mL) with molecular sieves, $Et_3N$ (0.70 mL, 5.0 mmol) was added drop-wise. The reaction mixture was stirred at room temperature for 12 hours. Upon completion of the reaction as judged by TLC, ammonia gas was injected into the reaction mixture through a needle. After 10 min, the reaction mixture was filtered and concentrated. Purification with column chromatography (9:1 EtOAc-MeOH) yielded product 7 (129 mg, 27%.) $^1H$ NMR (400 MHz, $CDCl_3$): 7.80-7.68 (phthalimido protons); 5.88 (m, 3H, $CH_2$—CH=$CH_2$); 5.30-5.10 (m, 6H, $CH_2$—CH=$CH_2$); 4.23-4.10 (m, 9H, $CH_2$—CH=$CH_2$, H-1, linker-$CH_2$); 3.82 (m, 1H, H-5); 3.71-3.39 (m, 9H, $OCH_3$, H-4, H-6a, H-6b, linker-$CH_2$); 3.28 (m, 1H, H-3); 2.87 (dd, 2H, $J_1$=5.3 Hz $J_2$=13.0 Hz, $NH_2$); 1.66 (m, 4H, linker-$CH_2$); 1.38 (m, 2H, linker-$CH_2$.) $^{13}C$ NMR (100 MHz, $CDCl_3$): δ 168.5 (Ar); 135.4, 135.2, 134.9 ($CH_2$—CH=$CH_2$); 133.9, 132.1, 123.2 (Ar); 117.5, 117.2, 116.8, 116.7, 116.6 ($CH_2$—CH=$CH_2$); 103.8 (C-1); 81.4 (C-3); 78.9 (C-2); 74.0, 73.8, 73.3, 73.2, 73.0, 72.9, 72.1 ($CH_2$—CH=$CH_2$, C-5, C-4); 69.8, 69.7 (C-6) 65.3; 65.0, 64.9 (linker) 53.4, 53.3 ($OCH_3$); 37.9, 29.7, 29.2, 28.3 (linker.) HRMS (ESI): Calcd. For $C_{29}H_{41}N_2O_{10}P$ [M+H]$^+$: 609.2578, found 609.2585.

5-Amino-N-phthalimido-pentanyl 6-O-methylphosphoramidate-β-D-galactopyranoside (Scheme 2a, Compound 8)

To a solution of compound 7 (95 mg, 0.16 μmol) dissolved in MeOH (4 mL), $PdCl_2$ (20 mg) was added and the reaction mixture was stirred at room temperature for 4 h. The reaction mixture was then filtered and concentrated. Purification with column chromatography (9:1 EtOAc-MeOH) gave compound 8 (57 mg, 75%.) $^1H$ NMR (400 MHz, $D_2O$): δ 7.64 (m, 4H, phthalimido protons); 4.23 (d, 1H, J=8.0 Hz, H-1); 4.01 (m, 2H, H-6); 3.78-3.70 (m, 3H, H-4. H-5, linker-CHH)); 3.59-3.45 (m, 7H, $OCH_3$, linker-$CH_2$ linker-CHH, H-3); 3.33 (dd, 1H, $J_1$=8.0 Hz, $J_2$=9.8 Hz, H-2); 1.51 (m, 4H, linker-$CH_2$); 1.22 (m, 2H, linker-$CH_2$.) $^{13}C$ NMR (100 MHz, $D_2O$): 170.9, 134.5, 133.9, 131.3, 126.0, 123.1 (Ar); 102.6 (C-1); 73.2 (C-5); 72.5 (C-3); 71.9 (C-2); 70.3, 70.2 (linker); 68.1 (C-4); 65.4 (C-6); 53.6 ($OCH_3$); 48.7; 37.6 (linker); 28.2; 27.2, 22.3 (linker.) HRMS (ESI): Calcd. For $C_{20}H_{29}N_2O_{10}P$ [M+H]$^+$: 489.1639, found 489.1624.

5-Amino-pentanyl 6-O-methylphosphoramidate-β-D-galactopyranoside (Scheme 2a, Compound 9)

To a solution of compound 8 (23 mg, 0.047 μmol) dissolved in 95% EtOH (1 mL), hydrazine monohydrate (16 μL, 0.33 μmol) was added and the reaction mixture was stirred at room temperature overnight. The reaction mixture was then concentrated and purification with column chromatography (3:1 EtOAc-MeOH) gave compound 9 (14 mg, 82%.) $^1H$ NMR (400 MHz, $D_2O$): δ 4.27 (d, 1H, J=7.1 Hz, H-1); 4.03 (m, 2H, linker-$CH_2$); 3.81-3.75 (m, 3H, H-4, H-5, H-6a); 3.61-3.48 (m, 5H, $OCH_3$, H-3, H-6b); 3.36 (dd, 1H, $J_1$=7.9, $J_2$=9.9 Hz, H-2); 2.82 (t, 2H, J=7.5 Hz, linker-$CH_2$); 1.52 (m, 4H, linker-$CH_2$); 1.30 (m, 2H, linker-$CH_2$.)$^{13}C$ NMR (100 MHz, $D_2O$): δ 102.6 (C-1); 73.2 (C-5); 72.5 (C-3); 70.5 (C-2); 70.1 (C-6); 68.1 (C-4); 60.0 (linker); 48.7 ($OCH_3$); 39.2, 28.0, 26.3, 22.0, 21.9 (linker.) HRMS (ESI): Calcd. For $C_{12}H_{27}N_2O_8P$ [M+H]$^+$: 359.1584, found 359.1587.

Example 2

Synthesis of MeOPN→2-β-D-Galp-(1→OMP

Figure 5:
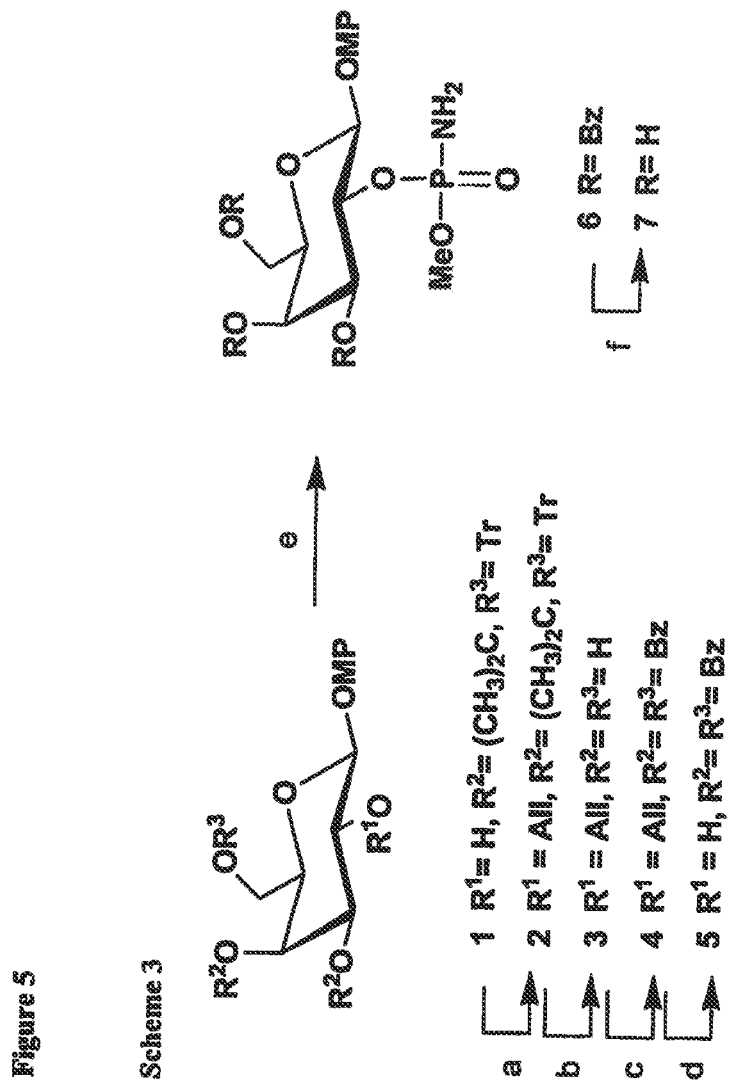
FIG. 5 depicts the synthesis of MeOPN→2-β-D-Galp-(1→OMP ("Scheme 3".) The reagents and conditions employed in the steps indicated therein are as follows: (a) AllBr, NaH, DMF, 0° C., 95%; (b) 80% AcOH, 80° C., 94%; (c) BzCl, pyridine, 97%; (d) $PdCl_2$, MeOH, 92%; (e) $PCl_2(O)OMe$, $Et_3N$, $CH_2Cl_2$, then $NH_{3(g)}$, 26%; (f) NaOMe, MeOH, 73%. All, allyl; Bz, Benzoyl.

Summary Synthesis of MeOPN→2-β-D-Galp-(1→OMP (FIG. 5, Scheme 3)

Figure 14A:
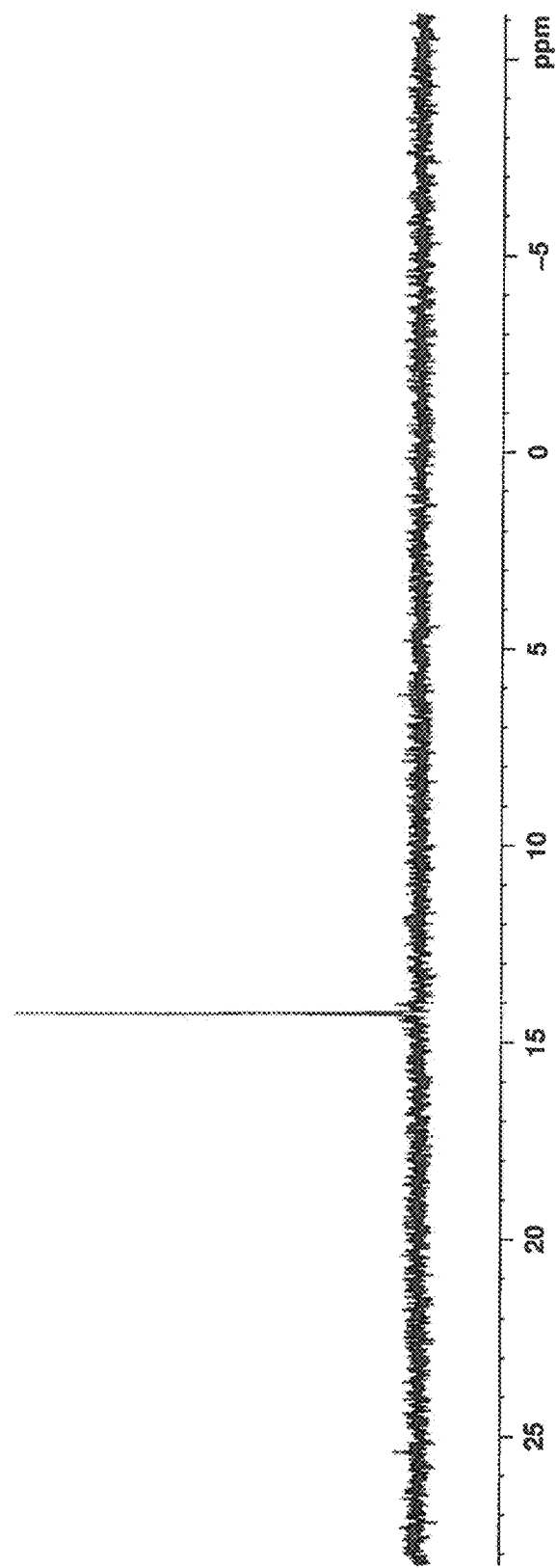
FIG. 14A depicts $^{31}$P NMR data and FIG. 14B depicts $^1$H NMR data of 4-Methoxyphenyl 2-O-methyl-phosphoramidyl-β-D-galactopyranoside performed using conventional methods.
Figure 14B:
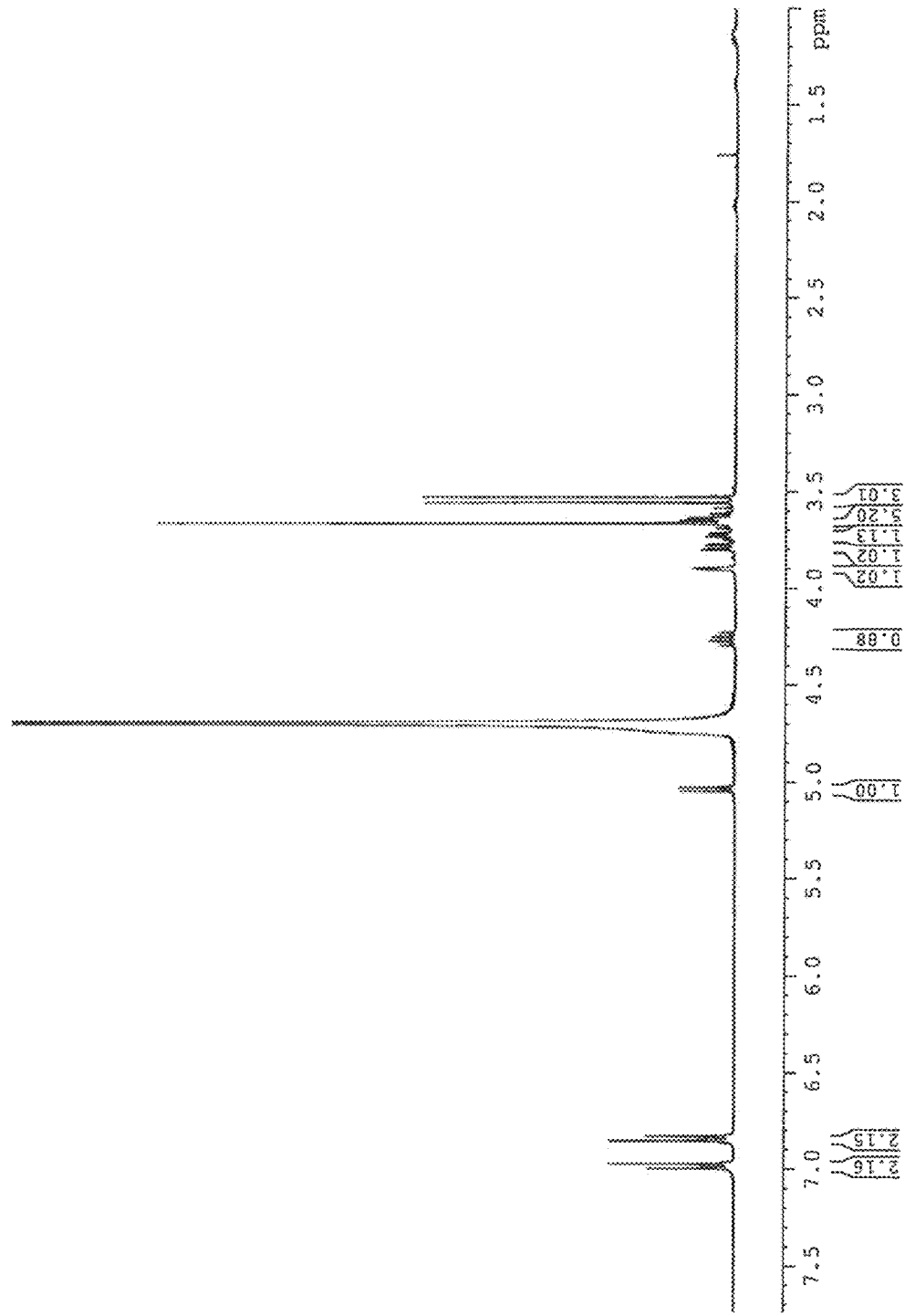

The synthesis of MeOPN→2-β-D-Galp-(1→OMP is depicted in FIG. 5, scheme 3. The synthesis of galactoside (product 7) began with a known compound, 4-methoxyphenyl 3,4-O-isopropylidene-6-O-trityl-β-D-galactopyranoside (product 1), which was prepared from D-galactose following published procedures (Scheme 1.) (Comfort D A, et al., *Biochem* 2007; 46:3319-3330.) To distinguish the C-2 position, O-allylation was performed generating product 2 in excellent yield. Since MeOPN can be removed by acidic media, suitable protecting groups needed to be installed. Thus, O-isopropylidene and O-trityl groups were removed giving product 3, which was then per-benzoylated affording product 4. Next, the allyl group was removed yielding a free 2-OH for modification. The introduction of MeOPN group to product 5 followed a strategy developed in our lab, involving first a phosphorylation with commercially available methyl dichlorophosphate followed by ammonolysis. (Jiao, Y. et al., *Carbohydr. Res.* (2015) doi: 10.1016/j.carres.2015.09.012). The $^{31}$P NMR spectrum of product 5 revealed two phosphorus signals of roughly 1:1 ratio due to the formation of two diastereoisomers. Product 6 was de-benzoylated furnishing O-Me-phosphoramidate galactoside product 7. Interestingly, we were able to purify one of the diastereoisomers using flash chromatography. $^{31}$P NMR spectrum of the diastereoisomer 7* revealed a single signal at 14.27 ppm. See FIG. 14 which depicts $^{31}$P NMR (A) and $^{1}$H NMR (B) of 4-Methoxyphenyl 2-O-methyl-phosphoramidyl-β-D-galactopyranoside performed using conventional methods.

Materials and Methods:

Conventional methods were used to synthesize the compounds, and all chemicals were purchased from commercial suppliers and used as received. Molecular sieves were activated by heating with a heating mantle under reduced pressure. Thin layer chromatography (TLC) was carried out on TLC silica gel $F_{254}$. Sugar compounds were visualized by UV light or by charring with 10% $H_2SO_4$ in ethanol. Flash chromatography was performed with silica gel P60, (43-60 µm, 230-400 mesh.) $^{1}$H NMR and $^{13}$C NMR spectra were recorded with Bruker 400 or 600 MHz spectrometers (Bruker Daltonics Inc, Billerica, Mass.) The proton signal of residual, non-deuterated solvent (δ 7.24 ppm for CHCl$_3$) was used as internal reference for $^{1}$H spectra. For $^{13}$C spectra, the chemical shifts are reported relative to the solvent (δ 77.1 ppm for CDCl$_3$.) Chemical shifts are reported in parts per million (ppm.) Coupling constants are reported in Hertz (Hz.) The following abbreviations are used to indicate the multiplicities: s, singlet; d, doublet; t, triplet; m, multiplet. Optical rotations were measured on a Rudolph Research Autopol III automatic polarimeter (Rudolph Research Analytical, Hackettstown, N.J.) and concentration (c) is expressed in g/100 ml. High-resolution mass spectra for the synthetic compounds were recorded by electron spray ionization mass spectroscopy (time of flight analyzer.)

4-Methoxyphenyl 2-O-allyl-3,4-O-isopropylidene-6-O-trityl-β-D-galactopyranoside (Product 2)

A solution of product 1 (0.68 g, 1.2 mmol) dissolved in DMF (18 mL) with allyl bromide (0.16 mL, 1.8 mmol) was cooled to 0° C. Sodium hydride, 60% dispersion in mineral oil (57 mg, 1.4 mmol) was added and the reaction mixture was stirred for 1 h at 0° C. The reaction was then quenched with MeOH (2 mL), poured into ice-cold water (40 mL) and extracted with $CH_2Cl_2$ (3×50 mL.) The organic layer was dried over $Na_2SO_4$ and concentrated. Purification by flash chromatography eluting with 1:7 EtOAc-hexanes gave 2 (0.69 g, 95%.) $[\alpha]_D^{25}=+40.2°$ (c=0.05, CHCl$_3$); $^{1}$H NMR (400 MHz, CDCl$_3$): δ 7.46-7.19 (m, 15H, Ar); 7.10-6.75 (m, 4H, MeOC$_6$H$_4$); 5.92 (m, 1H, CH$_2$—CH=CH$_2$); 5.34-5.19 (m, 2H, CH$_2$—CH=CH$_2$); 4.67 (d, 1H, J=8.1 Hz, H-1); 4.36 (m, 2H, CH$_2$—CH=CH$_2$); 4.08 (m, 2H, H-3, H-4); 3.73 (s, 3H, OCH$_3$); 3.61-3.53 (m, 3H, H-2, H-5, H-6a); 3.34 (m, 1H, H-6b); 1.47 (s, 3H, CH$_3$); 1.29 (s, 3H, CH$_3$.) $^{13}$C NMR (100 MHz, CDCl$_3$): δ 155.2, 151.5, 144.0, 143.9 (Ar); 134.9 (CH$_2$—CH=CH$_2$); 128.8, 127.9, 127.8, 127.0, 126.9, 118.6, 118.3, 117.7, 117.4, 114.5, 114.4, 110.2, 109.3 (CH$_2$—CH=CH$_2$, Ar); 102.2 (C-1); 86.8 (CMe$_2$) 79.4 (C-2); 79.2; (C-3); 73.8 (C-4); 72.9 (CH$_2$—CH=CH$_2$); 72.6 (C-5); 63.0 (C-6); 55.6 (OCH$_3$); 27.9, 26.3 (CH$_3$.) HRMS (ESI): Calcd. For C$_{38}$H$_{40}$NaO$_7$ [M+Na]$^+$: 631.2672, found: 631.2670.

4-Methoxyphenyl 2-O-allyl-β-D-galactopyranoside (Product 3)

A solution of product 2 (0.69 g, 1.1 mmol) in 80% aqueous AcOH (10 mL) was stirred at 80° C.; for 1 h. The reaction mixture was concentrated under reduced pressure. Purification by flash chromatography (1:1 EtOAc-hexanes) gave 3 (0.35 g, 94%.) $[\alpha]_D^{25}=+90.2°$ (c=0.2, CHCl$_3$); $^{1}$H NMR (400 MHz, CDCl$_3$): δ 7.01-7.78 (m, 4H, MeOC$_6$H$_4$); 5.91 (m, 1H, CH$_2$—CH=CH$_2$); 5.19 (m, 2H, CH$_2$—CH=CH$_2$); 4.83 (d, 1H, J=7.5 Hz, H-1); 4.53-4.25 (m, 2H, CH$_2$—CH=CH$_2$); 4.14 (m, 1H, H-5); 3.96 (m, 1H, H-6a); 3.85 (m, 1H, H-6b); 3.76 (s, 3H, OCH$_3$); 3.62 (m, 3H, H-2, H-3, H-4). $^{13}$C NMR (100 MHz, CDCl$_3$): δ 155.4, 151.1 (Ar); 134.5 (CH$_2$—CH=CH$_2$); 118.5, 118.2, 118.0, 114.6, 114.6 (CH$_2$—CH=CH$_2$, Ar); 102.6 (C-1); 78.4 (C-3); 75.9 (C-4); 73.7 (CH$_2$—CH=CH$_2$); 73.0 (C-2); 68.9 (C-5); 62.8 (C-6); 55.7 (OCH$_3$.) HRMS (ESI): Calcd. For C$_{16}$H$_{23}$O$_7$ [M+H]$^+$: 327.1445, found: 327.1422.

4-Methoxyphenyl 2-O-allyl-3,4,6-tri-O-benzoyl-β-D-galactopyranoside (Product 4)

To a solution of 3 (27 mg, 0.83 mmol) in CH$_2$Cl$_2$ (1 mL) and pyridine (65 µL, 8.3 mmol), BzCl (100 µL, 8.3 mmol) was added and the reaction mixture was stirred at room temperature for 18 hours. MeOH (1 mL) was added and the reaction mixture was concentrated under reduced pressure. Purification with flash chromatography (1:3 EtOAc-hexanes) gave product 4 (51 mg, 97%.) $[\alpha]_D^{25}=+48.6°$ (c=0.1, CHCl$_3$); $^{1}$H NMR (400 MHz, D$_2$O): δ 8.07-7.29 (m, 15H, Ar); 7.06-6.71 (m, 4H, MeOC$_6$H$_4$); 5.89 (d, 1H, J=2.7 Hz. H-4); 5.74 (m, 1H, CH$_2$—CH=CH$_2$); 5.42 (dd, 1H, J$_1$=3.5, J$_2$=10.0 Hz, H-3); 5.21-5.01 (m, 3H, CH$_2$—CH=CH$_2$, H-1); 4.57 (m, 1H, H-6a); 4.39-4.06 (m, 5H, CH$_2$—CH=CH$_2$, H-6b, H-5, H-2); 3.73 (s, 3H, OCH$_3$.) $^{13}$C NMR (100 MHz, CDCl$_3$): δ 171.2, 166.0, 165.7, 155.6, 151.2, 134.3, 133.8, 133.5, 133.2, 133.1, 132.9, 130.6, 130.2, 129.8, 129.7, 129.6, 129.4, 128.8, 128.5, 128.4, 118.8, 114.6 (Ar); 117.7 (CH$_2$—CH=CH$_2$); 102.8 (C-1); 78.7 (C-2); 74.0 (C-3); 73.6 (CH$_2$—CH=CH$_2$); 72.2 (C-5); 69.9 (C4); 63.5 (C-6); 55.6 (CH$_3$.) HRMS (ESI): Calcd. For C$_{37}$H$_{34}$NaO$_{10}$ [M+Na]$^+$: 661.2050, found; 661.2041.

4-Methoxyphenyl 3,4,6-tri-O-benzoyl-β-D-galactopyranoside (Product 5)

To a solution of product 4 (45 mg, 70 µmol) dissolved in MeOH (1 mL), PdCl$_2$ (2 mg) was added and the reaction mixture was stirred at room temperature for 2 h. The reaction mixture was then filtered and concentrated. Purification with column chromatography (1:3 EtOAc-hexanes) gave product 5 (39 mg, 92%.) $[\alpha]_D^{25}=+78.2°$ (c=0.1, CHCl$_3$); $^{1}$H NMR (400 MHz, D$_2$O): δ 8.08-7.28 (m, 15H, Ar); 7.07-6.72 (m, 4H, MeOC$_6$H$_4$); 5.91 (d, 1H, J=3.5 Hz, H-4); 5.45 (dd, 1H, J$_1$=3.5, J$_2$=10.1 Hz, H-3); 5.00 (d, 1H, J=7.8 Hz, H-1); 4.60 (m, 1H, H-6a); 4.44 (m, 1H, H-6b); 4.34 (m, 2H, H-5, H-2); 3.73 (s, 3H, OCH$_3$); $^{13}$C NMR (100 MHz, CDCl$_3$): δ 166.0, 165.5, 155.7, 150.9, 133.7, 133.4, 130.0, 129.9, 129.8, 129.4, 129.2, 129.1, 128.5, 128.4, 118.6, 114.5 (Ar); 102.6 (C-1); 73.2 (C-3); 71.6 (C-5); 69.7 (C-2); 68.1 (C-4); 62.3 (C-6); 55.6 (OCH$_3$.) HRMS (ESI): Calcd. For C$_{34}$H$_{30}$NaO$_{10}$ [M+Na]$^+$: 621.1737, found: 621.1723.

4-Methoxyphenyl 3,4,6-tri-O-benzoyl-2-O-methyl-phosphoramidyl-β-D-galactopyranoside (Product 6)

To a solution of product 5 (18 mg, 0.030 mmol) and methyl dichlorophosphate (70 μL, 0.30 mmol) dissolved in CH$_2$Cl$_2$ (1 mL) with molecular sieves 4 Å, Et$_3$N (85 μL, 0.30 mmol) was added drop-wise. The reaction mixture was stirred at 40° C. for 12 hours. Upon completion of the reaction as judged by TLC, ammonia gas was injected into the reaction mixture through a needle. After 5 min, the reaction mixture was filtered and concentrated. Purification with column chromatography (EtOAc) yielded product 6 (5.4 mg, 26%.) [α]$_D^{25}$=+68.5° (c=0.05, CHCl$_3$); $^1$H NMR (400 MHz, CHCl$_3$): δ 8.06-7.31 (m, 30H, Ar); 7.07-6.72 (m, 8H, MeOC$_6$H$_4$); 5.94 (m, 2H, H-4, H-4*); 5.54 (m, 2H, H-3, H-3*); 5.10 (m, 4H, H-1, H-1*, H-2, H-2*); 4.58 (m, 2H, H-6a, H-6a*); 4.45 (m, 2H, H-6b, H-6b*); 4.35 (m, 2H, H-5, H-5*); 3.73 (s, 3H, OCH$_3$); 3.67 (d, 3H, $^3J_{PH}$=11.6, POCH$_3$); 3.41 (d, 3H, $^3J_{PH}$=11.5, POCH$_3$*); 2.92 (d, 2H, NH$_2$); 2.51 (d, 2H, NH$_2$*.) $^{13}$C NMR (100 MHz, CDCl$_3$): δ 166.0, 165.7, 165.6, 165.5, 155.8, 155.7, 150.8, 150.6, 133.8, 133.6, 133.5, 133.4, 130.1, 130.0, 129.9, 129.8, 129.4, 128.9, 128.8, 128.7, 128.6, 128.5, 128.4, 118.6, 114.7, 114.6 (Ar); 101.2, 101.1 (C-1); 73.9, 73.6 (C-2); 72.5, 72.4 (C-3); 71.7 71.5 (C-5); 68.0 (C-4); 62.1 (C-6); 55.6 (OCH$_3$); 53.6, 53.3 (POCH$_3$.) HRMS (ESI): Calcd. For C$_{35}$H$_{35}$NO$_{12}$P [M+H]$^+$: 692.1898, found: 692.1815.

4-Methoxyphenyl 2-O-methyl-phosphoramidyl-β-D-galactopyranoside (Product 7)

Product 7 (2.5 mg, mmol) was dissolved in 0.25 M methanolic MeONa (1 mL) and the mixture was stirred for 1 h at room temperature before it was neutralized with acetic acid and concentrated. Purification by flash chromatography eluting with 1:1 EtOAe-MeOH gave product 7 (1.0 mg, 73%.)

7: δ $^1$H NMR (400 MHz, D$_2$O): δ 6.97-6.83 (m, 8H, MeOC$_6$H$_4$); 5.05 (2d, 2H, H-1, H-1*); 4.28 (m, 2H, H-2, H-2); 3.91 (m, 2H, H-4, H-4*); 3.77-3.72 (m, 4H, H-3, H-3*, H-5, H-5*); 3.67-3.60 (m, 10H, H-6, H-6*, OCH$_3$); 3.59 (d, 3H, $^3J_{PH}$=11.5 Hz, POCH$_3$.) 3.56 (d, 3H, $^3J_{PH}$=11.5 Hz, POCH$_3$*.) $^{13}$C NMR (100 MHz, CDCl$_3$): δ 154.5, 150.7, 117.7, 114.9 (Ar); 99.7 (C-1); 77.0 (C-2); 75.3 (C-5); 71.6 (C-3); 68.6 (C-4); 60.5 (C-6); 55.6 (OCH$_3$); 53.9 (POCH$_3$.)

7*: [α]$_D^{25}$=−11.0° (c=0.01, H$_2$O); $^1$H NMR (400 MHz, D$_2$O): δ 6.97-6.83 (m, 4H, MeOC$_6$H$_4$); 5.05 (d, 1H, J=7.8 Hz, H-1); 4.28 (m, 1H, H-2); 3.91 (d, 1H, J=3.5 Hz, H-4); 3.77 (dd, 1H, J$_1$=3.5 Hz, J$_2$=9.8 Hz, H-3); 3.72 (m, 1H, H-5); 3.67-3.60 (m, 5H, H-6, H-6', OCH$_3$); 3.56 (d, 3H, $^3J_{PH}$=11.5 Hz, POCH$_3$.) $^{13}$C NMR (100 MHz, CDCl$_3$): δ 154.5, 150.7, 117.7, 114.9 (Ar); 99.7 (C-1); 77.0 (C-2); 75.3 (C-5); 71.6 (C-3); 68.6 (C-4); 60.5 (C-6); 55.6 (OCH$_3$); 53.9 (POCH$_3$.) HRMS (ESI): Calcd. For C$_{14}$H$_{23}$NO$_9$P [M+H]$^+$: 380.1111, found: 380.1085.

Example 3

Immunodetection of MeOPN→6-α-D-Galp-(1→OMP and MeOPN→6-β-D-Galp-(1→O(CH$_2$)$_5$NH$_2$ by C. jejuni CPS Conjugate Antisera The synthetic p-methoxyphenyl and aminopentyl glycosides of the MeOPN→6-Gal construct, compounds MeOPN→6-α-D-Gal-(1→OMP and MeOPN→6-β-D-Galp-(1→O(CH$_2$)$_5$NH$_2$, synthesized as described in the above examples, were tested per reactivity with antisera previously raised against C. jejuni CPS conjugates of serotypes HS1, HS3, HS4 and HS23/36. Notably, of the listed serotypes, only HS23/36 expresses MeOPN-6-Gal.

Materials and Methods

The synthetic construct MeOPN-6-Gal was adjusted to 1 mg/ml and 2 μl was spotted onto nitrocellulose membranes and allowed to dry. The individual spots were immunodetected with four different polyclonal antisera made against different conventional conjugate vaccines in which different C. jejuni polysaccharide capsules were conjugated to CRM$_{197}$: (1) rabbit serum against an HS23/36 conjugate (final dilution 1:1000 in 20 mM Tris, pH 7.4, 0.425 M NaCl, 0.05% Tween 20 (TBST); Monteiro et al., (2009) Infect. Immun. 77, 1128-1136; U.S. Pat. No. 9,084,809); (2) rabbit serum against an HS4 conjugate (final dilution 1:1000; Monteiro et al., (2009) Infect. Immun. 77, 1128-1136; U.S. Pat. No. 9,084,809); (3) mouse serum against an HS1 conjugate (final dilution 1:500; unpublished data); and (4) mouse serum against an HS3 conjugate (final dilution 1:500; US 2015/0273037.) Secondary antibodies used were either goat anti-rabbit (for HS23/36 and HS4) or goat anti-mouse (HS1 and HS3 (Thermo-Pierce, Rockford, Ill.) Rabbit antibodies were obtained from Harlan Laboratories (Indianapolis, Ind.) and mouse antibodies were generated in house using conventional methods. Immunoblots were developed using a chemiluminescence kit (Pierce Supersignal West Femto Maximun Sensitivity Substrate, Thermo Fischer Scientific, Waltham, Mass.) and imaged on a Bio-Rad gel imager (Bio-Rad Laboratories, Hercules, Calif.) The conjugate with linker was analyzed using similar methods.

Figure 6A:
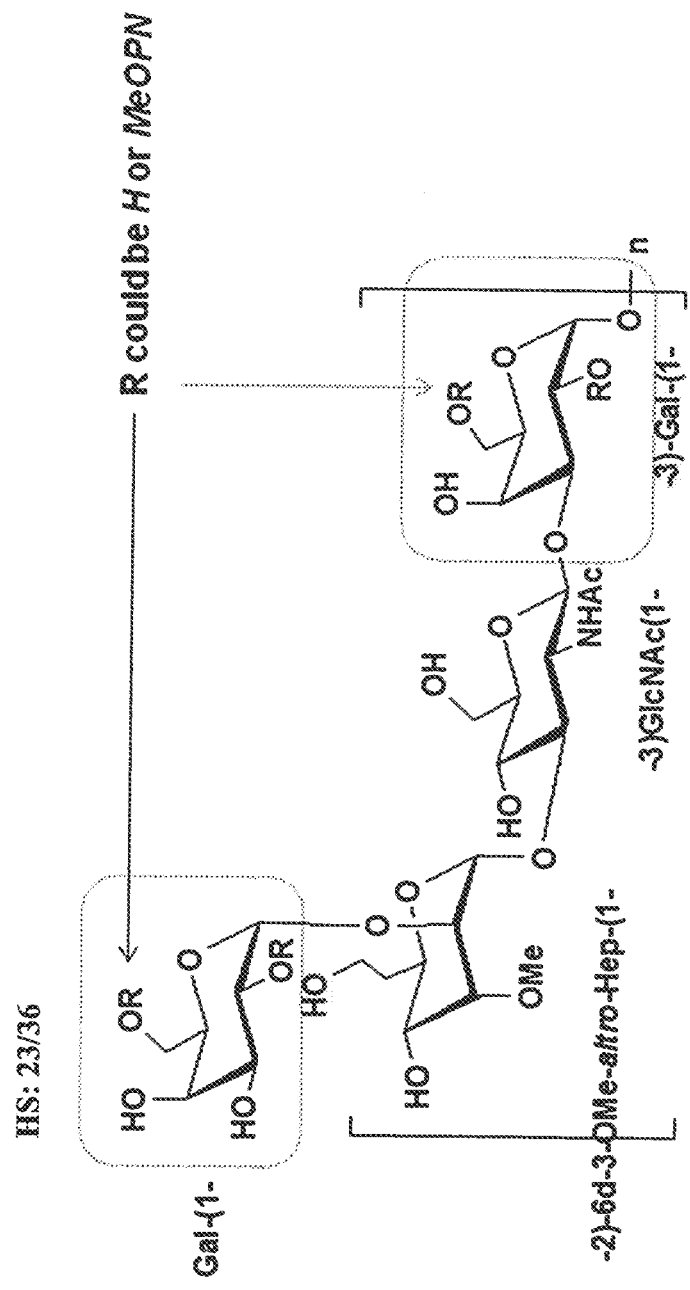

As illustrated in FIG. 6(B), the monosaccharide construct MeOPN-6-Gal was recognized by antibody against capsule polysaccharide isolated from HS23/36 conjugated to CRM$_{197}$ (CPS with a MeOPN at C-6 of Gal.) Unexpectedly, antibody against polysaccharide from HS4 conjugated to CRM$_{197}$ (CPS with MeOPN at C-7 of ido-heptose) also elicited a response equivalent to anti-HS23/36 CRM$_{197}$ conjugate against MeOPN-6-Gal. Also, anti-HS1-CRM$_{197}$ (CPS with low amounts of MeOPN at C-6 Gal) also reacted to MeOPN-6-Gal, although to a somewhat lesser extent. The HS3 CPS conjugate antisera (CPS with MeOPN at C-2 of ido-heptose) did not react with MeOPN-6-Gal. No reaction was observed between α-D-Gal-(1-OMP (devoid of MeOPN) and HS23/36 CPS conjugate antisera (data not shown.) Thus, the data show that antibodies generated against HS23/36, HS4 and HS1 all react with the synthetic MeOPN-6-Gal antigen. In contrast, these antibodies do not react with heterologous capsules. In other words, there is no detectable reactivity of anti-HS23/36 antibodies with purified HS4 or HS1 capsules.

The strong cross-reactivity with MeOPN-6-Gal exhibited against HS23/36 and HS4 antibody may be explained by the fact that MeOPN-6-Gal share epitopic structures with HS23/36 and HS4 capsule polysaccharides. One explanation may be that the MeOPN group in both HS23/36 and HS4 is to a primary hydroxyl. The cross reaction of MeOPN-6-Gal (HS23/36) with HS4, which contains MeOPN-7-6d-β-D-ido-Heptose, was unexpected, but may be due to the linkage of MeOPN to primary hydroxyl positions on both sugars.

Figure 7:
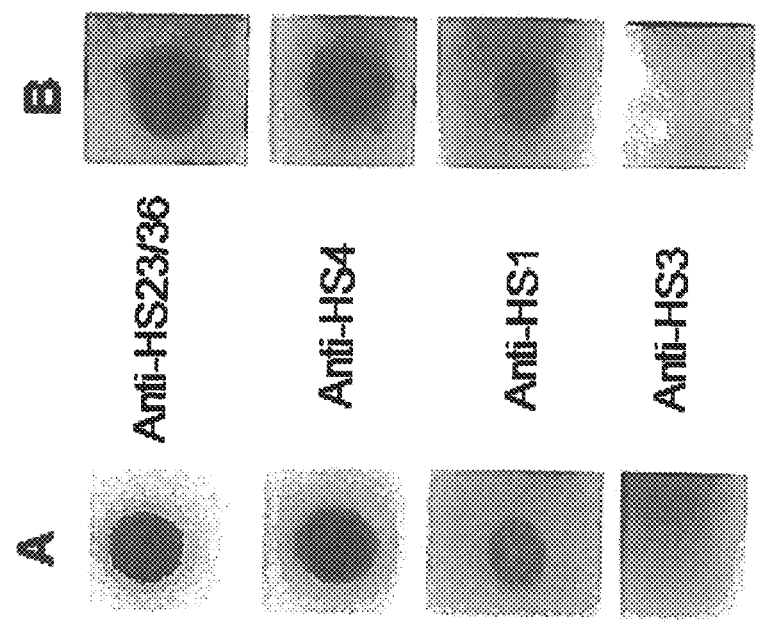
FIG. 7 depicts the immunodetection of MeOPN→6-α-D-Galp-(1→OMP (column A) and MeOPN→6-β-D-Galp-(1→O—(CH$_2$)$_5$NH$_2$ (column B) by *C. jejuni* CPS conjugate antisera of serotypes HS1 (1:500), HS3 (1:500), HS4 (1:2000) and HS23/36 (1:2000) as indicated in the center column. Dilutions were done in TBST (20 mM Tris, pH 7.4, 0.425 N NaCl, 0.05% Tween 20.) Data show that antibodies to HS23/36, HS4 and HS1 serotypes of *C. jejuni* can react with the synthetic MeOPN-6-Gal construct either with or without added linker.

FIG. 7 compares the recognition of constructs MeOPN→6-α-D-Galp-(1→OMP in column A (same data as FIG. 6B) with data in column B using construct MeOPN→6-β-D-Galp-(1→O(CH$_2$)$_5$NH$_2$ using the indicated conjugate antisera. As depicted in FIG. 7, both constructs were strongly recognized by HS23/36 CPS conjugate antisera (whose CPS contains a MeOPN→6-α-D-Gal linkage in non-stoichiometric amounts), by HS4 CPS conjugate antisera (whose CPS has a non stoichiometric MeOPN→7-6d-ido-Hep linkage), and, albeit with weaker intensity, by HS1 CPS conjugate antisera (that contains a very low amount of MeOPN→6-α-D-Gal.) As discussed above, the detection of synthetic MeOPN→6-D-Gal by HS23/36, HS4, and HS1 CPS conjugate antisera points to the fact that these polyclonal preparations contain specific antibodies for MeOPN units at primary positions. The HS3 CPS conjugate antisera (with MeOPN at C-2 of 6d-ido-Hep in CPS) did not react with either synthetic constructs MeOPN→6-α-D-Galp-(1→OMP or MeOPN→6-β-D-Galp-(1→O(CH$_2$)$_5$NH$_2$ (data not shown.) No reaction was observed between the Gal OMP and aminopentyl glycosides (devoid of MeOPN) and HS23/36 CPS conjugate or whole-cell antisera (data not shown.)

As indicated in FIG. 7, within the limits of detection, no difference in antisera reactivity was observed between MeOPN→6-α-D-Galp-(1→OMP and MeOPN→6-β-D-Galp-(1→O(CH$_2$)$_5$NH$_2$, which suggests that the recognition of MeOPN at the exocyclic C-6 position of Gal was not dependent on the anomeric configuration. That MeOPN→6-Gal was accessible in a conjugate format was confirmed by the reaction of HS23/36 whole-cell sera with a MeOPN→6-Gal CRM$_{197}$ conjugate. These data indicate that the synthetic MeOPN→6-Gal entities (regardless of anomeric configuration) not only react with antisera raised by homologous C. jejuni HS23/36 CPS conjugate, but also with those generated by serotypes HS1 and HS4, which also contain a MeOPN at a primary position (see, e.g., FIG. 1.)

Example 4

MeOPN-6-Gal is an Immunodominant Epitope in Synthetic Conjugate Vaccines

Until the discovery of a second MeOPN linkage at Gal-O-6 reported herein, MeOPN had only been reported on the O-2 position of galactose. Kanipes et al., (2006) *J Bacteriol.* 188, 3273-3279. The below experiment utilizing a synthetic CPS conjugate vaccine demonstrates that the MeOPN linkage at Gal-O-6 is immunodominant over MeOPN-2-Gal.

Materials and Methods

Two microliters of a 1 mg/ml solution of synthetic MeOPN-6-Gal (prepared as disclosed above) and two isomers ("A" and "B") of MeOPN-2-Gal (prepared as disclosed herein) were spotted onto a nitrocellulose filters using conventional methods and allowed to dry. The filters were blocked with the blocking agent provided with Supersignal West Femto Maximum Sensitivity Substrate (Thermo Fierce, Rockford, Ill.) Filters were mixed with primary rabbit polyclonal antibodies made against formalin killed whole cells of C. jejuni strain 81-176 (final dilution 1:500 in (20 mM Tris, pH 7.4, 0.425 N NaCl, 0.05% Tween 20) (Bacon et al., (2001) *Mol. Microbiol.* 40, 769-777) or rabbit antibody to an HS23/36 polysaccharide-CRM197 conjugate vaccine (final dilution 1:1000) (Monteiro et al., (2009) *Infect. Immun.* 77, 1128-1136.) Filters were reacted with primary antibody overnight and then washed. Secondary antibody was goat anti-rabbit IgG (final dilution, 1:50,000) (Thermo-Pierce, Rockford, Ill.) After washing the filters were detected with Supersignal West Femto Maximum Sensitivity Luminescence Substrate and images were recorded on a Bio-Rad gel imaging system (Bio-Rad Laboratories, Hercules, Calif.)

Figure 8:
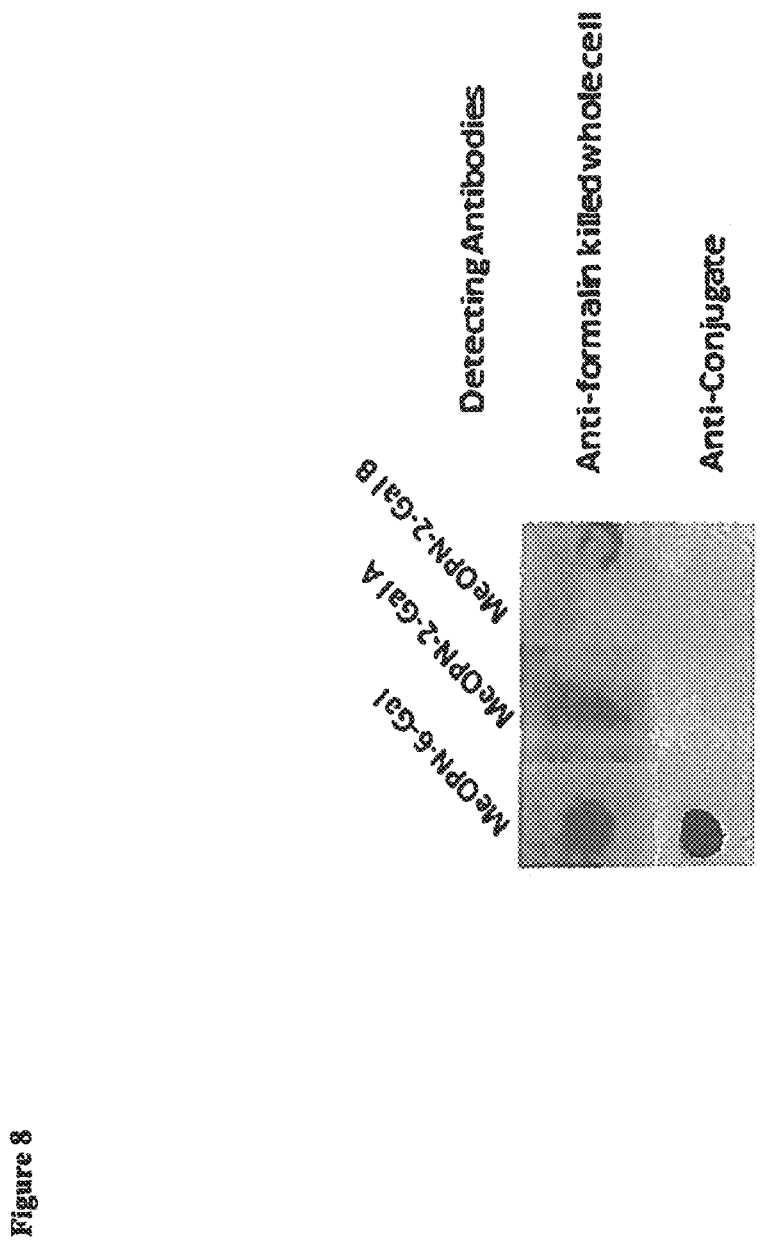
FIG. 8 depicts an immunoblot which demonstrates that rabbit antibodies to an HS23/36 polysaccharide-CRM$_{197}$ conjugate vaccine detected MeOPN-6-Gal, but did not detect isomers of MeOPN-2-Gal. These data clearly indicate the immunogenicity of the MeOPN-6-Gal monosaccharide and the immunodominance of the methyl phosphoramidate at the 6 position of Gal over MeOPN at the 2 position of Gal in synthetic constructs.

As depicted in FIG. 8, results clearly indicate that the rabbit antibody to an HS23/36 polysaccharide-CRM197 conjugate vaccine detected MeOPN-6-Gal, but did not detect either isomer of MeOPN-2-Gal. Similar results were obtained using the rabbit polyclonal antibodies, although some reactivity was detected against MeOPN-2-Gal B isomer. These data clearly indicate the immunogenicity of the MeOPN-6-Gal monosaccharide and the immunodominance of the methyl phosphoramidate at the 6 position of Gal over MeOPN at the 2 position of Gal. In addition to the chemical synthesis of MeOPN-sugar epitopes as contemplated herein, CPS-based vaccines against C. jejuni might be improved by exploiting the immunodominance of MeOPN-modified sugars, e.g., by using strains that overexpress the immunodominant epitopes and/or biologically important epitopes for capsule purification and vaccine production.

Example 5

Conjugation of MeOPN→6-β-D-Galp-(1→O(CH$_2$)$_5$NH$_2$ to Protein CRM$_{197}$

Figure 9:
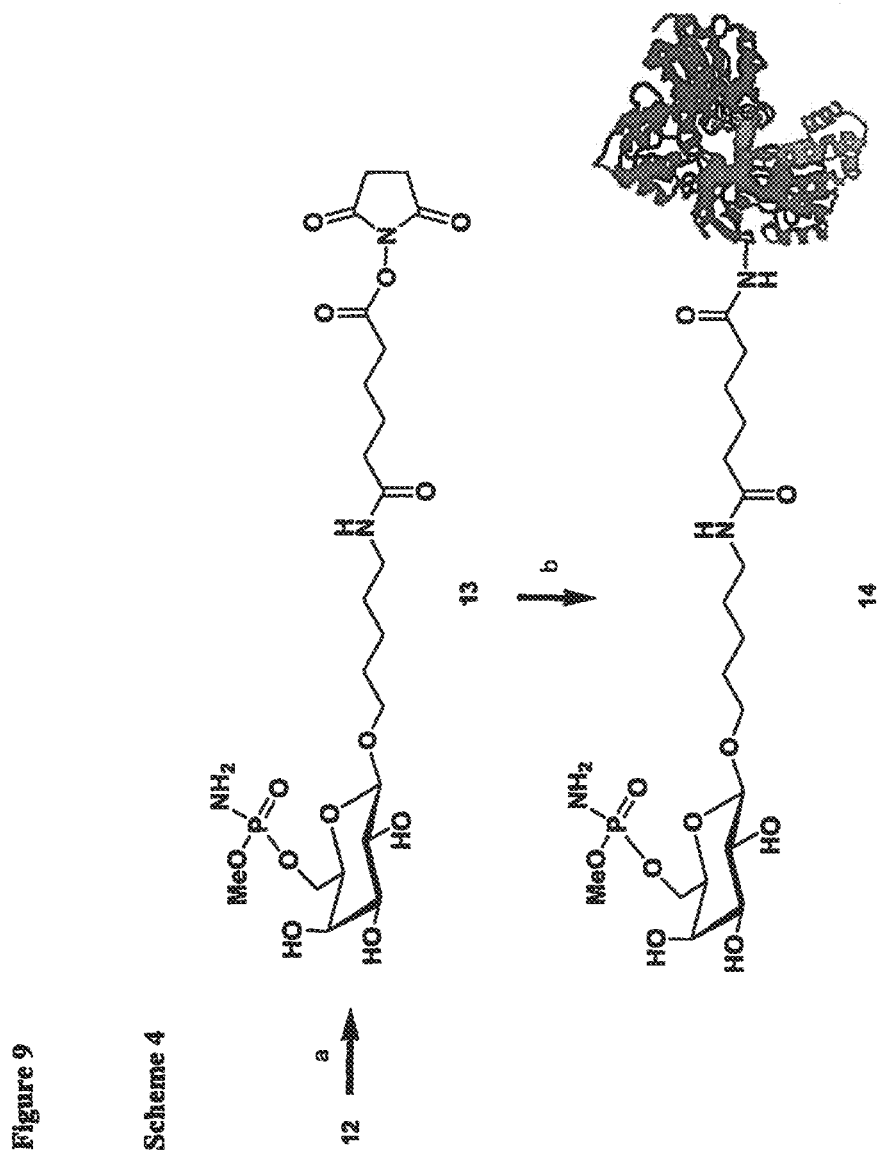
FIG. 9 depicts the conjugation of the linker-equipped galactoside with carrier protein, CRM$_{197}$ (CRM$_{197}$ is depicted as ribbon diagram) ("Scheme 4".) The reagents and conditions employed in the steps indicated therein are as follows: (a) di-N-hydroxy-succinimidyl adipate ester, Et$_3$N DMSO; (h) CRM$_{197}$, 70 mM NaPi, pH 7.0.
Figure 12:
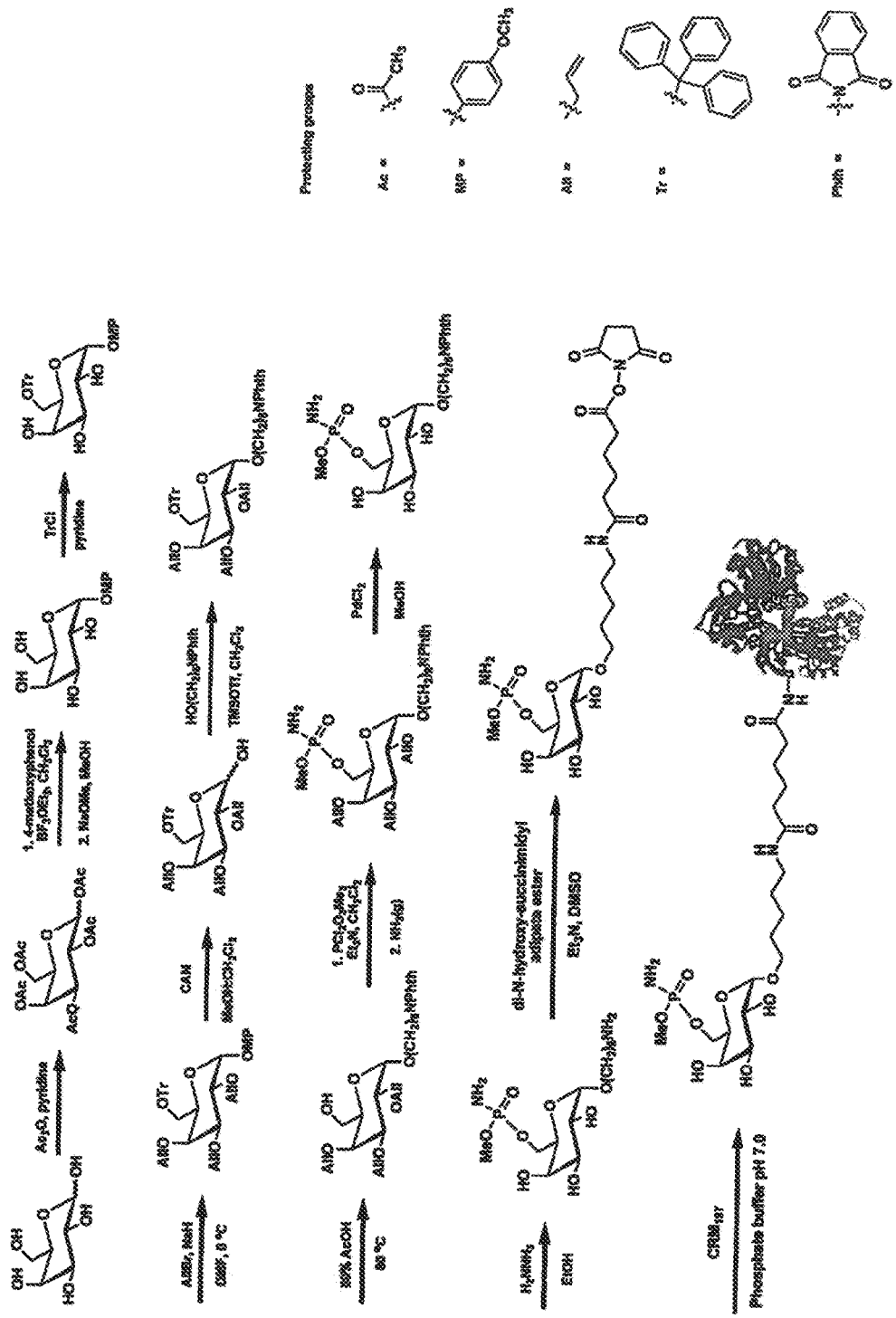
FIG. 12 depicts a summary of the synthesis of the MeOPN-6-Gal monosaccharide construct and conjugation to the carrier protein CRM$_{197}$. Ac, acetyl; MP, Methoxyphenyl; All, allyl; Tr, trityl; Phth, phthalimido.

The linking of a synthetic construct to a protein carrier to form a conjugate is depicted in FIG. 9 (Scheme 4.) The linker equipped galactoside (compound 12 from FIG. 3 or compound 9 from FIG. 4) (4.5 mg) and an excess of adipic acid N-hydroxysuccinimido diester (10 equiv.) was dissolved in DMSO (1 ml.) Triethylamine (60 µl), was added drop-wise and the reaction mixture was stirred at room temperature for 4 h. After concentration under reduced pressure, the residue was extracted with H$_2$O, followed by purification with column chromatography (3:1 EtOAc-Hexane) giving the activated monosaccharide, compound 13. This resulting half ester, (compound 13) was then condensed with the amino groups of the protein CRM$_{197}$ in phosphate buffer (NaPi buffer, pH 7) to yield compound 14. Specifically, conjugation was carried out with the activated monosaccharide with CRM$_{197}$ at a molar ratio of 100:1 (moles of active ester per moles of protein) in 70 mM phosphate buffer pH 7.0. After stirring 3 days at room temperature, the conjugate (compound 14) was dialyzed against running water. A summary of the synthesis of the conjugate and linkage to a protein carrier is also depicted in FIG. 12.

The conjugation was analyzed and confirmed with SDS-PAGE gel and mALDI-TOF. Specifically, the conjugation of MeOPN→6-β-D-Galp-(1→O(CH$_2$)$_5$NH$_2$ to CRM$_{197}$ was analyzed and confirmed by gel electrophoresis (FIG. 10A) Western blot (FIG. 10B) and mass spectrometry (mALDI-TOF) (FIG. 10C) according to conventional methods.

Materials and Methods

Figure 10:
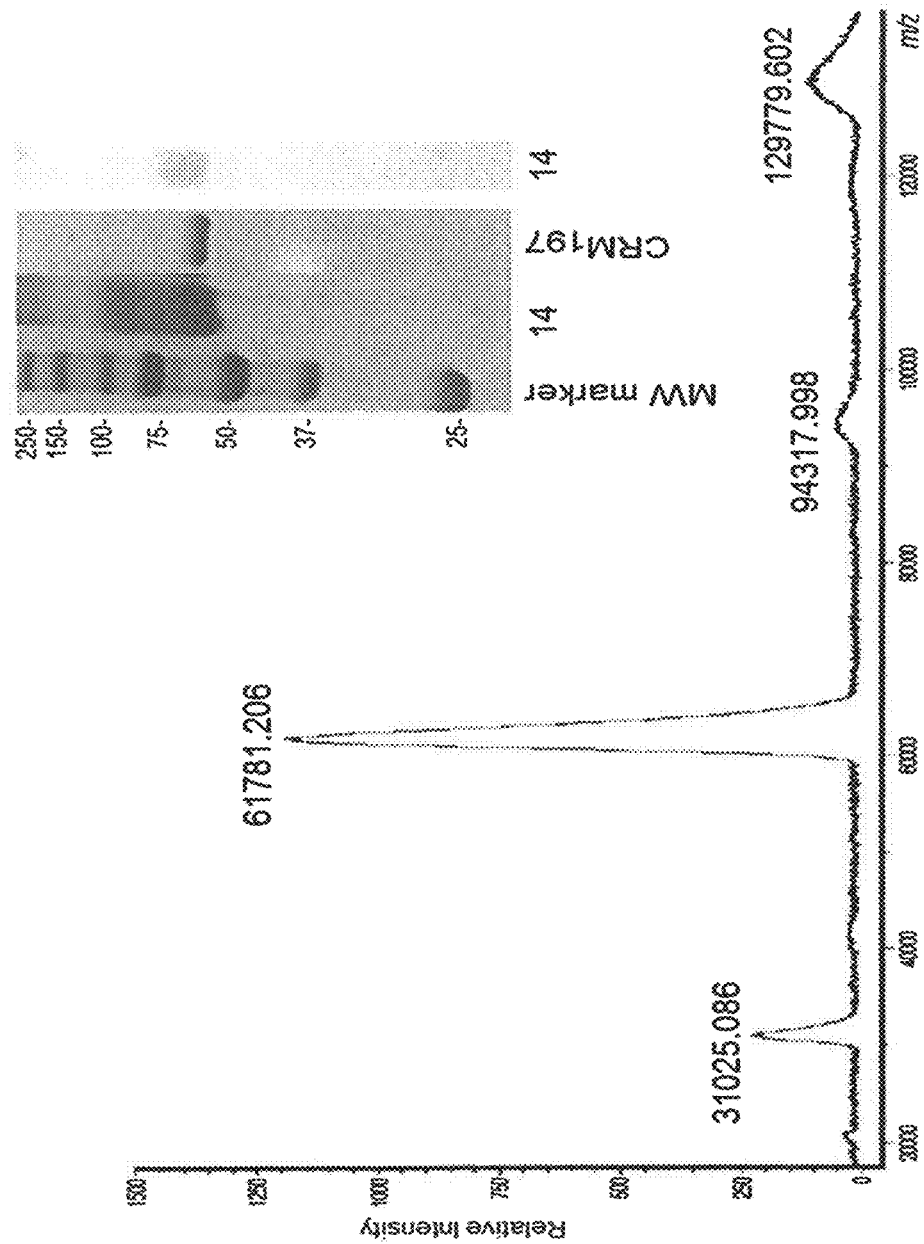
FIG. 10A, FIG. 10B, and FIG. 10C depict the analysis and confirmation of conjugation of linker equipped galactoside with carrier protein. Specifically.

The MeOPN-6-Gal construct linked to CRM$_{197}$ was analyzed and characterized by SDS-PAGE and immunoblotting using conventional methods. Samples of the synthetic MeOPN-6-Gal linked to CRM$_{197}$ (2.5 µg and 5 ug by weight) were analyzed on 12.5% SDS-PAGE gels and either stained with GelCode™ Blue Stain Reagent (ThermoFischer Scientific, Waltham, Mass.) or transferred to nitrocellulose and immunodetected with rabbit poly-clonal antibodies to whole cells of C. jejuni 81-176 (HS23/36) (Bacon et al., (2001) *Mol. Microbiol.* 40, 769-777.) The stained SDS-PAGE gel indicated that the vaccine conjugate was heterogeneous in size, ranging from slightly larger than unconjugated CRM$_{197}$ to >250 Kd. (FIG. 10A.) Results from immunoblotting indicate that the vaccine conjugate reacted with rabbit polyclonal antibodies to whole cells of *C. jejuni* strain 81-176 indicating cross reaction between the capsule and the conjugate (data not shown.) Due to the fact that the final product (the conjugate) contained diastereoisomers of MeOPN, only half of the MeOPN→6-D-Galp epitopes reflected those in the native CPS. Even so, Western blot analysis with HS23/36 whole cell antisera showed that the conjugate exposed MeOPN→6-D-Gal epitopes that mimic MeOPN stereochemistry and linkage on cell-surface (FIG. 10B.)

The conjugate was also analyzed by MALDI-TOF using conventional methods to more accurately determine masses of the conjugate. Briefly, sinapinic acid (Sigma Aldrich, St. Louis, Mo.) was saturated in 30:70 (v/v) acetonitrile (ACN): 0.1% trifluoroacetic acid (TFA) in water as the matrix. The matrix and sample (1 mg/mL) were pre-mixed in equal volumes, and 1 µL was deposited on a ground steel plate by dry droplet method for analysis. Microflex LRT matrix-assisted laser desorption and ionization time-of flight (MALDI-TOF) mass spectrometer (Bruker Daltonics Inc, Billerica, Mass.) was set at linear mode with positive ion detection to obtain the mass spectra. Results indicate that the MeOPN-6-Gal-CRM$_{197}$ conjugate vaccine gave a major peak of mass 61,781. The mass for CRM$_{197}$ in a similar MALDI experiment was 57,967 daltons (not shown.) Thus, the mass difference is 3,814 daltons. Since the mass of MeOPN-6-Gal and the linker is 461 daltons (data not shown), this indicates that approximately 8 MeOPN-6-Gal-linker moieties were added per CRM$_{197}$ molecule. No larger form was detected, however, this may be due to the fact that larger molecules are more difficult to detect using the Bruker Daltonics instrument.

Example 6

MeOPN→6-β-D-Gal CRM$_{197}$ Conjugate Antibodies Recognize *C. jejuni* HS23/36 Cell-Surface and have Bactericidal Activity We have previously demonstrated that immunogenic capsule polysaccharide conjugate vaccines ("conventional" vaccines) against *C. jejuni* elicit serum bactericidal antibodies (SBAs) (data not shown) In other words, the antibodies generated against the conventional polysaccharide vaccine can bind to the bacterium in the presence of complement and induce bacterial lysis. As discussed in the above examples, MeOPN-6-Gal has been synthesized and shown to react with antibodies to conventional CRM$_{197}$ conjugate vaccines based on both HS23/36 and HS4. A vaccine conjugate composed of MeOPN-6-Gal linked to CRM$_{197}$ with approximately 8 MeOPN-6-Gal moieties per protein was synthesized as provided above and tested for immunogenicity in rabbits.

Materials and Methods

A rabbit was immunized with four doses (250 ug each) of MeOPN-6-Gal linked to a synthetic CRM$_{197}$ vaccine conjugate (Envigo, Frederick, Md.) with Freund's adjuvant (BD Difco brand containing 5 mg Mycobacterium butyricum/10 ml administered 1:1 with the antigen (Becton, Dickinson and Co., Franklin Lakes, N.J.)). The final serum was used in an ELISA in which *C. jejuni* 81-176 capsule conjugated to BSA was the detecting antigen. The endpoint titer of the serum was 1:200. The rabbit serum generated against MeOPN-6-Gal was heat-inactivated by heating to 56° C. for 30 minutes to inactivate endogenous complement. As a control, the pre-bleed of the same rabbit (prior to immunization) was also heat inactivated. Sera were serially diluted in a microliter plate, mixed with *C. jejuni* 81-176 and baby rabbit complement. The plate was incubated at 37° C. under microaerobic conditions. Aliquots from each well were plated onto Mueller Hinton agar plates to enumerate the surviving bacterial cells. The results are reported as the fold-increase in killing between the pre-bleed and the final bleed of the immunized rabbit.

Figure 11:
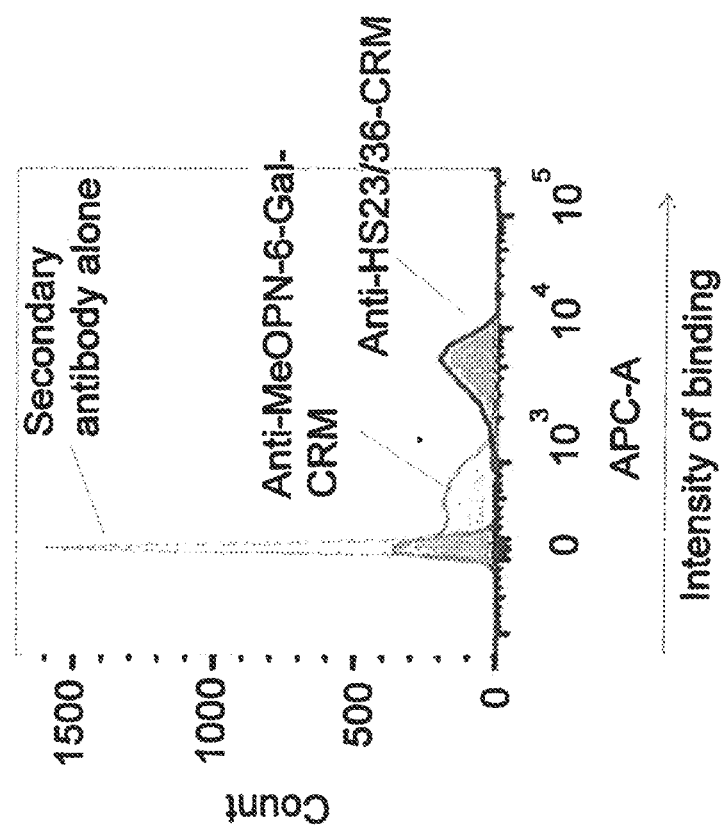
FIG. 11 depicts flow cytometry analysis of *C. jejuni* HS23/36 cells with antisera raised by HS23/36 CPS conjugate (peak between approx. $10^3$-$10^4$) and synthetic MeOPN→6-β-D-Gal CRM$_{197}$ conjugate 14 (peak between approx. 0 and −$10^3$). Peak at 0 represents binding of secondary antibody alone. APC-A, Allophycocyanin. Data demonstrate that a synthetic conjugate vaccine of the invention is capable of conjuring up antibodies in rabbits specific to the CPS MeOPN→6-D-Gal linkage exposed on the cell-surface of *C. jejuni* HS23/36 cells.

The results for the rabbit immunized with the synthetic MeOPN-6-Gal-CRM$_{197}$ conjugate vaccine indicated a 16-fold increase in serum bacteriocidal activity. Results from flow cytometry are depicted in FIG. 11. Data indicate that the conjugate vaccine (e.g., compound 14 in FIG. 9) is capable of inducing antibodies in rabbits specific to the CPS MeOPN→6-D-Gal linkage exposed on the cell-surface of *C. jejuni* HS23/36 cells. The intensity of binding to *C. jejuni* HS23/36 cells was higher using antibodies raised by the native CPS conjugate. Intensity of binding to *C. jejuni* HS23/36 cells was lesser with the antibodies raised to the synthetic vaccine, and a portion of the cells did not react with MeOPN→6-D-Gal antibodies at all. However, binding of these antibodies to the surface of HS23/36 cells is consistent with the observed rise in SBA titer discussed above.

Example 7

Figures 16A, 16B:
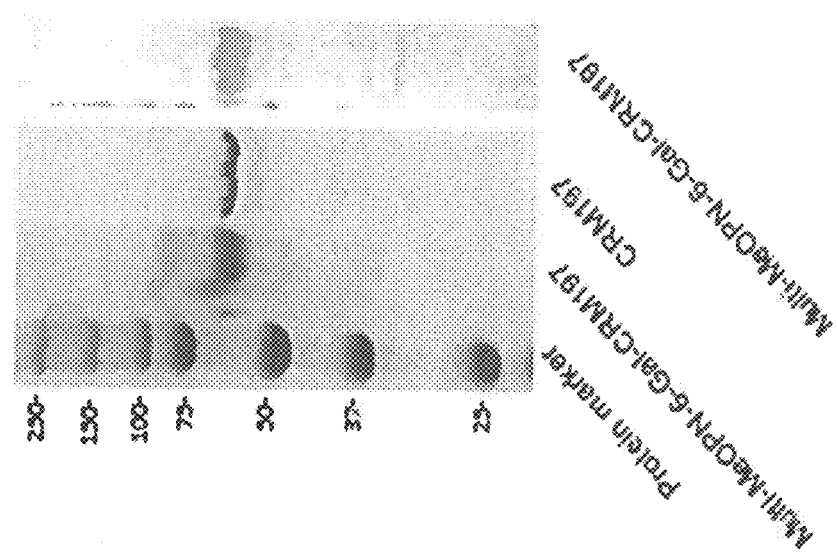
FIG. 16A depicts a 12.5% SDS-PAGE gel (sodium dodecyl sulfate-polyacrylamide gel electrophoresis)
FIG. 16B depicts an immunoblot of the synthetic polymeric construct of FIG. 15 comprising multiple MeOFN-6-Gal monosaccharides. As indicated, FIG. 16A includes lanes for the molecular weight marker, the synthetic construct, and carrier protein alone.

Synthesis of Polymeric Constructs Comprising *Campylobacter jejuni* Synthetic Antigens Immunogenic synthetic constructs comprising one or more synthetic MeOPN-monosaccharides and optionally associated with one or more other saccharides are contemplated herein. Examples of such polymeric constructs which have been synthesized are depicted herein in FIG. 15 and FIG. 16.

Materials and Methods

The multi MeOPN-6-Gal polymeric conjugate of FIG. 15 was synthesized using conventional methods, commercially available reagents, and monosaccharides disclosed herein and in the proceeding examples. Lintner starch (100 mg) was activated with 0.04 M NaIO$_4$ in 0.1 M NaOAc buffer (100 ml) pH 4, at 4° C. for 3 days. After 2 days of dialysis against water, 1000 Da molecular cutoff, the product mixture was centrifuged. The supernatant was lyophilized and further purified on a Bio-Gel® P-2 column (Bio-Rad Laboratories, Hercules, Calif.)

The activated starch (8 mg) was chemically conjugated with MeOPN→6-β-D-Galp-(1→O(CH2)$_5$NH$_2$ (4 mg) in 0.1 M borate buffer (5 ml), pH 9. Sodium cyanoborohydride (40 mg) was added and the reaction mixture was stirred for 1 day at RT and 2 days at 37° C. The conjugate was then dialyzed against running water (1000 Da) for 2 days and then lyophilized.

Figure 17:
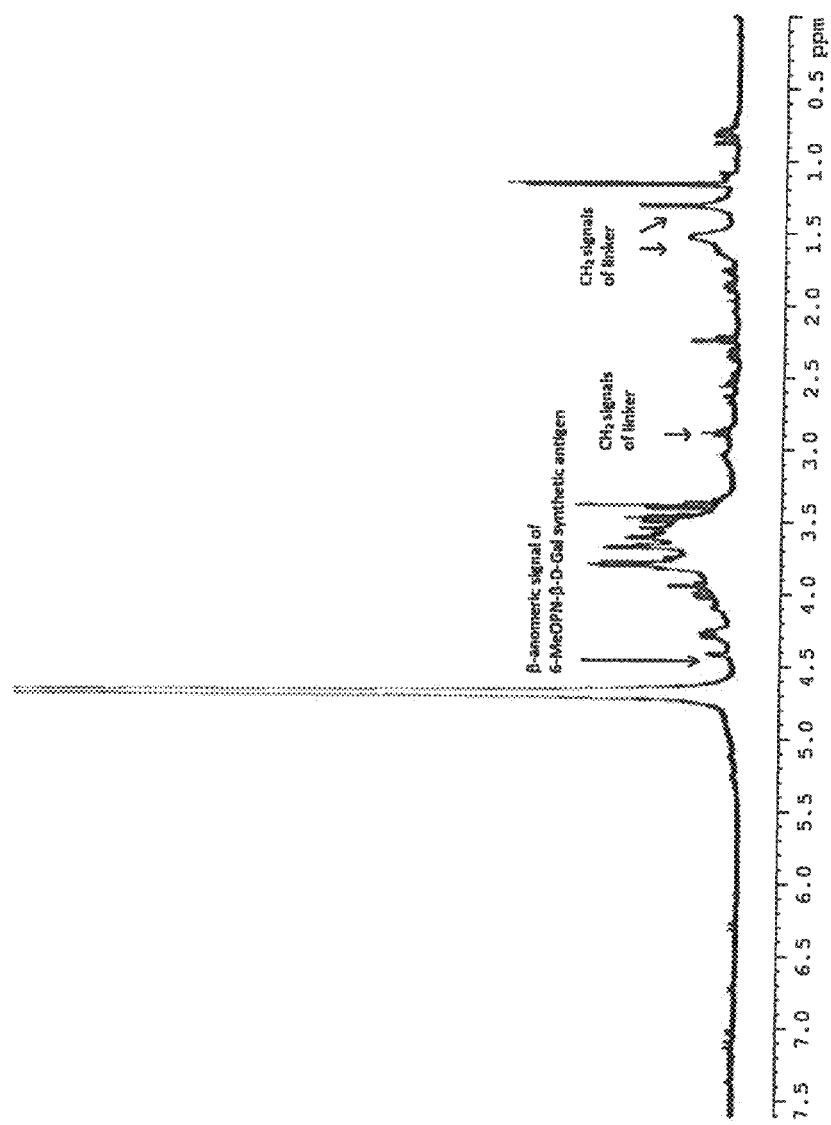
FIG. 17 depicts $^1$H NMR of the synthetic polymeric construct of FIG. 15 showing the successful attachment of the *C. jejuni* MeOPN-6-Gal synthetic antigen to the modified (oxidized) starch polymer. X axis is ppm. The arrow at approximately 4.5 ppm indicates the β-anomeric signal of 6 MeOPN-β-D-Gal synthetic antigen; the remaining arrows indicate CH$_2$ signals of the linker.

The starch-sugar conjugation product (4 mg) was conjugated with CRM$_{197}$ (4 mg) in 0.1 M borate buffer (5 ml), pH 9. Sodium cyanoborohydride (40 mg) was added and the reaction mixture was stirred for 1 day at RT and 2 days at 37° C. The conjugate was then dialyzed against running water (1000 Da) for 2 days and then lyophilized. The resulting synthetic conjugate was characterized using Western gel and immunoblotting and 1H NMR as provided in FIGS. 16 and 17, respectively. Briefly, for the immunoblot, the synthetic conjugate was electrophoresed on a 12.5% polyacrylamide gel in duplicate. Part of the gel was stained and the other part was transferred to nitrocellulose using a Trans-Blot® Turbo™ System (BioRad Laboratories, Hercules, Calif.)

and immunodetected with rabbit hyperimmune sera to formalin killed whole cells of *C. jejuni* strain 81-176 (final dilution 1:500 in TBST which is 20 mM Tris, pH 7.4, 0.425 N NaCl, 0.05% Tween 20). The filter was reacted with primary antibody overnight and then washed. Secondary antibody was goat anti-rabbit IgG (final dilution 1:50,000 in TBST). After washing, the filter was detected with Supersignal West Femto Maximum Sensitivity Luminescence Substrate (Thermo-Pierce, Rockford, Ill.) and images were recorded on a Bio-Rad gel imaging system.

The synthetic polymeric conjugate depicted in FIG. 18 was similarly prepared using conventional methods and reagents, and conjugated to a protein carrier. In contrast to the conjugate depicted in FIG. 15, the synthetic construct depicted in FIG. 18 comprises not only multiple MeOPN-6-Gal monosaccharides, but also multiple MeOPN-2-Gal and MeOPN-1-Fru monosaccharides. As described above, the various monosaccharides are chemically associated (conjugated) using a starch backbone. The sugar is chemically equipped with a linker that can serve as a bridge between the sugar and the starch. A carrier protein is affixed to the construct.

Example 8

Identification of MeOPN-4-Gal and Modulation of Serum Resistance by Phase Variable Changes in the Position of O-Methyl Phosphoramidate Modifications on the Polysaccharide Capsule of *Campylobacter jejuni* Strain 81-476

Figure 19A:
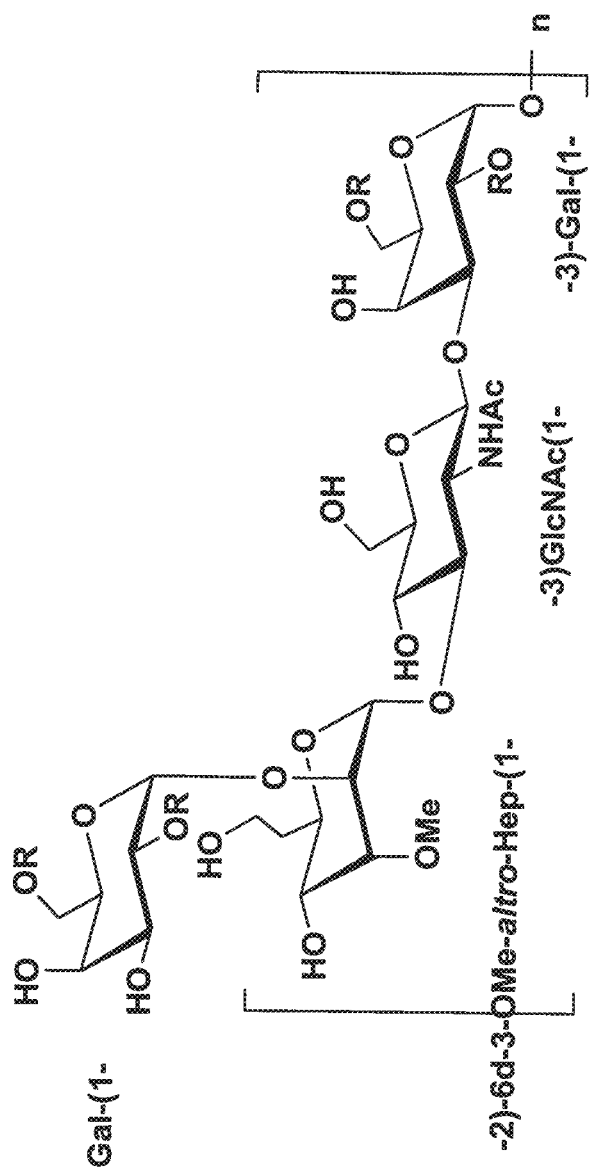
FIG. 19A depicts the structure of two repeats of the 81-176 capsular trisaccharide. The position of MeOPN-2-Gal and MeOPN-6-Gal is indicated. R═H or MeOPN.
Figure 19B:
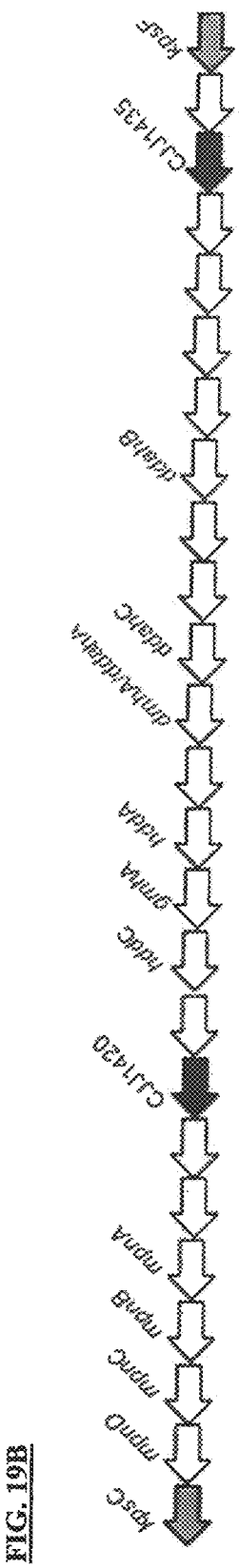
FIG. 19B depicts a cartoon of genes in the variable CPS locus of 81-176. The variable CPS locus of 81-176 maps between kpsC (CJJ81176_1413c) and kpsF (CJJ81176_1437c) shown in grey and encompasses 22 genes. Genes of known function are labeled. Those genes that involved in synthesis of MeOPN are labeled as mpnA-D (Maue, A C et al. 2013 Infect Immun. 81:665-672) and the remaining genes labeled are involved in heptose synthesis. Genes in black represent the two putative MeOPN transferases, CJJ81176_1420 and CJJ81176_1435.

FIG. 19(A) depicts the structure of two repeats of the 81-176 capsular trisaccharide with the position of MeOPN-2-Gal and MeOPN-6-Gal indicated (R═H or MeOPN.) FIG. 19(B) depicts a cartoon of genes in the variable CPS locus of 81-176. The variable CPS locus of 81-176 maps between kpsC (CJJ81176_1413c) and kpsF (CJJ81176_1437c) shown in grey and encompasses 22 genes. Genes of known function are labeled. Those genes that involved in synthesis of MeOPN are labeled as mpnA-D (Maue, A C et al. 2013 Infect Immun. 81:665-672) and the remaining genes labeled are involved in heptose synthesis. Genes in black represent the two putative MeOPN transferases, CJJ81176_1420 and CJJ81176_1435.

Data presented below confirm the existence of a third site of MeOPN modification on the *Campylobacter jejuni* strain 81-176 CPS at the 4 position of galactose (MeOPN-4-Gal), and show that the CJJ81176_1420 gene encodes the transferase responsible for this activity. Data also indicate that MeOPN appears to mediate resistance to complement by blocking binding of anti-glycan antibodies present in normal human sera (NHS), and MeOPN-4-Gal appears to be the major modification responsible for resistance to complement-mediated killing, although the CJJ81176_1420 gene appears to be primarily in an "OFF" configuration during in vitro culture.

Materials and Methods

Strains and growth conditions: All work was done in the 81-176 strain of *C. jejuni*. Mutants of this strain used in this example are listed in Table 1. *R, homopolymeric tract of G's that is subjected to phase variation was repaired as described herein.

TABLE 1

Capsular mutants of 81-176

| Strain no. | Genotype | Strain Background | Reference |
|---|---|---|---|
| 3390 | mpnC::cat | wildtype | Maue, A. C., et al. (2013) Infect Immun. 81: 665-672. |
| 3477 | CJJ1420::aph3 | wildtype | Unpublished |
| 3498 | CJJ1420::aph3, hipO::CJJ1420R*+cat | 3477 | Unpublished |
| 3636 | CJJ1435::cat | wildtype | Unpublished |
| 3637 | CJJ1435::cat, astA::CJJ1435R*+aph3 | 3636 | Unpublished |
| 3479 | CJJ1420::aph3, CJJ1435::cat | 3477 | Unpublished |
| 3501 | hipO::CJJ1420R*+cat | Wildtype | Unpublished |
| 3718 | hipO::CJJ1420R*+cat, CJJ1435::apr | 3501 | Unpublished |

*C. jejuni* for strain construction was routinely cultivated on commercially available Mueller Hinton (MH) agar at 37° C. under microaerobic conditions. Media was supplemented with antibiotics as needed for mutants with antibiotic resistance markers (Yao, R. et al. 1993 Gene 130:127-130.) Bacterial cells for capsule extraction are grown in porcine Brain Heart Infusion broth (Difco, Franklin Lakes, N.J.) at 37° C. In a microaerophilic environment. The bacterial cell mass may be collected and frozen and lyophilized for subsequent extraction and purification of CPS/LOS.

The extraction of carbohydrates from the whole cell mass uses hot water/phenol extraction (Westphal O, Jann K. General Polysaccharides: Methods in Carbohydrate Chemistry. 1965; 5:83-91; Chen Y-H et. al., Carbohydrate Research. 2008; 343:1034-1040.) After crushing the lyophilized whole cell pellet, the resulting powder is added to a round bottom flask. A predetermined amount of water is then added to the reaction flask. Phenol is added to the flask after one hour of stirring at 70-75° C. The solution is then stirred for an additional 6-7 hours at 70-75° C., and transferred immediately to ice after the allotted time (Westphal O, Jann K. General Polysaccharides: Methods in Carbohydrate Chemistry. 1965; 5:83-91; Chen Y-H et al., Carbohydrate Research. 2008; 343:1034-1040.) The reaction mixture separates into two layers; water and phenol. Carbohydrates are found in the aqueous layer, and the lipophilic components of the cell will remain in the phenol. The aqueous layer is collected and replaced with fresh deionized water (dH$_2$O). The reaction is repeated for 2 additional days. The collected aqueous layers will still contain small amount of the phenol, and these molecules can be removed through the use of dialysis. The aqueous layer is placed under running dH$_2$O dialysis overnight in 1 kDa molecular weight cut-off (MWCO) bagging (Spectra/Por®, Spectrum Laboratories, Rancho Dominguez, Calif.). The CPS is retained inside the 1 kDa MWCO bagging due to its larger molecular weight. The dialyzed layer is frozen and lyophilized for further purification and analysis. The product from the freeze-dried aqueous layer is purified further. In the case *C. jejuni*, the recovered mass is ultracentrifuged at 15000 rpm for 6 hours to remove the LOS from the aqueous CPS. The pellet of LOS and aqueous CPS are both frozen and lyophilized. The aqueous CPS product is then purified further by use of a Bio-Gel® polyacrylamide P2 column (Bio-Rad, Hercules, Calif.) which uses size exclusion as separation. The collected fractions may be used in subsequent experiments.

Oligonucleotide primers. All oligonucleotide primers used are listed in Table 2 and were synthesized by Life Technologies (Frederick, Md.)

TABLE 2

Primers

| Primer name | Sequence | SEQ ID NO. |
|---|---|---|
| pg12.13 | GGAATTCGATGATTATTTTATAGATATTGGTGTGCCTGAGG | 1 |
| pg12.14 | CCCTCGAGGGGATATTACTATCGACTATATCGTAACTATTACAACC | 2 |
| pg12.25 | CCAGCTGAACTTGCTTGGGAGATG | 3 |
| pg12.26 | GGGATATTACTATCGACTATATCGTAACTATTACAACC | 4 |
| pg10.07 | GTGTGATGTGGTGGTTACGTTGAATTCGGG | 5 |
| pg10.08 | CTCAAATCTATAGTAAGTGGCATGATTAACATGCCAAGC | 6 |
| pg14.67 | CATCCTTATCCTTCATTACTTGATCC | 7 |
| pg14.68 | CGTGGAACATGTTTATTTATCATATGC | 8 |
| pg12.31 | CATGAAAATCCTGAGCTTGGTTTTGATG | 9 |
| pg12.32 | GTATTTTAAAACTAGCTTCGCATAATAAC | 10 |
| pg12.33 | GCGCCCATGGGTTAACGGAGCACTTCCATGACCACCTCTTCC | 11 |
| pg12.34 | GCGCCCATGGTCTAGAAGATCTCCTATTTATGCTGCTTCTTTGCTTCTGG | 12 |
| pg12.29 | CGGGATCCAAAGGAGAAACCCTATGTATAACCCAAACTCAGC | 13 |
| pg12.30 | GGAATTCGTAAATCCCCTTGTTTCATATTGATTCCTTTCTCTAATTTTAAACAC | 14 |
| pg12.37 | GCTATGATTGAGTTTACAAACAATGGAGGAGGATATATAGCATTATTTAAAAAACTC | 15 |
| pg12.38 | GAGTTTTTAAATAATGCTATATATCCTCCTCCATTGTTTGTAAACTCAATCATAGC | 16 |
| pg14.35 | GGAATTCCTATATTATAAGATAATAACACAATTCGCCTCCTATG | 17 |
| pg14.03 | CGGGATCCAGGAGAAACCCTATGTATAACCCAAACTCAGC | 18 |
| pg14.09 | GCTATGATTGAGTTTACAAACAATGGAGGAGGATATATAGCATTATTTAAAAAACTC | 19 |
| pg14.10 | AGTTTTTTAAATAATGCTATATACCTCCTCCTTTGTTTGTAAACTCAATCATAGC | 20 |
| pg12.17 | ATGTATAACCCAAACTCAGCTATAGAAAGAG | 21 |
| pg15.13 | GAGAATTGAGGATACTATGTCCAGTTAATCC | 22 |
| pg15.14 | GCTTTCTCTCCTGTTCCATGGCCTCC | 23 |

NMR and Gas Chromatography-Mass Spectrometry (GC-MS) analyses: $^1$H, $^{13}$C and $^{31}$P NMR experiments were recorded using a Bruker AMX 400 spectrometer equipped with a CryoProbe™ (Bruker Corp., Billerica, Mass.) Experiments were run at 293K or 315K. Heteronuclear single quantum correlation spectroscopy (HSQC) and heteronuclear multiple bond correlation spectroscopy (HMBC) experiments were performed using Bruker TopSpin™ 3.0 software. Prior to analysis, samples were lyophilized with $D_2O$ (99.9%) three times. The HOD resonance at $\delta_H$ 4.821 was used as the internal standard for $^1$H experiments. A standard of TSP in $D_2O$ was used to establish a reference for the HOD signal. Orthophosphoric acid ($\delta_P$ 0.0) was used as the external reference for all $^{31}$P experiments.

Characterization of monosaccharides: Monosaccharides were characterized as alditol acetate derivatives. The CPS was first digested with 4M trifluoroacetic acid at 105° C. and then the monomers were reduced with NaBD$_4$ in water overnight at room temperature. The alditols were acetylated with acetic anhydride at 105° C. The resulting alditol acetates were extracted using dichloromethane and analyzed by GC-MS in a ThermoFinigan PolarisQ Ion Trap equipped with a DB-17 capillary column (Thermo Fischer Scientific, Waltham, Mass.)

Rabbit polyclonal antisera: Rabbit hyperimmune polyclonal antibodies were generated against three batches of HS23/36-CRM$_{197}$ conjugate vaccines: CCV (Monteiro, M A et al. 2009 Infect. Immun. 77:1128-1136), DB4, and CJCV1 (Dalton Pharma, Toronto Canada). The conjugate vaccine CCV was produced as provided in Monteiro, M A et al. 2009 Infect. Immun. 77:1128-1136. Briefly, C. jejuni strain 81-176 was grown and the capsule isolated as described above. The isolated CPS of 81-176 was conjugated to the carrier protein CRM$_{197}$ by reductive amination between aldehydes strategically created at the nonreducing end of the CPS, and accessible amines of CRM$_{197}$. The CPS:CRM$_{197}$ ratio used was 2:1 by weight. A rabbit polyclonal serum against formalin fixed whole cells of 81-176 has been reported previously (Bacon, D J et al, 2001 Mol. Microbiol. 40:769-777).

PCR: All PCR products generated for cloning or sequence analysis were amplified using Phusion® high fidelity polymerase (New England Biolabs, Ipswich, Mass.) All other PCRs used Taq polymerase (Applied Biosystems/Life Technologies (Foster City, Calif.)

Anti-CPS ELISAs to determine levels of MeOPN on CPS-CRM$_{197}$ conjugates: To determine the relative levels of MeOPN on the three CPS-CRM$_{197}$ conjugates, the conjugates were normalized based on total CPS content and serially diluted on MaxiSorp Nunc® plates (Sigma-Aldrich, St. Louis, Mo.) In carbonate coating buffer overnight at 4° C. Plates were washed with PBST and blocked with BSA in PBST for 1 hr at 37° C. To detect MeOPN-6-Gal, plates were washed and DB3 monoclonal antibody was diluted in blocking buffer and incubated for 1 hr at 37° C. Goat anti-mouse IgG-HRP (Thermo-Scientific was added after washing and incubated for 1 hr at 37° C. Plates were washed and 100 µl of tetramethylene benzidine (TMB, eBioscience, San Diego, Calif.) substrate was added for 10 min before 100 µl 1M $H_2SO_4$ was added to stop the reaction. The OD was read at 450 nm.

Generation of hybridomas: Splenocytes from BALB/c mice immunized subcutaneously with a CPS 81-176-CRM$_{197}$ conjugate (three times at 4 week intervals) were fused with SP2/0 myeloma cells (Sp2/0-Ag14; ATCC CRL-1581, ATCC, Manassas, Va.) to generate hybridomas according to Nyame, A K et al. 2003 Exp. Farasitol. 104:

1-13. Briefly, splenocytes and SP2/0 cells were fused in the presence of polyethylene glycol and mixed with peritoneal macrophages derived from a non-immunized BALB/c mouse in hybridoma media (Iscoves media containing 20% FBS, 2×HAT (200 mM hypoxanthine, 0.8 mM aminopterin, 32 mM thymine), OPI (1 mM oxaloacetate, 0.45 mM pyruvate and 0.2 U/mL insulin), 4 mM glutamine and IL-6 (10 ng/ml)). Fused cells were immediately plated on eight 96-well cell culture plates and incubated at 37° C. In a 5% $CO_2$ atmosphere for 2 weeks. Hybridomas were selected by screening culture supernatants from each well by ELISA using BSA conjugates of CPS from both 81-176 and the mpnC mutant as antigenic targets.

Production and purification of monoclonal (mAb) DB3: A single cell hybridoma clone was gradually expanded into 16 T-150 flasks, while weaning down to 2.5% FBS in Iscove's media. Cells were transferred into 2 L roller bottles containing 1 L of serum free media (SFM), and were cultured at 37° C. In 5% $CO_2$ for 4 weeks. The mAb DB3 in SFM was purified over a MEP-HyperCel™ column according to manufacturer's instructions (Pall Life Sciences Corp., Port Washington, N.Y.) Eluted antibodies were dialyzed into TBS (0.05 M Tris/0.15 NaCl, pH 7.6), and protein content was determined by BCA assay. Aliquots were stored at −80° C. for further characterization and use. Isotype was determined using a Pierce™ Rapid Isotyping Kit (Cat. No 26178; Thermo Fischer Scientific, Waltham, Mass.)

Flow cytometry: 81-176 strains were grown for 20 hours on MH agar, and the cells were harvested into 5 mL of PBS and filtered through a 1.2 micron filter. The resulting suspension was adjusted to an $OD_{600}$ 0.1, and one ml was spun down at 12000 g for 2 min. Pellets were resuspended in 0.5 ml 4% formaldehyde and incubated on a rotator for 10 min at room temperature. Cells were centrifuged, washed twice in ice-cold PBST, and resuspended in 100 microliters of a 1:50 dilution of serum from hyperimmune rabbits immunized with a conjugate antibody or DB3 monoclonal antibody at a final concentration of 112 µg/ml and incubated for 30 minutes at 4° C. Suspensions were washed twice with ice cold PBST and then incubated with donkey anti-rabbit IgG Alexa Fluor® 647 (Biolegend, San Diego, Calif.) for the hyperimmune sera or rat anti-mouse IgG1 PE (Southern-Biotech, Birmingham, Ala.), and incubated for 30 minutes at 4° C. The suspensions were washed twice for ice cold PBST and resuspended in 0.5 ml PBST and read on a ED FACSCanto™ (BD Biosciences, San Jose, Calif.) Data were analyzed using FlowJo (TreeStar, Ashland, Oreg.).

Mutation of CJJ81176_1420: CJJ81176_1420 was cloned into pPCR-Script (Stratagene, La Jolla, Calif.) using primers pg12.13 and pg12.14 that introduced EcoR and XhoI sites, respectively. This plasmid was subjected to transposon mutagenesis using Tnp Km (Epicentre, Madison, Wis.) and individual Km$^r$ transposon insertions were sequenced with primers internal to the transposon to determine the site of insertion. A non-polar transposon insertion at bp 367 of the 1779 bp gene was used to electroporate 81-176 to Km$^r$ using methods previously described (Yao, R. et al. 1993 Gene 130:127-130.) The putative mutation was confirmed by PCR using primers pg12.25 and pg12.26 that bracket the insertion point of the kanamycin gene and this mutant was called strain 3477.

Mutation of CJJ81176_1435: CJJ81176_1435 was cloned into pPCR-Script (Stratagene, La Jolla, Calif.) using primers pg10.07 and pg10.08. The cat cassette from pRY109 (Yao, R. et al. 1993 Gene 130:127-130) was cloned into a unique NcoI site located at bp 747 of the 1813 bp gene. Clones were partially sequenced to determine orientation of the cat cassette and one in which the gene was inserted in the same orientation as CJJ81176_1435 was used to electroporate 81-176 to Cm$^r$. Putative clones were confirmed by PCR using pg14.67 and pg14.68 that bracket the NcoI site of insertion, and the resulting mutant was called strain 3636.

Construction of a double mutant in both putative MeOPN transferases: Strain 3477, CJJ81176_1420::aph3, was electroporated to Cm$^r$ with the same plasmid used to generate strain 3636, thus generating a double mutant, strain 3479 (see Table 1).

Construction of a hipO insertion vector: The hipO gene of 81-176 (CJJ81176_1003), encoding the non-essential enzyme benzoylglycine amidohydrolase, was cloned into pPCR-Script (Stratagene, La Jolla, Calif.) using primer set pg12.31 and pg12.32. A unique XbaI site was introduced in the center of the hipO gene by inverse PCR with primer sets pg12.33 and pg12.34. This plasmid was called pCPE3490.

Construction of strains expressing repaired alleles of CJJ81176_1420 and CJJ81187_1435: The CJJ1420::aph3 mutant was complemented with a repaired allele as follows. The wildtype CJJ81176_1420 gene was PCR amplified using primers pg12.29 and pg12.30, which introduced BamHI and EcoR1 sites, respectively, and the resulting amplicon was cloned into BamHI and EcoRI digested pCPE108, which contains the $\sigma^{28}$ promoter from flaA cloned between the XbaI and BamHI sites of pBluescript (Ewing, C. P., et al. (2009) J. Bacteriol. 191:7086-7093). The phase variable G9 tract within CJJ81176_1420 was repaired by mutagenesis (Quick Change Site Directed Mutagenesis Kit; Agilent Technologies, Germantown, Md.) such that the G9 was changed to GGAGGAGGA using primers pg12.37 and pg12.38. The entire insert was moved as an EcoR1-NotI fragment into pBluescript (Agilent Technologies, Germantown, Md.) and a SmaI-ended cat cassette from pRY109 (Yao, R. et al. 1993 Gene 130:127-130) was inserted into the EcoRV site 3' to the repaired CJJ81176_1420 gene. The entire construction ($\sigma^{28}$-CJJ81176_1420+cat) was PCR amplified with forward and reverse primers and cloned into the unique XbaI site within the hipO gene in pCPE3490 (described above) that had been blunted. This construction, called pCPE3494, was used to electroporate strain 3477, the CJJ81-176_1420::cat mutant, to Km$^R$, generating strain 3498.

The CJJ1435::cat mutant was complemented using a similar approach. Plasmid pCPE108 was modified to contain an aph3 gene at the XhoI site in the polylinker, generating pCPE3583. CJJ81176_1435 was PCR amplified using primers pg14.35 and pg14.03, which introduced BamHI and EcoRI sites, respectively, and cloned into BamHI and EcoR1 digested pCPE3583. The phase variable G9 tract located within the coding region of CJJ81176_1435 was subjected to site-directed mutagenesis as described above using primers pg14.09 and pg14.10. The repaired CJJ81176_1435 gene and the adjacent aph3 gene were PCR amplified using forward and reverse primers and cloned into an EcoRV site on a plasmid containing the astA of strain 81-176, as previously described (Ewing, C. P., et al. (2009) J. Bacteriol. 191:7086-7093; Yao, R. and Guerry, P. (1996) J. Bacteriol. 178:3335-3338). This plasmid was used to electroporate the CJJ81176_1435 mutant, strain 3636, to Km$^r$, generating strain 3637.

A C. jejuni strain was also constructed that overexpressed CJJ81176_1420 in a CJJ81176_1435 mutant background for NMR studies. Plasmid pCPE3494 that was used to construct the complement of the CJJ81176_1420 mutant (described above) was electroporated into wildtype 81-176 to generate strain 3501. An apramycin cassette from plasmid pAC1

(Cameron, A. and Gaynor, E. C. (2014) Plos One 9, e95084. doi:10.1.371/journal.pone.0095084) was inserted into the unique NcoI site in the clone of CJJ81176_1435 described above. This clone was electroporated into strain 3501 to generate strain 3718 (see Table 1).

Anti-CPS ELISAs to determine the anti-CPS response in hyperimmune rabbits or Normal Human Sera (NHS): To determine the anti-CPS response in hyperimmune rabbits or NHS, Carbo-BIND™ plates (Corning®, Corning, N.Y.) were coated with 100 µl of oxidized CPS from wildtype, 3390, 3477 or 3636 strains (2 µl/ml in sodium acetate buffer (pH 5.5) for 1 hr at room temperature according to the manufacturer's instructions.) Plates were washed with 1×PBS-(0.05% casein for NHS) for 1 hr at 37° C. and washed again with PBST. All sera were serially diluted in blocking buffer in duplicate and incubated for 1.5 hr at 37° C. After washing, HRP-conjugated goat anti-rabbit IgG (Sigma-Aldrich, St. Louis, Mo.) was diluted in 5% FCS-PBST and added at 100 µl per well for 1 hr at 37° C. before washing. ABTS-peroxidase substrate (KPL, Gaithersburg, Md.) for rabbit, or 3,3',5,5'-tetramethylbenzidine (TMB) for NHS, were used as a detection reagent and the $OD_{405}$ or $OD_{450}$, respectively, was measured. The mean OD of negative control wells (coating buffer alone)+3 standard deviations was used to determine the endpoint titer.

Phase variation of MeOPN transferases: The variable regions of the two MeOPN transferases were PCR amplified with pg12.17, which maps to the conserved region, and pg15.13, which is specific for CJJ81176_1420 or pg15.14, which is specific for CJJ81176_1435. The resulting PCR products were purified and sequenced with pg.12.17.

Complement killing: For serum resistance assays, bacterial strains were grown in biphasic MH cultures for 18 to 20 h at 37° C. Pooled normal human sera (NHS) were purchased from Sigma Aldrich (St. Louis, Mo.) and a single lot was used for all experiments. Assays were done as described in Maue, A. C., et al. (2013) Infect Immun. 81: 665-672, except that a range of NHS was used. Briefly, cultures (18 h old) of C. jejuni grown in MH biphasic media were washed and adjusted to an $OD_{600}$ of 0.1 in minimal essential medium (MEM). Aliquots (100 µl) were added to wells of a 24-well plate containing 900 µl of prewarmed MEM supplemented with different percentages NHS and incubated under microaerobic conditions at 37° C. The percentage of survivors was determined by serial dilution onto MH agar plates. Assays were repeated between 2-9 times for each strain. Statistics were done using GraphPad Prism (La Jolla, Calif.)

Results

MeOPN modifications on the 81-176 CPS: Using mass spectrometry we previously detected a non-stoichiometric MeOPN unit at the 2 position of galactose (MeOPN-2-Gal) in 81-176 CPS (Kanipes, M. I., et al., (2006) J. Bacteriol. 188:3273-3279), with a $^{31}P$ resonance similar to that in FIG. 20A (peak Y). Here, we confirmed this MeOPN92-Gal linkage by NMR (FIG. 26A) through the detection of a cross-peak between the $^{31}P$ resonance Y ($\delta_P$ 14.45) of MeOPN and H-2 ($\delta_H$ 4.52) of the galactose unit in a $^1H$-$^{31}P$ correlation experiment.

In some 81-176 CPS preparations, albeit of lower intensity, the $^{31}P$ NMR spectrum displayed an additional resonance (FIG. 20B) at $\delta_P$ 14.15 (designated peak Z). A similar peak (data not shown) was also observed in the $^{31}P$ NMR of mutant in CJJ81176_1420, called strain 3477 (see Table 1), which exhibited a cross-peak (FIG. 26B) between the phosphorous of MeOPN and H-6 resonances of some of the CPS galactose units, which resonated very near the methyl resonances of MeOPN ($\delta_H$ 3.75 to 3.81). The NMR data suggested that peak Z in 81-176 wildtype and strain 3477 (the mutant in CJJ81176_1420) corresponded to a non-stoichiometric placement of MeOPN at position 6 of galactose (MeOPN-6-Gal), consistent with the data using synthetic MeOPN-6-Gal. The $^{31}P$ NMR spectrum of strain 3636 (FIG. 20C), a mutant in CJJ81176_1435, did not show either peak Y or peak Z, but yielded a previously unseen phosphorous resonance at $\delta_P$ 14.73 (designated peak X in FIG. 20C).

Figure 27:
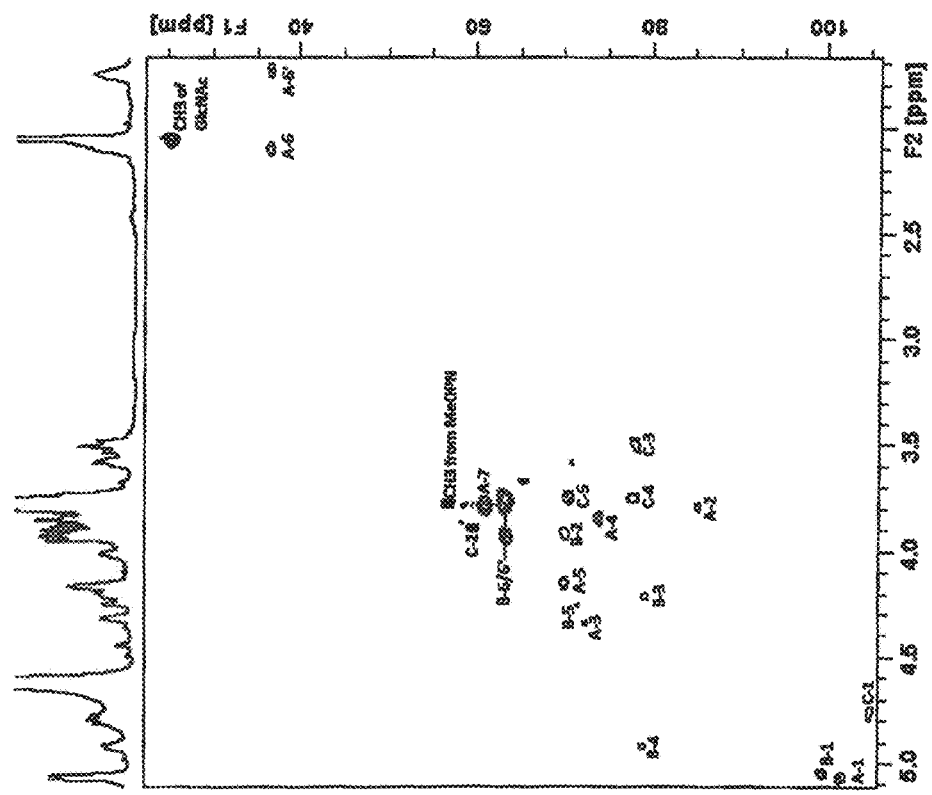
FIG. 27 depicts the spectrum of a $^1$H-$^{13}$C HSQC experiment showing the assignment of $^1$H and $^{13}$C resonances of the CPS from mutant 3718.

A 2D $^1H$-$^{31}P$ NMR experiment showed a connection between peak X and a proton resonance at $\delta_H$ 4.88 (FIG. 27). Since the $^{31}P$ NMR spectrum from a double mutant in both transferases (strain 3479) showed no MeOPN resonances (data not shown), this activity must be encoded by CJJ81176_1420. A new strain was constructed, called strain 3718, for use in additional structural analyses in which a repaired, overexpressed allele of CJJ81176_1420 was introduced into strain 3636, the CJJ81176_1435 mutant (see Materials and Methods and Table 1).

Characterization of the capsule and MeOPN linkage in C. jejuni strain 3718: Sugar composition and linkage analysis of strain 3718 CPS revealed that, as in 81-176 wild-type CPS, 3-substituted Gal and 3-substituted GlcNAc were part of the trisaccharide repeating block. However, the majority of the heptose in 3718 CPS was present as the non-methylated 2-substituted 6-deoxy-altro-heptose (6d-altro-Hep), in place of the 2-substituted 6-deoxy-3-O-methyl-altro-heptose derivative typically found in 81-176 wild-type CPS.

Figure 26:
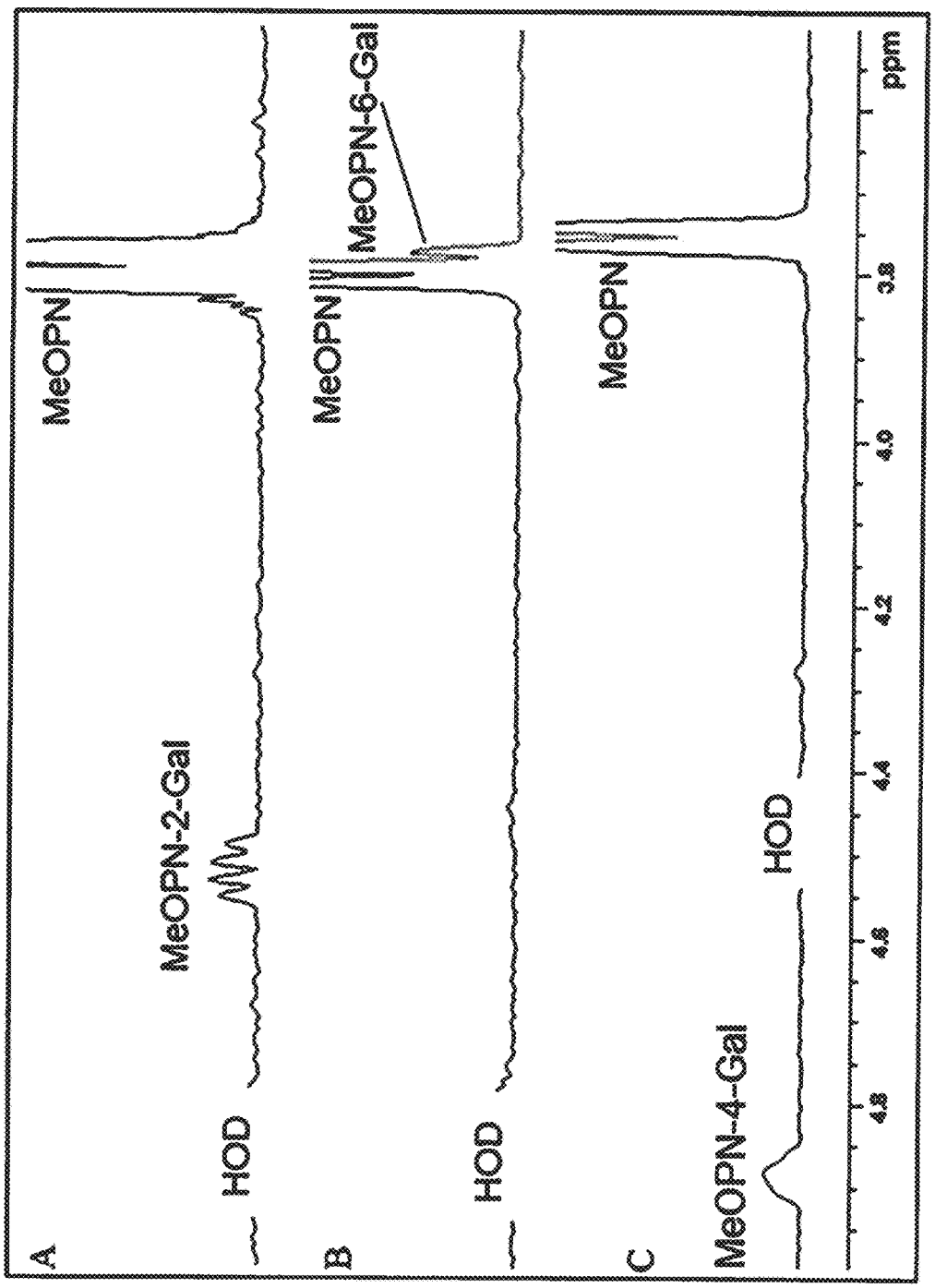
FIG. 26 depicts 1D slices obtained from 2D $^1$H-$^{31}$P HMBC NMR experiments showing the attachment of MeOPN to positions 2 (panel A; 293K) and 6 of Gal (panel B; 293K) in wild-type 81-176 CPS, and identifies the previously unidentified CPS position as attachment of MeOPN to position 4 of Gal in mutant CJJ81176_1435 CPS (panel C; 315K).

A more noteworthy structural deviation of the strain 3718 CPS was revealed by $^{31}P$ NMR spectroscopy, which displayed the resonance X at $\delta_P$ 14.72 (FIG. 20C). This $^{31}P$ resonance did not belong to the previously characterized MeOPN substitutions at positions 2 and 6 of Gal and thus pointed towards the fact that strain 3718 produced a CPS with another MeOPN substitution. The characterization of this new MeOPN moiety, MeOPN-4-Gal, is described in more detail in Example 9. Briefly, an accompanying 2D $^1H$-$^{31}P$ heteronuclear correlation (HMBC) experiment revealed a new inter-connectivity between the new MeOPN $^{31}P$ resonance at 14.72 ppm and a CPS $^1H$ resonance at 4.92 ppm (FIG. 26C; compare with FIG. 21C). Using 1D $^1H$-$^1H$ selective total correlation spectroscopy (TOCSY) methods (described in Example 9) the peak at $\delta_H$ 4.92 was irradiated revealing its connection to two ring proton resonances at $\delta_H$ 3.932 and $\delta_H$ 4.203 and to an anomeric resonance at $\delta_H$ 5.057. The anomeric resonance at $\delta_H$ 5.057 was in turn also irradiated, and its relationship to the ring resonances at $\delta_H$ 4.920, $\delta_H$ 4.203 and $\delta_H$ 3.932 was confirmed. These data, combined with a 2D $^1H$-$^1H$ COSY experiment (described in Example 9) resulted in the assignment of ring protons: $\delta_{H-1}$ 5.057, $\delta_{H-2}$ 3.932, $\delta_{H-3}$ 4.203, $\delta_{H-4}$ 4.920 and $\delta_{H-5}$ 4.250. The new MeOPN linkage thus involves position 4 of this ring system.

The monosaccharide ring carbons associated with the CPS trisaccharide repeat were assigned through 2D $^1H$-$^{13}C$ HSQC. FIG. 27 shows the three anomeric cross-peaks in which "A" represents the H-1/C-1 of 6d-α-altro-Hep, "B" that of H-1/C/1 of α-Gal and "C" that of H-1/C-1 of β-GlcNAc. Ring system A (6d-α-altro-Hep) carbons were located at δ 101.6 (A-1), 85.2 (A-2), 72.6 (A-3), 74.0 (A-4), 70.1 (A-5), 36.4 (A-6), 36.5 (A-6'), and 61.0 (A-7). The downfield carbon shift of A-2 at δ 85.2 agreed with the assignment of H-2 of the 2-substituted 6d-α-altro-Hep. Ring system B (α-Gal) carbons were assigned at δ 99.6 (B-1), 70.2 (B-2), 79.2 (B-3), 79.0 (B-4), and 71.6 (B-5). It could also be observed here that the C-3 of the 3-substituted α-Gal, at the downfield position of $\delta_C$ 79.2, matched H-3 ($\delta_{H-3}$ 4.203) of the previously described ring system containing MeOPN. Moreover, the associated C-4 at $\delta_C$ 79.0 ($\delta_{H-4}$ 4.920) of ring B ($\alpha$-Gal) was characterized as that carrying the MeOPN in 3718 CPS. The sole unit of the trisaccharide repeat in the β-configuration, that of 3-substituted β-Glc-NAc (ring system C) contained the C-1 at δ 105.0, C-2 at δ 59.7, C-3 at δ 78.0, and CH₃ group of the N-acetyl moiety δ 25.1.

MeOPN is the immunodominant epitope recognized by an anti-81-176 conjugate vaccine: Data indicate that anti-conjugate antibodies reacted with synthetic MeOPN-6-Gal. We examined reactivity of rabbit hyperimmune serum to an 81-176-CRM$_{197}$ conjugate vaccine, CJCV1, by ELISA to CPS from wildtype 81-176 or mutants. The results, shown in FIG. 28(A), indicated that the reaction of anti-CJCV1 antibody was strongest to the wildtype CPS (titer: $5.9 \times 10^6$). There was a marked reduction in titer to CPS purified from strain 3477, the mutant in CJJ81176_1420 expressing MeOPN-2-Gal and MeOPN-6-Gal (titer: $6.6 \times 10^5$) and an even greater reduction to CPS purified from strain 3636, the mutant in CJJ81176_1435 that expressed only MeOPN-4-Gal (endpoint titer 600). The difference in these latter two titers suggests either that there was very little MeOPN-4-Gal present in the immunizing conjugate vaccine or that the epitope was poorly immunogenic. Interestingly, the endpoint titer (8100) to CPS from 3390 (mpnC) that lacks all MeOPN was higher than that of 3636, suggesting that the presence of MeOPN-4-Gal prevented binding of antibodies to the polysaccharide chain. Thus, there are pre-existing antibodies to the capsular polysaccharide in NHS, most likely toward the rather common β-D-GlcpNAc-(1-3)-α-D-Galp linkage (altro-Hep is a rare sugar). The presence of MeOPN moieties prevents binding of these antibodies to the polysaccharide and thus, prevents complement mediated killing by the classical pathway. Since conjugate vaccines induce antibodies to the MeOPN-sugar moieties, these antibodies are predicted to induce complement mediated killing which would be critical for control of infection by an invasive pathogen. Since *C. jejuni* is an invasive organism, it would be expected to encounter high levels of NHS after invasion of epithelial cells in the intestine. Thus, the subpopulation that expresses CJJ81176_1420 and MeOPN-4-Gal would be more resistant to complement mediated killing.

Role of MeOPN in resistance to complement-mediated killing: Although van Alphen et al. reported that the population of their strain of 81-176 had the CJJ81176_1420 gene in an "OFF" configuration (van Alphen, L. B., et al., (2014) Plos One 9, e87051), they constructed a double mutant in both putative transferase genes and showed that the resulting mutant was sensitive to complement killing, consistent with earlier work with the mpnC mutant (Maue, A. C., et al. (2013) Infect Immun. 81: 665-672). When the variable regions of both MeOPN transferases were sequenced from the population of our version of strain 81-176, CJJ81176_1420 was also in an "OFF" configuration, while CJJ81176_1435 was "ON". However, when we determined the sequences of the variable regions of both transferases from 50 individual colonies of 81-176, 24% of the cells expressed CJJ81176_1420 in an "ON" configuration (12/50), while 82% of the cells expressed CJJ81-176_1435 in an "ON" configuration (41/50). Only 6% of the cells (3/50) were expressing both genes in "ON" configurations.

We compared complement killing (serum resistance) of strain 3477, the mutant in CJJ81176_1420, strain 3636, the mutant in CJJ81176_1435, and a double mutant lacking both transferases, strain 3479 (see Table 1) using increasing amounts of NHS in a serum survival assay. The results shown in FIG. 24 indicate that at all concentrations of sera, strain 3636 (the CJJ81176_1435 mutant expressing MeOPN-4-Gal), was significantly more resistant than wildtype, and that strain 3477 (the CJJ81176_1420 mutant expressing MeOPN-2-Gal and MeOPN-6-Gal), was significantly more sensitive than wildtype 81-176 at concentrations of NHS ranging from 5-15%. When both mutants were complemented with their respective, repaired alleles (strains 3637 and 3498), the serum resistance returned to levels comparable to that of wildtype. See FIG. 24. However, mutation of both MeOPN transferases (strain 3479) resulted in enhanced sensitivity over the CJJ81176_1420 mutant (strain 3477), and showed levels of sensitivity similar to that reported previously for another double transferase mutant (van Alphen, L. B., et al., (2014) Plos One 9, e87051) and for the mpnC mutant (Maue, A. C., et al. (2013) Infect Immun. 81: 665-672).

Phase variation of MeOPN transferases: The serum killing data suggested that expression of MeOPN-4-Gal enhanced serum resistance. All aliquot of an overnight culture of 81-176 was plated for single colonies on Mueller Hinton (MH) agar and another aliquot was exposed to 20% NHS for 1 h prior to plating for single colonies. The variable regions of CJJ81176_1420 and CJJ81176_1435 were sequenced from these individual colonies. The results indicated that without exposure to NHS, the CJJ81176_1420 gene was in the "ON" configuration in 9.5% of the 42 colonies and CJJ81176_1435 was "ON" in 90.5% of the colonies, consistent with the data described above. In contrast, after exposure to NHS, CJJ81176_1420 was "ON" in 100% of the 43 colonies sequenced and CJJ81176_1435 was "ON" in 53.5% of the 43 colonies sequenced. Without exposure to NHS, 4.8% of the colonies were "ON" for both genes, while after exposure to NHS, 53.5% of the colonies were "ON" for both genes. No colonies were "OFF" for both genes.

Figure 28B:
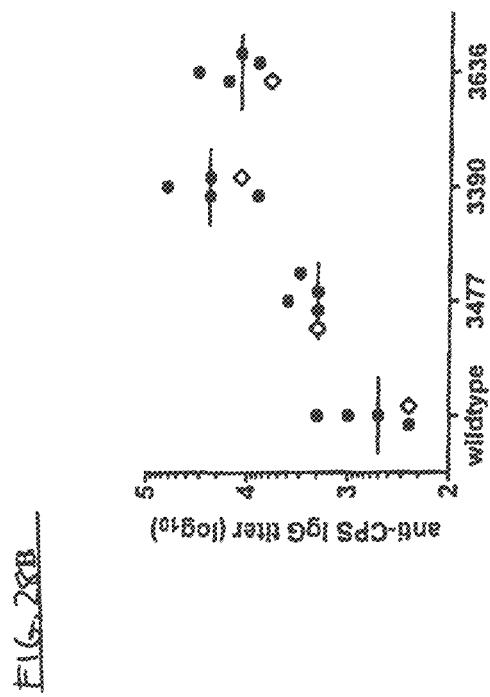
FIG. 28A and FIG. 28B depict the endpoint ELISA titers to CPS from wildtype 81-176 and mutants 3477, 3390, and 3636. The genotype of mutants in shown in Table 1.

Normal human serum contains antibodies to the 81-176 polysaccharide chain: ELISAs were performed on five commercially available human serum samples (Sigma Aldrich, St. Louis, Mo.), including the serum sample used in the serum killing experiments described above against CPS purified from 81-176 wildtype and the mutants. The results, shown in FIG. 28(B), indicated that there are preexisting antibodies in NHS to the 81-176 CPS (mean titer 800), but that the titer against CPS from the mpnC mutant was significantly higher (26,400), suggesting that MeOPN blocks attachment of pre-existing anti-glycan antibodies to the CPS. Generation of antibodies to MeOPN in conjugate vaccines can also induce serum bactericidal antibodies (SBA). Reactivity against CPS from the mutant strain 3477 was significantly higher than to wildtype CPS, consistent with loss of the MeOPN-4-Gal that is expressed in a minority of the cells in the population. The reactivity to strain 3636 CPS was higher than that of the strain 3477 CPS and slightly lower than that of the CPS from the mpnC mutant, strain 3390, consistent with loss of the MeOPN-2-Gal and MeOPN-6-Gal modifications that are expressed in the majority of the cells in the population.

Flow cytometry analyses using DB3: FIG. 22(B) shows that monoclonal DB3 bound to the surface of wildtype 81-176 as measured by flow cytometry, but did not bind to the mpnC mutant, as expected from the dot blotting studies (FIG. 22(A)). Binding was partially restored in strain 3391, the complement of the mpnC mutant. Similarly, DB3 did not bind to 3636, the mutant presumably lacking MeOPN-6-Gal, and binding was partially restored in 3637, the complement (FIG. 22(C)). However, binding of DB3 to 3477, the mutant lacking MeOPN-2-Gal, but retaining MeOPN-6-Gal, was reduced. Binding was enhanced in strain 3498, the complement (FIG. 22(D)).

Levels of MeOPN-6-Gal on conjugate vaccines modulate the immune response: When DB3 was used in an ELISA to measure the levels of MeOPN-6-Gal on three independently produced conjugate vaccines, differences in binding could be detected (FIG. 23A). CCV, the vaccine shown to protect non-human primates against diarrheal disease (Monteiro, M A et al. 2009 Infect. Immun. 77:1128-1136), showed the highest binding, DB4 was intermediate, and CJCV1 showed the lowest. Endpoint titers were determined by ELISA to capsules purified from wildtype 81-176 and the mpnC mutant for rabbit hyperimmune antisera against each of the three vaccines, as shown in FIG. 23B. Each vaccine elicited high titers of antibodies to the intact wildtype capsule (CCV: $6.6 \times 10^5$, DB4: $4.0 \times 10^6$, CJCV1: $5.9 \times 10^6$), but the titers against the mpnC capsule increased as the amount of MeOPN-6-Gal on each vaccine decreased (CCV: 100, DB4: 5400, CJCV1: 8100). Thus, the anti-polysaccharide response was lowest for CCV, intermediate for DB4 and highest for CJCV1. FIG. 23C-E shows the reactivity of each rabbit hyperimmune sera to the surface of wildtype and the mpnC mutant, CCV, with the highest amount of MeOPN-6-Gal, bound to the surface of wildtype 81-176 and no binding was detected to the mpnC mutant, 3390 (FIG. 23C). Binding was enhanced in the complement, strain 3391. Antibodies to conjugate DB4 bound to the surface of wildtype 81-176 and showed enhanced binding to the mpnC mutant compared to CCV (FIG. 23D). Finally, antibodies to CJCV1 bound equally well to wildtype and the mpnC mutant (FIG. 23E). None of the antibodies bound to the kpsM mutant. Thus, surface binding to the mpnC mutant was enhanced as the levels of MeOPN-6-Gal were reduced in the vaccines.

Discussion

The above data demonstrate that, in addition to the two previously reported sites of MeOPN modification, the 81-176 CPS can be modified at a third site, MeOPN-4-Gal. It appears that the transferase encoded by CJJ81176_1435 is bi-functional and is responsible for addition of MeOPN to both the 2 and 6-position of Gal, although modification at Gal-2 appears to be the preferred site based on the relative $^{31}$P-NMR signals. To our knowledge, this is the first report of a bi-functional MeOPN transferase. Mutation of CJJ81176_1435 not only resulted in loss of MeOPN-2-Gal and MeOPN-6-Gal, but resulted in appearance of a new $^{31}$P-NMR signal that was shown to correspond to MeOPN-4-Gal, which is encoded by CJJ81176_1420. When grown in vitro, most 81-176 cells expressed CJJ81176_1435 and only a subset of the population (9.5-24%) expressed CJJ81176_1420. The MeOPN-4-Gal $^{31}$-P NMR signal was initially observed in strain 3636, a mutant in CJJ81176_1435, and was characterized in a strain in which the CJJ81176_1420 transferase was overexpressed in this mutant background (strain 3718). Thus, the inability to transfer MeOPN to 2-Gal and 6-Gal appeared to enhance modification at the 4-position of Gal, perhaps due to an increased pool of MeOPN in the cell. Interestingly, the 3718 CPS also contained a majority of 6d-altro-Hep in place of the typical 3-O-methyl-6d-altro-Hep normally found in 81-176. The reason for this change remains uncertain, but a similar shift in Hep composition in the 81-176 CPS has been observed previously in a deep rough LOS mutant (Kanipes, M. I., et al., (2006) J. Bacteriol. 188:3273-3279).

Monoclonal DB3 appears to be specific for the MeOPN-6-Gal and/or MeOPN-2-Gal epitopes as determined by whole cell dot blot, and, consistent with this, bound to the surface of wildtype 81-176, but not to the CJJ81176_1435 or mpnC mutants by flow cytometry. (See FIG. 22). Interestingly, surface binding of DB3 was disrupted by mutation of CJJ81176_1420, suggesting that loss of MeOPN-2-Gal alters the secondary and/or tertiary structure of the CPS and reduces accessibility of DB3 to the surface of the cell. Although no studies have been reported, it is likely that the polysaccharide chain is decorated with MeOPN as it is being synthesized in the cytoplasm. Decoration of sugars with MeOPN is likely to affect changes in folding of the polysaccharide, which, after assembly on the cell surface, could also affect interactions between adjacent polysaccharide chains, thus affecting accessibility of the polysaccharide to antibodies and/or components of the complement cascade. This is consistent with our observations that loss of MeOPN-2-Gal in the CJJ81176_1420 mutant resulted in a significant reduction in resistance to complement mediated killing.

Complement mediated killing of *C. jejuni* has been reported to occur primarily by the classical pathway (van Alphen, L. B., et al., (2014) Plus One 9, e87051; Pennie, R. A., et al., (1986) Infect Immun. 52:702-706), and it is thought that the CPS likely functions to shield the cell from naturally occurring antibodies in NHS that cross-react with surface proteins. As discussed above, data presented here, however, suggest that MeOPN moieties also serve to protect the polysaccharide chain from pre-existing anti-glycan antibodies in NHS. The presence of MeOPN on the wildtype CPS inhibited binding of these antibodies as measured by ELISA compared to the CPS from strain 3390 lacking all MeOPN. Thus, strain 3636 lacking the major modifications at the 2 and 6-position of Gal bound more antibody than did the strain 3477 mutant lacking the minor MeOPN-4-Gal modification. However, strain 3477, lacking MeOPN-4-Gal, was more sensitive to complement mediated killing than wildtype, and strain 3636 lacking MeOPN-2-Gal and MeOPN-6-Gal was more serum resistant than wildtype. This is consistent with our observations that in the mutant of CJJ81176_1435, more MeOPN was put onto the 4-position of Gal. The pre-existing antibodies to the 81-176 polysaccharide chain in NHS are likely directed toward the rather common β-D-GlcpNAc-(1-3)-α-D-Galp linkage (altro-Hep is a rare sugar).

Figure 25:
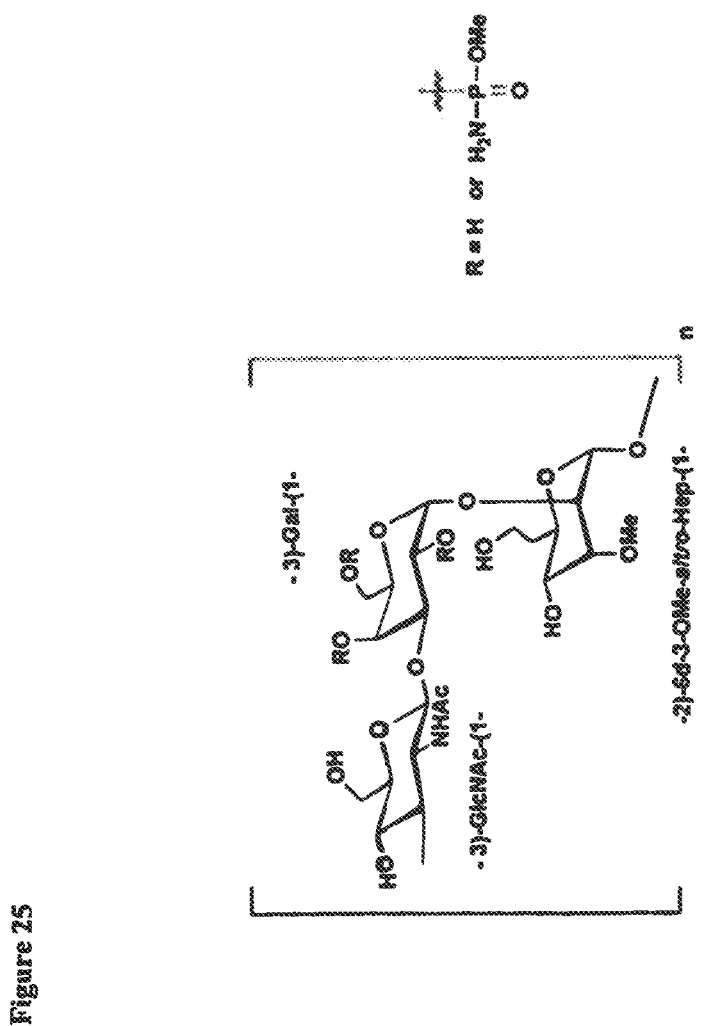
FIG. 25 is another depiction of structural repeats of the 81-176 polysaccharide CPS. As indicated, "n" represents the number of repetitions of the trisaccharide structure.

The importance of modification at the 4-position of Gal to serum resistance may relate to the fact that it is the closest site of modification to the GlcNAc-(1-3)-Gal linkage, and may be more effective at impeding binding of cross-reacting anti-glycan antibodies (FIG. 25). Similarly, the CPS of strain 3636, which expresses only MeOPN-4-Gal, had a lower ELISA titer to rabbit hyperimmune serum generated against an 81-176-CRM$_{197}$ conjugate than strain 3390, lacking all MeOPN. This also suggests that MeOPN-4-Gal blocked access of these antibodies to the polysaccharide.

Figure 28A:
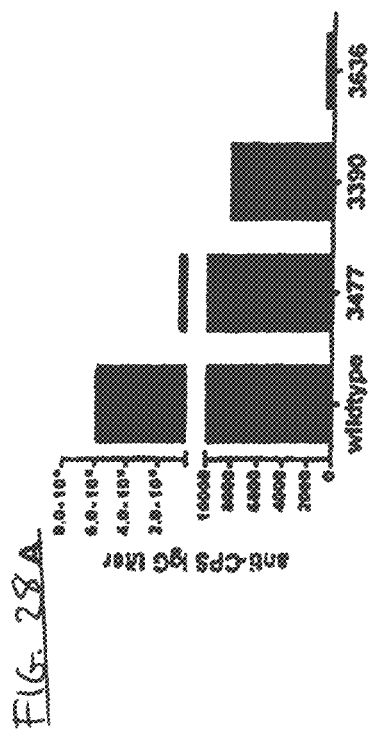

MeOPN modifications appear to be immunodominant epitopes on 81-176-CRM$_{197}$ conjugate vaccines. Thus, as shown in FIG. 28A, the endpoint titer of rabbit hyperimmune serum to a conjugate was >2 logs higher against wildtype CPS compared to CPS from the mpnC mutant, strain 3390. The immunodominance of MeOPN in conjugate vaccines appears to be comparable to the immunodominance of O-acetyl groups on the polysaccharide conjugates based on other bacterial pathogens (Calix, J. J., et al., (2011) J. Bacteriol. 193:5271-5278; Szu, S. C., et al. (1991) Infect. Immun. 59, 4555-4561; Fattom, A. L., et al. (1998) Infect. Immun. 66:4588-4592; Berry, D., et al. (2002) Infect. Immun. 70:3707-3713.) Non-stoichiometric modifications to sugars confer considerable heterogeneity to polysaccharide chains and can affect immunogenicity (King, M. R., et al. (2007) Trends Microbiol. 15:196-202). This heterogeneity is more complex for *C. jejuni*, since phase variation modulates both the level and position of MeOPN modifications. It has been reported that early in infection with *C. jejuni*, patient sera could induce low levels of complement mediated killing of multiple *C. jejuni* strains, but after 48 h of infection, patients developed higher-level serum bactericidal titers that were strain specific (Pennie, R. A., et al., (1986) Infect Immun. 52:702-706), an observation that may relate to MeOPN-sugar specific antibody responses. We are exploring the possibility that antibodies directed to MeOPN-sugar moieties in conjugate vaccines can induce serum bactericidal killing (see Example 14 below).

*C. jejuni* is characterized by variability of surface antigens (Parkhill, J., et al. (2000) Nature 403, 665-668). Phase variation of genes affecting lipoooligosaccharides, CPS, and flagella are well documented (Linton, D., et al (2000) Mol. Microbiol. 37: 501-514; Guerry, P., et al. (2001) Infect. Immun. 70:787-793; Hendrixson, D. R. (2006) Mol. Microbiol. 61: 1646-4659; Bacon, D. J., et al. (2001) Mol. Microbiol. 40:769-777). Recent studies have also shown that, in addition to phase variation, high frequency mutations can occur in genes that affect motility (Hendrixson, D. R. (2008) Mol. Microbiol. 70:519-536; Mohawk, K. L., et al. (2014) Plos One 9:2(e88043). doi:10.137/journal-.pone.0088043.) More recently, extensive variations, including insertions, deletions, and missense mutations of two genes, apt and purF, involved in stress responses of *C. jejuni* have been reported (Cameron, A., et al. (2015) mBio 6, e00612-00615). Different alleles of these two genes were associated with varying survival abilities under different stress conditions. Collectively, these observations support the suggestion that *C. jejuni* is a quasi-species containing multiple genotypes that can be selected based on their relative fitness in a particular environment. Phase variation of the MeOPN transferases in *C. jejuni* 81-176 provides another example of this bet-hedging phenomenon. The organism is generally considered to be relatively serum sensitive (Blaser, M. J., et al. (1985) J. Infect Dis. 151:227-235), and, when grown in vitro, the MeOPN transferases of strain 81-176 are in a configuration that does not allow for maximal complement resistance, meaning that the MeOPN-4-Gal transferase is predominantly in an "OFF" configuration. Data provided herein indicate that exposure to NHS selected for the minor population of cells that were expressing MeOPN-4-Gal, and thus could survive exposure to higher levels of NHS. Thus, the levels of serum resistance measured in vitro for a population may not reflect the levels of resistance that can be achieved in vivo. *C. jejuni* is an invasive pathogen and would be exposed to increasing levels of NHS as it invaded through the intestinal epithelium. Thus, it may be that only a sub-population of cells is capable of survival following invasion.

Example 9

Characterization of MeOPN-4-Gal Moiety in HS:23/36 CJJ1435::cm Mutant (Strain 3718)

Figure 20:
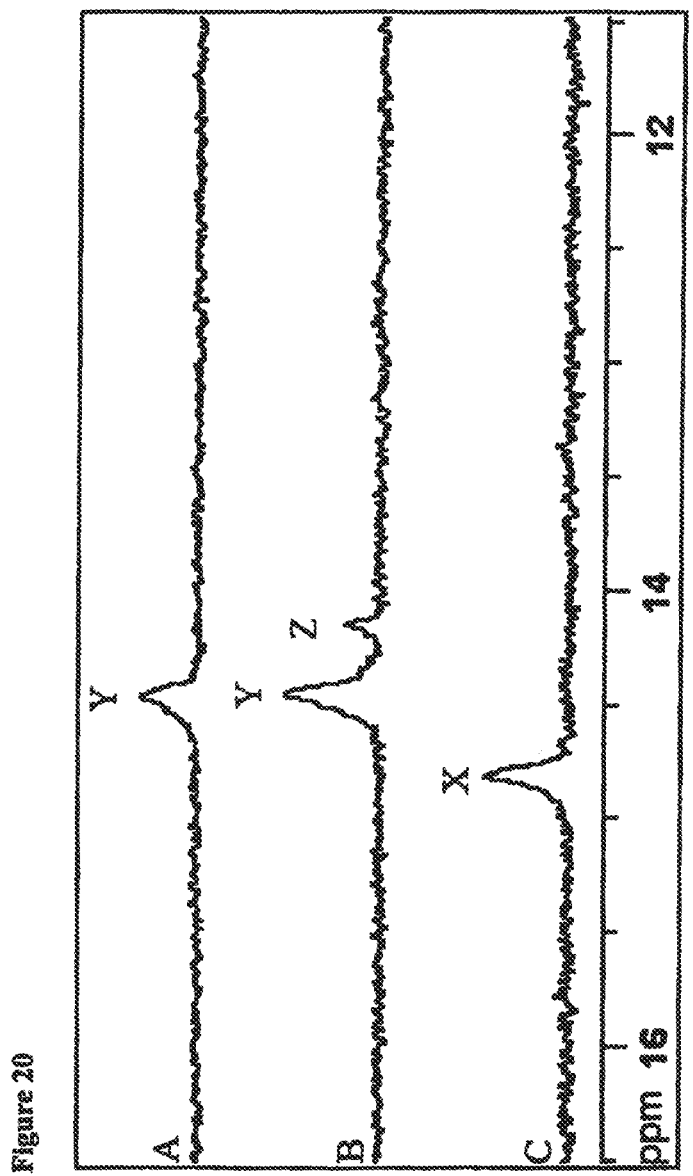
FIG. 20 depicts a 1D $^{31}$P NMR spectra showing the three distinct MeOPN-associated resonances (X, Y and Z) discussed in this work. Panel A: CPS of *C. jejuni* 81-176 wild-type that contains only one MeOPN units (peak Y); Panel B: CPS of *C. jejuni* 81-176 wild-type that contains two MeOPN units (peak Y and Z); Panel C: CPS of *C. jejuni* CJJ81176_1435 (3636) that contains a new MeOPN CPS modification (peak X).
Figure 21:
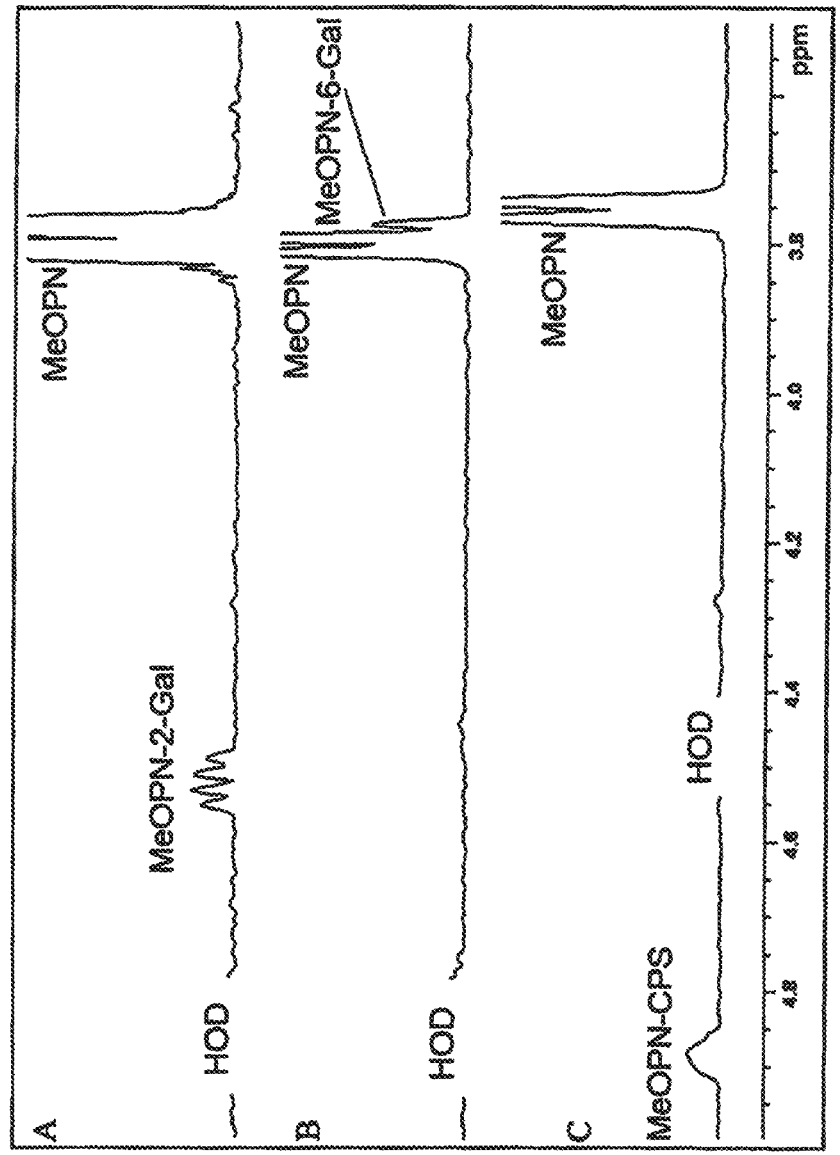
FIG. 21 depicts a 1D slices from a 2D $^1$H-$^{31}$P Heteronuclear Multiple Bond Correlation NMR experiment. Panel A: CPS of *C. jejuni* 81-176 wild-type showing the through bond correlation between MeOPN and 2-position of galactose; Panel B: CPS of *C. jejuni* CJJ81176_1435 (3477) showing the through bond correlation between MeOPN and 6-position of galactose; Panel C: CPS of *C. jejuni* CJJ81176_1420 (3636) showing the through bond correlation between MeOPN and an unidentified CPS position. HOD represents the position of water peak in each experiment.

As discussed above, experiments with *C. jejuni* mutant strain CJJ1435::cm (strain 3718) revealed not only two expected MeOPN shifts at $\delta_P$ 14.48 and 14.20 but also a new shift at $\delta_P$ 14.72 (X) (FIG. 20). Further studies were performed as detailed below to determine the linkage site of the newly observed MeOPN (X).

2D $^1$H-$^{31}$P HMBC:

The first additional NMR spectrum collected was a 2D $^1$H-$^{31}$P HMBC. This was to check for the Gal-2 and Gal-6 linkages before conducting a full analysis of the CPS by NMR and GC-MS. The 2D $^1$H-$^{31}$P HMBC showed a new cross-peak that was not previously observed for either the Gal-2 or Gal-6 MeOPN attachments. The cross-peak was underneath the HOD peak at 295K, which resulted in the spectrum being collected a second time at 320K (data not shown). The stronger cross peak at $\delta$ 4.92 ($^1$H) and $\delta$ 14.72 ($^{31}$P) became the resonance of interest and was labelled peak X. It was decided that full characterization was required, and GC-MS and NMR experiments were carried out.

1D-$^1$H:

A 1D-$^1$H spectrum was collected for strain 3718, and compared to a previously published spectrum (Kanipes et al., (2006) *J Bacteriol.* 188, 3273-3279.) It was noted that the CPS contained 1 or 2 anomeric shifts that were visible at 295K, to observe the β-anomer NMR needed to be conducted at a higher temperature. A second 1D-$^1$H spectrum was collected at 315K which revealed 2 more resonances in the downfield range for anomeric resonances (data not shown). From a previously published 81-176 waaC CPS, anomeric resonances were observed at $\delta$ 5.12 for 6d-DD-altro-Hep, $\delta$ 4.98 for α-Gal and $\delta$ 4.75 for β-GlcNAc (Kanipes et al., (2006) *J Bacteriol.* 188, 3273-3279.) Similar anomeric shifts were observed in strain 3718 at $\delta$ 5.06 (A), 5.05 (B) and 4.80 (C) (data not shown). An additional resonance observed in the anomeric region was at $\delta$ 4.92 (X) (data not shown). Other comparable resonances were observed at $\delta$ 3.78 for the CH$_3$ of the MeOPN, $\delta$ 2.04 for the CH$_3$ of the GlcNAc, and $\delta$ 1.74 of one of the 6-deoxy protons (data not shown). Additional 2D NMR experiments were conducted to determine the identity of the resonances in the anomeric region, and to attempt to assign their corresponding ring systems.

2D $^1$H-$^{13}$C HSQC—Anomeric Region:

To determine the number of residues involved in the CPS, a 2D $^1$H-$^{13}$C HSQC was conducted. Looking upfield in the $^1$H direction at the anomeric region there were 4 visible cross-peaks (data not shown). It was noted that proton shift at $\delta$ 4.92 had a $^{13}$C cross peak at $\delta$ 79.04, which is above the expected range of an anomeric carbon ($\delta$ 90-112). It was then noted that this unusual cross-peak came at the same proton shift at peak X from the 2D $^1$H-$^{31}$P HMBC. The remaining cross peaks were labelled as system A, B and C, respectively (data not shown). Other cross-peaks that were noted were that of the 6-deoxy from the 6d-DD-altro-Hep, the CH$_3$ from GlcNAc, and the CH$_3$ from the MeOPN. To assign the remaining protons including the identity of X, and their respective carbons, additional 1D and 2D experiments were required.

2D $^1$H-$^1$H COSY:

A 2D $^1$H-$^1$H COSY was performed on the CPS in an attempt to assign the ring systems of A, B and C. The ring region from the $^1$H-$^{13}$C HSQC showed overlapping and this was reiterated in the ring region of the $^1$H-$^1$H COSY (data not shown). Even with the crowded ring region, the connections between H-1 of the 3 systems and their respective H-2 could be assigned. It was observed that A-1 had a cross peak at $\delta$ 3.79 (A-2), B-1 had a cross-peak at $\delta$ 3.92 (B-2), and C-1 had a cross peak at $\delta$ 3.89 (C-2) (data not shown). To assist with further proton assignments both 2D and selective 1D TOCSY experiments were carried out.

2D-TOCSY:

The 2D-TOCSY allowed for protons within the same system to see each other through a transfer of magnetization. Overlaying the 2D-TOCSY and COSY more information and insight into the ring systems was achieved. Notably, peak X was able to be linked to an anomeric resonance, and the identity of the residue was uncovered.

Knowing the location of proton B-1 and B-2, the COSY could be utilized further to reveal B-3 at δ 4.21 (data not shown). The overlay of the 2 spectrum then revealed a cross-peak from both the COSY and the TOCSY that linked B-3 to peak X at δ 4.98 (data not shown). Peak X was reassigned as B-4. These assignments were confirmed by assignment of proton B-1 to B-4 on the 2D TOCSY spectrum (data not shown). A 1D slice from the 2D TOCSY was extracted for the anomeric resonance B-1 (data not shown). This slice revealed 3 additional peaks, and the peak at δ 4.25 could be assigned as B-5 by referring back to the 2D spectra and finding a connection to B-4. The remaining two resonances at δ 3.77 and δ 3.93 were not able to be assigned using this data alone.

Systems A and C were analyzed in a similar fashion. This resulted in the assignment of A-3 at δ 4.34, and C-3 at δ 3.50 (data not shown). In addition to starting from the anomeric resonances, the 6-deoxy resonances were assessed. Starting at H-6/6' a strong connectivity was observed at δ 3.79 in both the COSY and TOCSY; this corresponded to H-7 (data not shown). Another cross-peak to the H-6/6', TOCSY only, was noticed at δ 4.15 (data not shown). This was assigned as the H-5 of the 6d-DD-altro-Hep system. Using the overlay of the two 2D experiments, and also a 1D slice of the row corresponding to the H-5 resonance (δ 4.15), H-4 was assigned at δ 3.85 (data not shown). Using this new connection, the overlaid 2D spectra were revisited and a cross-peak between δ 3.85 (H-4) and δ 4.34 (A-3) was observed. This resulted in system A being assigned as the 6d-DD-altro-Hep. System C could not be analyzed through this technique past the proton C-3, however, information could be gathered regarding its identity through the chemical shift of the anomeric proton. Since the GlcNAc was the only β-anomer in the CPS, it could be deduced that the anomeric shifted the most upfield would correspond to the β-configured sugar. This assumption is also backed-up by the previously reported anomeric shift of the β-GlcNAc at δ 4.75, compared to this CPS at δ 4.76 (Kanipes et al., (2006) *J Bacteriol.* 188, 3273-3279.)

With system A assigned to the 6d-DD-α-altro-Hep, and system C assigned to the β-GlcNAc, system B was assigned as the α-Gal. Assignments of the ring carbons would serve as confirmation of the identities of systems A-C.

2D $^1$H-$^{13}$C HSQC (Revisited):

The associated carbons could now be assigned for the rings, and the remaining protons of the Gal (B) and GlcNAc (C) were able to be assigned. The anomeric cross-peaks were assigned where it is now known that: A=6d-DD-α-altro-Hep, B=α-Gal and C=β-GlcNAc. System A carbons were assigned first in their entirety since all the proton shifts were known; δ 101.6 (A-1), 85.2 (A-2), 72.6 (A-3), 74.0 (A-4), 70.1 (A-5), 36.4 (A-6), 36.5 (A-6'), and 61.0 (A-7) (Table 3, FIG. 27). The downfield carbon shift of A-2 at δ 85.2 agrees with the assignment of system A as the 6d-DD-α-altro-Hep, since it is linked at the 2-position and this results in a downfield shift of the linked carbon.

System B's carbons were then assigned, for proton 1-5; δ 99.6 (B-1), 70.2 (B-2), 79.2 (B-3), 79.0 (B-4), and 71.6 (B-5) (Table 3, FIG. 27). Again, the linkage of the α-Gal is at the 3-position and its carbon is shifted downfield to δ 79.2, and B-4 is the attachment site of the MeOPN moiety, therefore, the downfield shift of its carbon to δ 79.0 is expected as well. The remaining protons to be assigned for the α-Gal system are B-6/6'. Two proton shifts with the same carbon shift were found at δ 3.93/δ 63.4 and δ 3.77/δ 63.3 (FIG. 27), this is characteristic of the geminal protons at the 6-position of a hexopyranose.

TABLE 3

Proton and Carbon Assignments of the 3718 CPS.

| Residue | H-1<br>C-1 | H-2<br>C-2 | H-3<br>C-3 | H-4<br>C-4 | H-5<br>C-5 | H-6/6'<br>C-6/6' | H-7<br>C-7 | CH$_3$ |
|---|---|---|---|---|---|---|---|---|
| α-6d-altro-Hep | 5.07<br>101.6 | 3.79<br>85.2 | 4.34<br>72.6 | 3.85<br>74.0 | 4.15<br>70.1 | 2.10/1.74<br>36.4/36.5 | 3.79<br>61.0 | — |
| α-Gal | 5.05<br>99.6 | 3.92<br>70.2 | 4.21<br>79.2 | 4.92<br>79.0 | 4.25<br>71.6 | 3.93/3.77<br>63.4/63.3 | — | — |
| β-GlcNAc | 4.76<br>105.0 | 3.89<br>59.7 | 3.50<br>78.0 | 3.75<br>77.8 | 3.74<br>70.5 | 3.93/3.77<br>63.4/63.3 | — | 2.05<br>25.1 |
| MeOPN | — | — | — | — | — | — | — | 3.77<br>56.9 |

Finally, system C's carbon 1, 2 and 3 were assigned: δ 105.0 (C-1), 59.7 (C-2), and 78.0 (C-3) (Table 3, FIG. 27). The downfield shift of C-3 at δ 78.0 agrees with the linkage being at the 3-position of the β-GlcNAc, confirming the assignment. Remaining to be assigned for system C was proton/carbon 4, 5 and the 6/6'. The C-4 was assigned at δ 77.8 and the C-5 was assigned as δ 70.5 based on comparison to the previously characterized HS:23/36 CPSs (Kanipes et al., (2006) *J Bacteriol.* 188, 3273-3279.) The C-6/6' based on comparison to previous data are likely at a very similar shift to the B-6/6' protons and carbons, this results in the cross-peaks not being visible in the HSQC, since they are overlapped. An addition cross-peak attributed to the β-GlcNAc is at δ 2.05/δ 25.1, and this is from the CH$_3$ group of the N-acetyl substituent.

GC-MS Analysis:

Monosaccharide composition and linkage analysis was also carried out on the CPS to confirm the results observed through NMR. From the composition analysis it was first noted that, unlike previously characterized HS:23/36 structures, there was very little presence of the 3-OMe-6d-altro-Hep. The majority of the altro-Hep was in the 6-deoxy form, with an additional small amount of the unmodified Hep (data not shown). In addition to the heptose variations, the Gal and GlcNAc were also observed in the composition analysis. All peak identities were confirmed by comparison to relative retention times, as well as analysis of fragmentation patterns (data not shown).

The linkage analysis was also rich in information. The previously seen major linkages of -3)Gal(1-,-2)6d-altro-Hep (1-, and -3)GlcNAc(1- were all observed, as expected (data not shown). In addition to these linkages, there were also terminal Gal, -2)altro-Hep(1-, which were seen in small quantities previously, and a newly observed peak corresponding to -3,4)Gal(1- (data not shown). Again all peak identities were confirmed by comparison to relative retention times, as well as analysis of fragmentation patterns (data not shown). The -3,4)Gal(1-being present confirmed the assignment of an attachment site for MeOPN being at the 4-position of the 3-linked Gal in the CPS structure.

Figure 40:
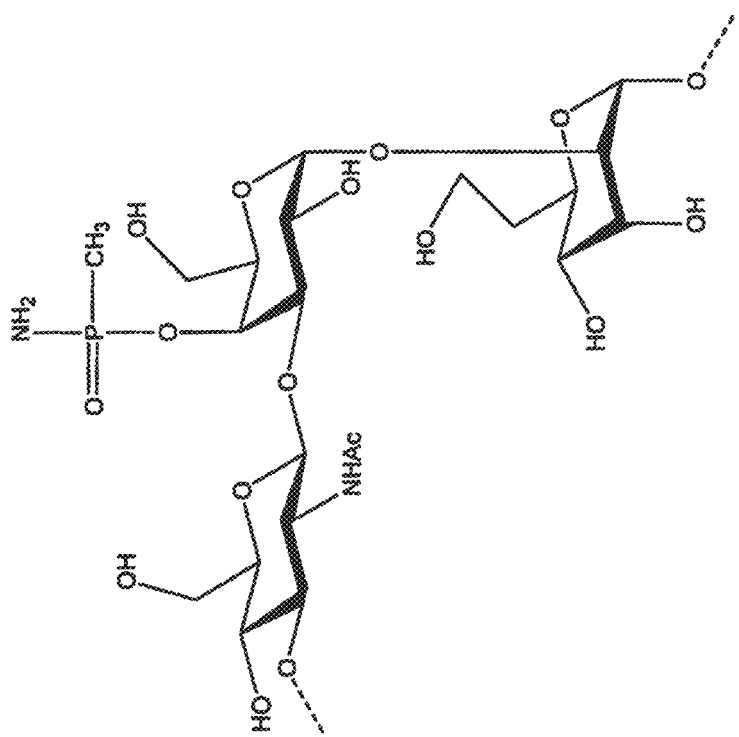
FIG. 40 depicts the new variable structure of HS:23/36, with the MeOPN attachment site at Gal-4.

Final Structure:

Returning to the connection observed in the 2D $^1$H-$^{31}$P HMBC, peak X could now be positively assigned. This assignment results in a new connection of MeOPN in the HS:23/36 structure at the 4-position of α-Gal. This gives a new variable CPS structure to the HS:23/36 serotype (FIG. 40).

Example 10

Synthesis of MeOPN-4-Gal Antigen

Figure 29:
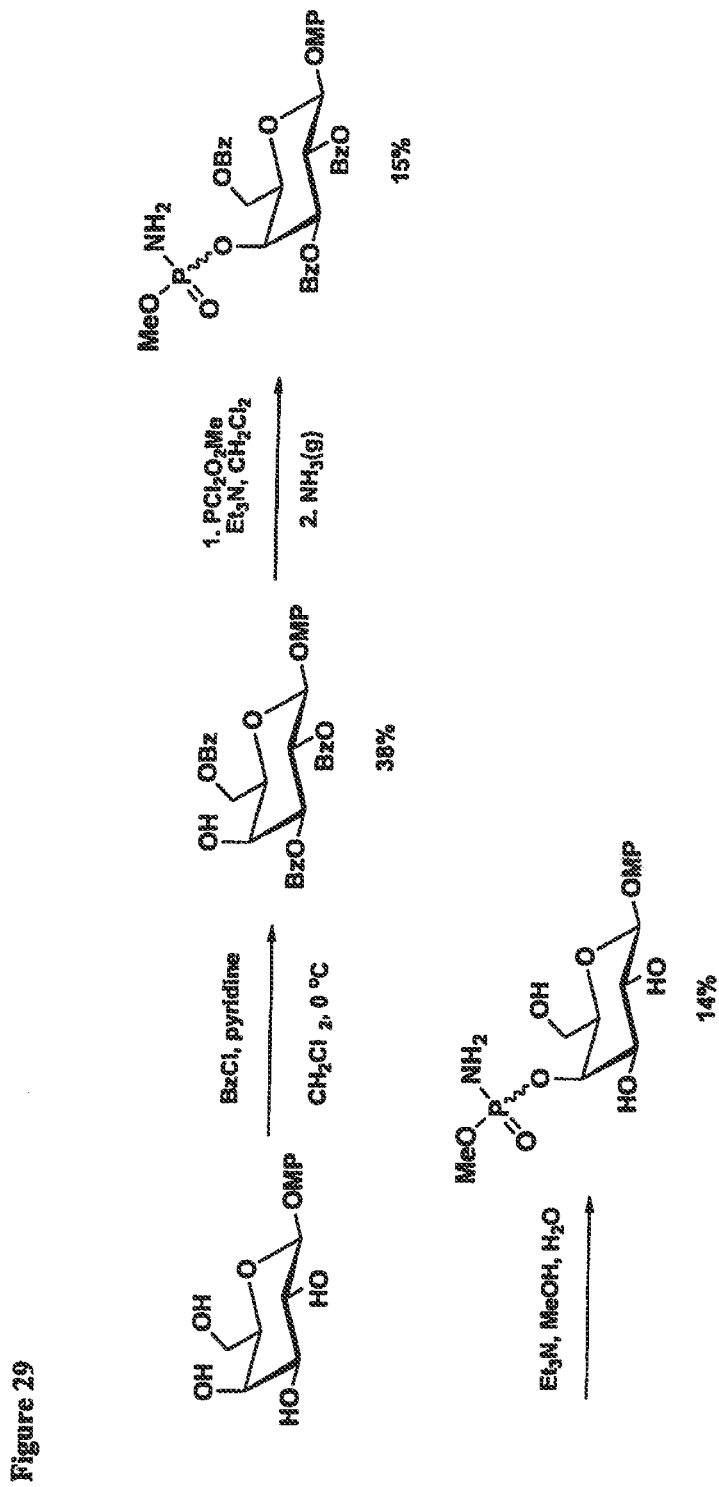
FIG. 29 depicts the synthesis scheme of 4-Methoxyphenyl 4-O-methyl-phosphoramidyl-β-D-galactopyranoside, compound D described in Example 10. PCl$_2$O$_2$Me: Methyl dichlorophosphate; Et$_3$N: Triethylamine; CH$_2$Cl$_2$: Dichloromethane; Bz: Benzoyl.
Figure 30:
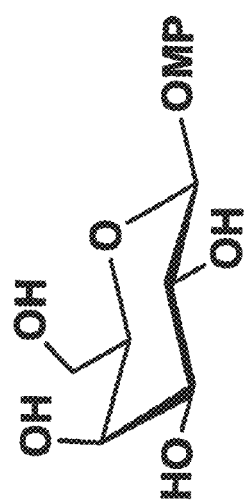
FIG. 30 depicts compound A, 4-methoxyphenyl-β-D-galactopyranoside described in Example 10.
Figure 31:
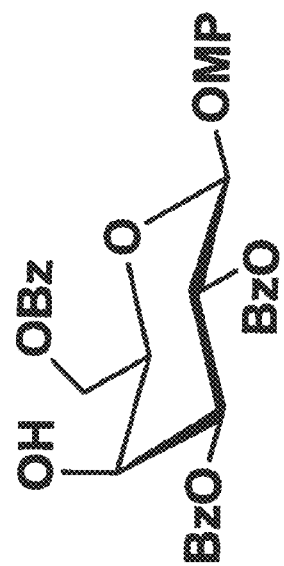
FIG. 31 depicts compound B, 4-Methoxyphenyl 2,3,6-tri-O-benzoyl-β-D-galactopyranoside; $C_{34}H_{30}O_{10}$: 598.18 g/mol described in Example 10.

The synthesis scheme to prepare a MeOPN-4-Gal antigen, methoxyphenyl 4-O-methyl-phosphoramidyl-β-D-galactopyranoside (referred to below as "compound D" or "galactoside D") is depicted in FIG. 29 and is described in detail below. Briefly, the synthesis of the galactoside D began with a known compound, 4-methoxyphenyl-β-D-galactopyranoside ("compound A" or "galactoside A"), obtained from a published procedure (Montel, E. et al.; *Aust. J. Chem.* 2009, 62, 575-584.) See FIG. 30. A selective benzoylation with ~3 equivalent of benzoyl chloride on galactoside A yielded the 2,3,6-tri-O-benzoylated product B ("compound B"). (See FIG. 31). The selectivity can be explained by the difference in reactivity between the four hydroxyl groups in a galactoside. Hydroxyl groups in the axial orientation are expected to undergo acylation less rapidly than OH groups in the equatorial orientation, which are less sterically hindered and much more accessible. In addition, the 4-OH is further sterically hindered by the larger hydroxymethyl group on the C-5 position and therefore has the lowest reactivity. However, the yield attained here is unexpectedly lower than originally anticipated, generating significant amount of 3,4,6-tri-O-benzoylated and the fully benzoylated product.

Figure 32:
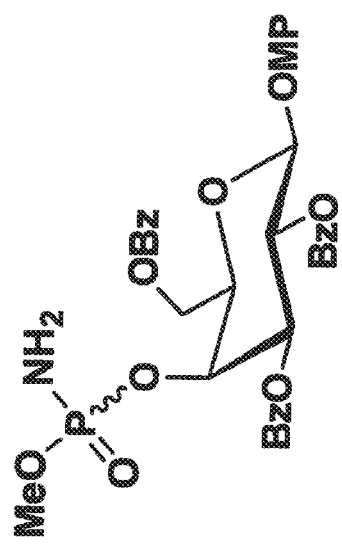
FIG. 32 depicts compound C, 4-Methoxyphenyl 2,3,6-tri-O-benzoyl-4-O-methyl-phosphoramidyl-β-D-galactopyranoside; $C_{35}H_{34}NO_{12}P$: 691.18 g/mol described in Example 10.

The introduction of MeOPN modification onto compound B followed a similar strategy as that employed in the synthesis of MeOPN-6-Gal (and MeOPN-2-Gal) described above. After stirring the sugar with methyl dichlorophosphate in the presence of $Et_3N$ (40 eq.) for 48 hours at 35° C., the starting material was completely consumed, as indicated by TLC. The low reactivity is expected, as 4-OH has the least reactivity in a galactoside, and further decreased by electron-withdrawing O-Bz groups. After purification by flash chromatography, MeOPN product C ("compound C") was collected as two diastereoisomers in a roughly 2:1 ratio as indicated by $^{31}P$ and $^1H$ NMR (FIG. 32).

Figure 33:
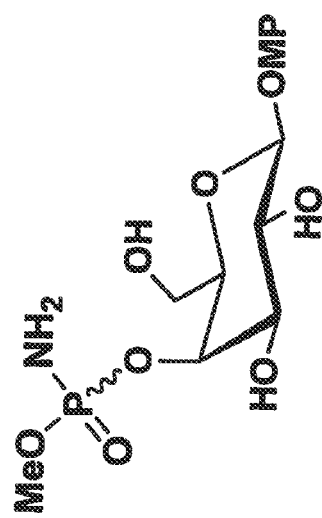
FIG. 33 depicts compound D, 4-Methoxyphenyl 4-O-methyl-phosphoramidyl-β-D-galactopyranoside; $C_{14}H_{22}NO_9P$: 379.10 g/mol described in Example 10.

The deprotection of compound C was attempted in a 7:2:1 mixture of $MeOH/H_2O/Et_3N$. Compound C was completely consumed in ~5 hours producing the undesired O-methyl phosphate product, as indicated by TLC. Although in low yield (14%), deprotected MeOPN product (compound D) was obtained. This deprotected compound D was collected as a single diastereoisomer, producing a single phosphorous signal at 14.65 ppm (FIG. 33). Synthesis details are provided in detail below.

To a solution of 4-methoxyphenyl β-D-galactopyranoside ("compound A") (1.92 g, 67.1 mmol) dissolved in $CH_2Cl_2$ (50 mL), DMF (4 mL) and pyridine (2.15 mL, 268 mmol), BzCl (2.31 mL, 201 mmol) was then added over 1 h –20° C. The reaction mixture was stirred at 0° C. for 3 hours before MeOH (5 mL) was added and the reaction mixture was concentrated under reduced pressure. Purification with flash chromatography (1:4 EtOAc-hexanes) gave product "compound B" (1.53 g, 38%) (See FIG. 31). $[\alpha]_D^{25}=+124.0°$ (c=0.1, $CHCl_3$); $^1H$ NMR (400 MHz, $CDCl_3$); δ 8.04-7.32 (m, 15H, Ar); 7.00-6.66 (m, 4H, $MeOC_6H_4$); 6.00 (dd, 1H, $J_1$=8.0 Hz, $J_2$=10.3 Hz, H-2); 5.39 (dd, 1H, $J_1$=3.2 Hz, $J_2$=10.3 Hz, H-3); 5.12 (d, 1H, J=8.0 Hz, H-1); 4.71 (m, 1H, H-6a); 4.61 (m, 1H, H-6b); 4.39 (m, 1H, H-4); 4.13 (m, 1H, H-5); 3.69 (s, 3H, $OCH_3$); $^{13}C$ NMR (100 MHz, $CDCl_3$): δ 166.4, 165.8, 165.4, 155.7, 151.2, 133.6, 133.4, 133.3, 129.9, 129.8, 129.6, 129.4, 128.9, 128.6, 128.4, 119.0, 114.4 (Ar); 101.2 (C-1); 74.1 (C-3); 72.6 (C-5); 69.3 (C-2); 67.3 (C-4); 62.8 (C-6); 55.6 ($OCH_3$). HRMS (ESI): Calcd. For $C_{34}H_{30}NaO_{10}$ $[M+Na]^+$: 621.1737, found: 621.1733.

To a solution of compound B (94.1 mg, 0.157 mmol) and methyl dichlorophosphate (0.57 mL, 4.6 mmol) dissolved in anhydrous $CH_2Cl_2$ (4 mL) with crushed molecular sieves 4 Å, $Et_3N$ (0.64 mL, 4.6 mmol) was added drop-wise at 0° C. The reaction mixture was stirred at 35° C. for 48 hours. Upon completion of the reaction as judged by TLC, ammonia gas was injected into the reaction mixture through a needle. After 3 min, the reaction mixture was filtered and concentrated under reduced pressure. Purification with column chromatography (1:1 EtOAc-hexanes) yielded MeOPN product "compound C" (FIG. 32) (16.1 mg, 15%). $^1H$ NMR (400 MHz, $CDCl_3$): δ 8.10-7.36 (m, 30H, Ar); 6.92-6.60 (m, 8H, $MeOC_6H_4$); 6.00 (m, 2H, H-2, H-2*); 5.15 (dd, 1H, $J_1$=2.3 Hz, $J_2$=10.6 Hz, H-3); 5.12 (dd, 1H, $J_1$=2.3 Hz, $J_2$=10.6 Hz, H-3*); 5.19 (2dd, 2H, $J_1$=3.1 Hz, $J_2$=10.0 Hz, H-4, H-4*); 5.15 (2d, 2H, J=8.0 Hz, H-1, H-1*); 4.70 (m, 4H, H-6a, H-6a*, H-6b, H-6b*); 4.35 (m, 2H, H-5, H-5*); 3.72 (d, 3H, $^3J_{PH}$=11.4, $POCH_3$); 3.68 (s, 6H, $OCH_3$); 3.52 3.50 (d, 3H, $^3J_{PH}$=11.4 Hz, $POCH_3$*); 2.87 (d, 2H, J=4.7 Hz, $NH_2$); 2.71 (d, 2H, J=4.6 Hz, $NH_2$*). $^{13}C$ NMR (100 MHz, $CDCl_3$): δ 166.1, 165.7, 165.5, 155.7, 151.1, 133.5, 133.4, 133.3, 130.1, 129.8, 129.7, 129.6, 129.3, 129.2, 128.7, 128.5, 128.4, 126.3, 119.0, 118.4, 114.4 (Ar); 101.1 (C-1); 72.7 (C-5); 72.1, 72.0 (C-3); 71.5 71.4 (C-4); 69.0, 68.9 (C-2); 62.8, 62.7 (C-6); 55.6 ($OCH_3$); 53.8, 53.7 ($POCH_3$); $^{31}P$ NMR (162 MHz, $CDCl_3$): δ 11.27, 10.79. HRMS (ESI): Calcd. For $C_{35}H_{35}NO_{12}P$ $[M+H]^+$: 692.1897, found: 692.1868.

Figure 34:
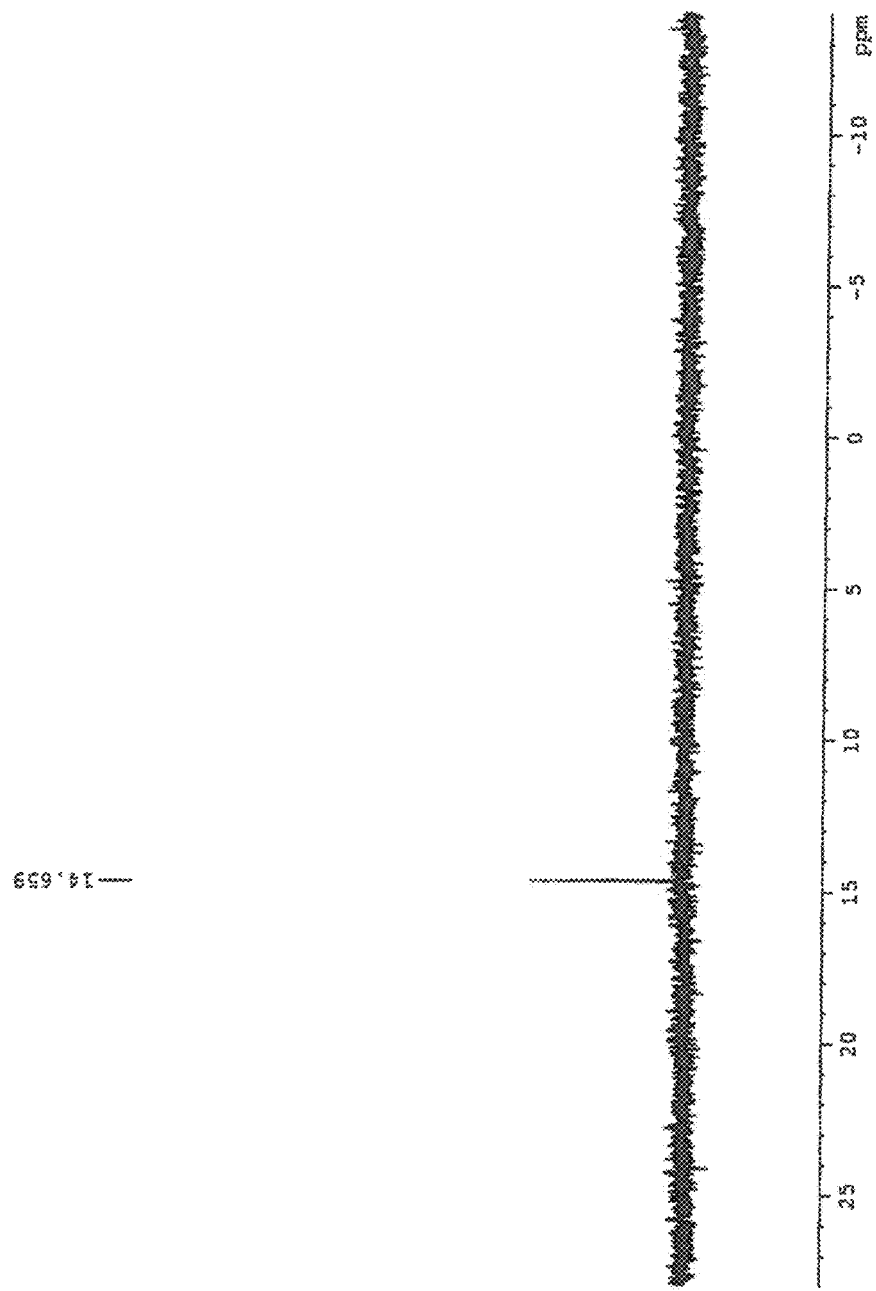
FIG. 34 depicts $^{31}$H NMR experiment of compound D showing the $^{31}$P resonance of MeOPN→4-β-D-Gal-OMP.

Compound C (4.0 mg, 5.8 µmol) was dissolved in a solution of 7:2:1 mixture of $MeOH—H_2O-Et_3N$ (1.5 mL). The mixture was stirred for 6 h at room temperature before it was neutralized with acetic acid and concentrated. Purification by flash chromatography eluting with 5:1 EtOAc-MeOH produced product "compound D" as a single diastereomer (FIG. 33) (0.3 mg, 14%). δ $^1H$ NMR (600 MHz, $D_2O$): δ 7.02-6.83 (m, 4H, $MeOC_6H_4$); 4.81 (d, 1H, H-1); 4.11 (m, 1H, H-4); 3.92 (m, 2H, H-3, H-5); 3.75-3.65 (m, 5H, H-2, H-6a, $OCH_3$); 3.61-3.55 (m, 4H, H-6b, $POCH_3$) $^{13}C$ NMR (150 MHz, $CDCl_3$): δ 118.0, 115.0 (Ar); 101.3 (C-1); 73.6 (C-3); 72.4 (C-2); 70.4 (C-5); 68.1 (C4); 58.9 (C-6); 55.7 ($OCH_3$); 53.9 ($POCH_3$). $^{31}P$ NMR (243 MHz, $CDCl_3$): δ 14.65. HRMS (ESI): Calcd. For $C_{14}H_{21}NO_9P$ $[M–H]^-$: 378.0954, found: 378.0954. Results of a $^{31}H$ NMR experiment of compound D showing the $^{31}P$ resonance of MeOPN→4-β-D-Gal-OMP is depicted in FIG. 34.

Example 11

Synthesis of Conjugate MeOPN-4-Gal Vaccine

Figure 35:
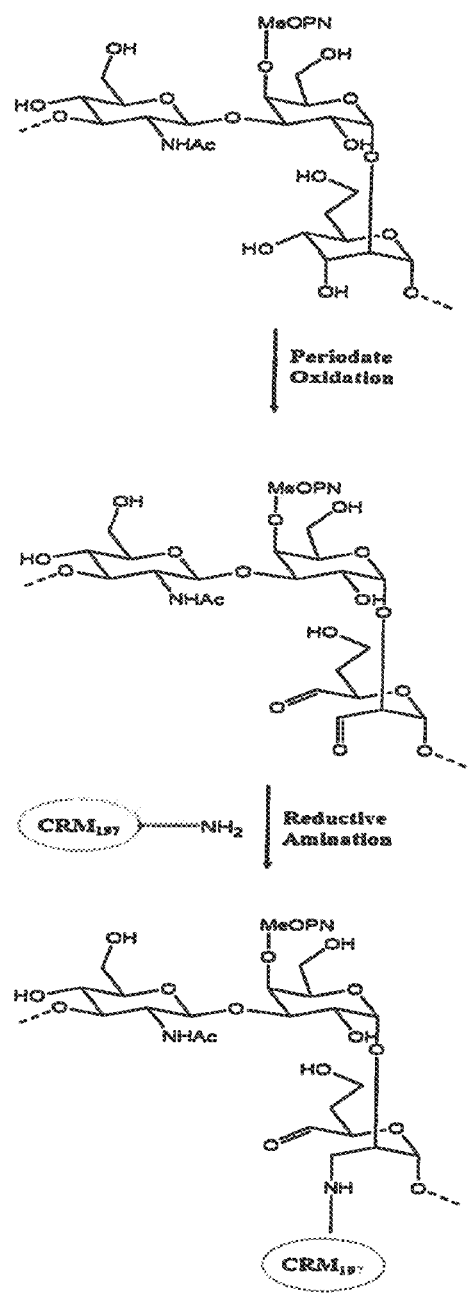
FIG. 35 depicts conjugation of the 3718 CPS by first activating with periodate oxidation, and then conjugating to CRM$_{197}$ via reductive amination.

Synthesis of a conjugate vaccine containing capsule polysaccharide (CPS) isolated from *C. jejuni* strain 3718 overexpressing MeOPN-4-Gal (described in Example 8) using periodate oxidation and reductive amination is depicted in FIG. 35 and described in detail below.

*C. jejuni* strain 3718 bacteria were gown and capsule polysaccharide isolated according to conventional methods. Briefly, *C. jejuni* strain 3718 bacteria were grown in a non-animal based liquid medium: tryptone substitute atholate, 13 g/liter (US Biological, Salem, Mass.; cat. no T8750-1); non-animal based yeast extract, 2.5 g/liter (Novagen, Hornsby Westfield, NSW 1635, Australia; Cat. No. 71270-3); sodium pyruvate, 1.25 g/liter (SigmaAldrich Corp, St. Louis, Mo.; Cat. No. P8574); CaCl2, 0.2 g/liter (SigmaAldrich Corp, St. Louis, Mo.; Cat. No. C5080); and NaCl, 3.2 g/liter (Fisher Scientific, Pittsburgh, Pa.; Cat. No. S640-3) at 37° C. under a microaerophilic environment. Extraction of the CPS was achieved as described in Example 8.

Figure 36:
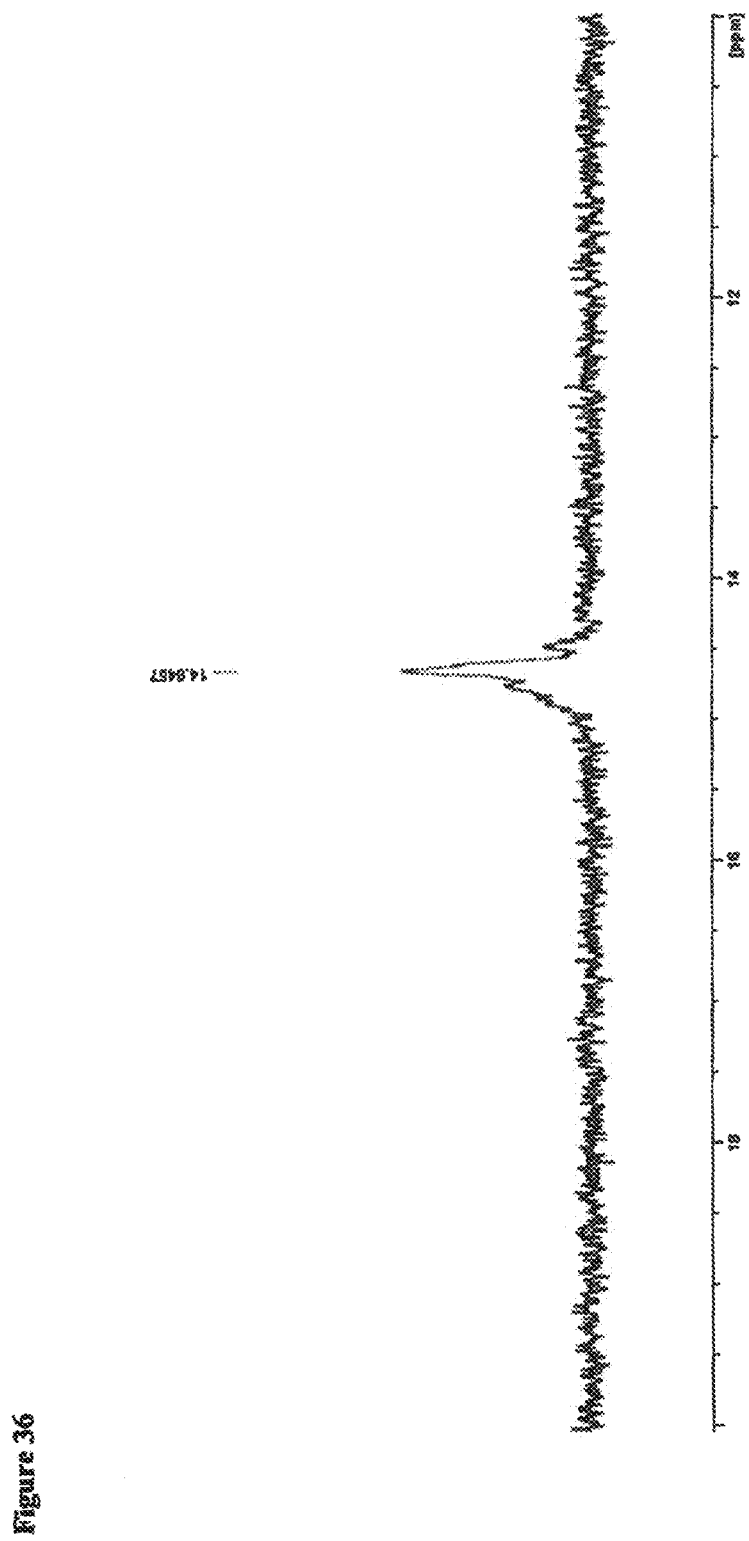
FIG. 36 depicts 1D $^{31}$P following the periodate oxidation of the 3718 CPS.

Periodate was used to activate the isolated CPS by producing two aldehydes at the vicinal diol of the 6d-altro-Hep, positions 3 and 4. The CPS was solubilized in a solution containing 0.04 M sodium iodate (NaIO4) and 0.1 M NaOAc, at a pH of 4.00. (See Monteiro M A, et al. Infection and Immunity, 2009; 77:1128-1136.) The reaction was stirred at room temperature for 2 hours and then kept at 5° C. for 72 hours, with intermittent stirring. After 3 days the reaction was quenched with ethylene glycol and placed onto dialysis (1 KDa MWCO) for 24 hours. The sample was then frozen and lyophilized for NMR analysis. The oxidized CPS was analyzed by NMR and was found to be intact based on 1D-1H and 2D 1H-13C HSQC experiments (data not shown.) The MeOPN was still attached to the CPS, shown by 1D 31P (FIG. 36).

The oxidized CPS was then subjected to reductive amination with two different carrier proteins, $CRM_{197}$ (FIG. 35) and BSA as follows. The periodate-oxidized-CPS was solubilized in a 0.1 M borate buffer, at a pH of 9.00. The carrier protein was solubilized in an equivalent volume of the buffer and added to the activated CPS by stirring slowly. Sodium cyanoborohydride ($NaBH_3CN$) was added to the reaction vial and the solution stirred slowly for 24 hours at room temperature. (See Lane C., Aldrichimica. 1975; 8:3-10.) The temperature was then increased to 37° C. for 48 hours. The reaction was placed on dialysis (25 KDa MWCO) for 72 hours. The sample was frozen and lyophilized for NMR analysis. The two conjugates ($CRM_{197}$ and BSA) were analyzed by 1D $^1H$ and $^{31}P$ NMR and did not show any sign of deterioration of the CPS (data not shown.)

Example 12

Rabbit Immunogenicity Studies

As discussed above, C. jejuni strain 3718 is the strain that overexpresses the MeOPN-4-Gal transferase (CJJ81176_1420 transferase) and is mutated for the MeOPN-2 and MeOPN-6-transferase (CJJ81176_1435). Phenotypically, it expresses only MeOPN-4-Gal. In order to test the immunogenicity of the 3718-$CRM_{197}$ vaccine conjugate prepared in Example 11, a rabbit was immunized according to conventional methods with the 3718-$CRM_{197}$ vaccine conjugate (Envigo, Frederick, Md.) Specifically, 300 µgs of the vaccine conjugate were administered to the rabbit per month over a three month time period. The vaccine conjugate was given in conjunction with Freund's complete adjuvant (BD Difco brand containing 5 mg Mycobacterium butyricum/10 ml administered 1:1 with the antigen (Becton, Dickinson and Co., Franklin Lakes, N.J.)). Serum samples were taken for endpoint ELISA analysis.

Figure 37:
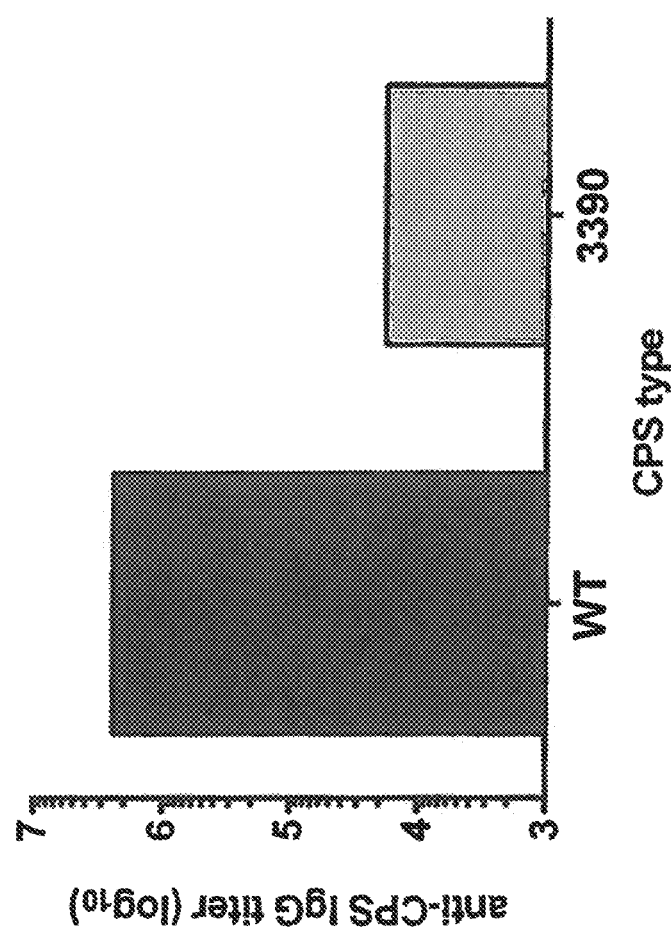
FIG. 37 depicts ELISA data from a rabbit immunogenicity study after one dose of 3718-CRM$_{197}$ antigen construct.

The ELISA data in FIG. 37 show endpoint titers two weeks post four doses of vaccine against capsule from wildtype C. jejuni and from the mpnC mutant (strain 3390). The data indicate that there is a low level response to the polysaccharide chain (endpoint ~1000) and a higher titer to the wildtype capsule containing MeOPN. These data confirm the presence of MeOPN-4-Gal in wildtype and demonstrate that the rabbit is generating antibodies to MeOPN-4-Gal, which is the only modification on strain 3718.

Figure 38:
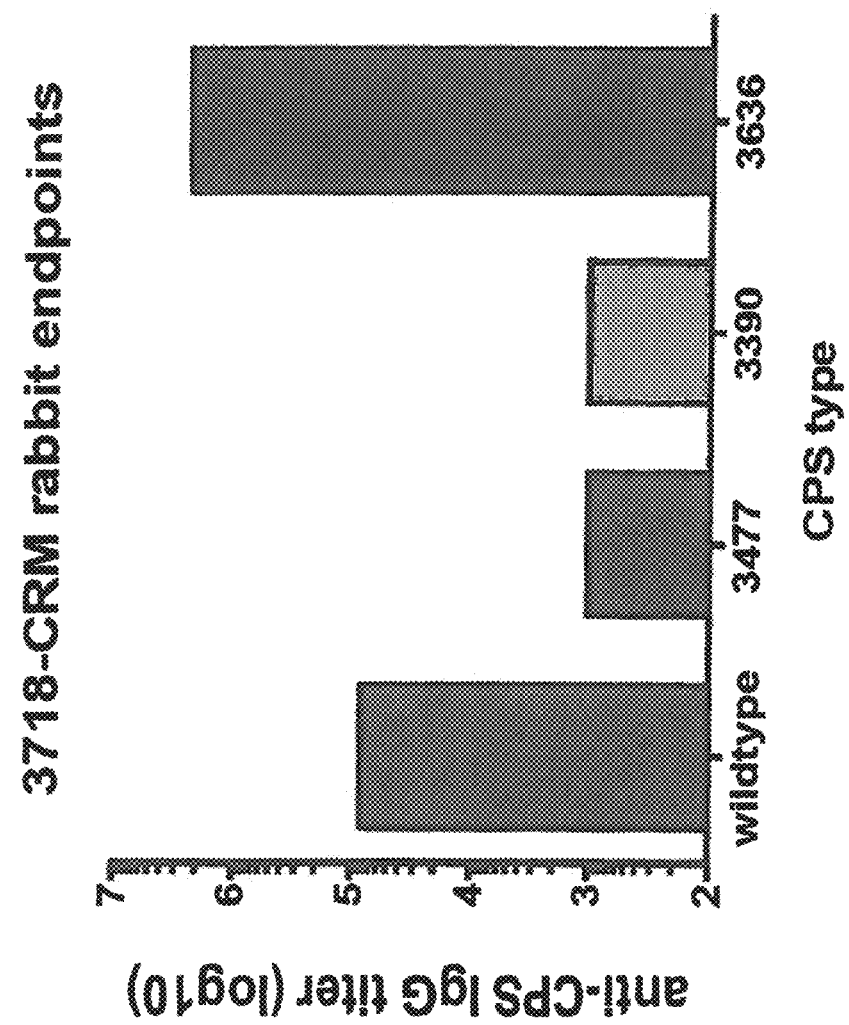
FIG. 38 depicts ELISA data from a rabbit immunogenicity study after a second dose of 3718-CRM$_{197}$ antigen construct.

Serum obtained two weeks after a second dose of 3718-$CRM_{197}$ vaccine conjugate was also used in an ELISA. Data shown in FIG. 38 depict the endpoint ELISA titers of serum from a rabbit after two doses of the 3718-$CRM_{197}$ vaccine conjugate. Taken together, these ELISA data show that there are some MeOPN-4-Gal epitopes in wildtype (endpoint ~10e5). The data also demonstrate that the responses to the polysaccharide chain are weak (~10e3) as measured by response to strain 3390 (which lacks all MeOPN based on a mutation in the biosynthetic pathway) and to mutant 3477 which lacks CJJ81176_1420, the MeOPN-4-transferase. Strain 3477 expresses only MeOPN-2-and MeOPN-6-Gal and the immune response is similar to that of strain 3390. Significantly, the data also indicate that there is a strong response to the MeOPN-4-Gal epitope as seen by the response to strain 3636 (~10e6), the mutant in the CJJ811876_1435 transferase. Strain 3636 expresses only MeOPN-4-Gal. Thus, the data demonstrate that MeON-4-Gal is immunogenic in rabbits.

Example 13

Creation of Synthetic Construct Comprising MeOPN-4-Gal

Figure 41:
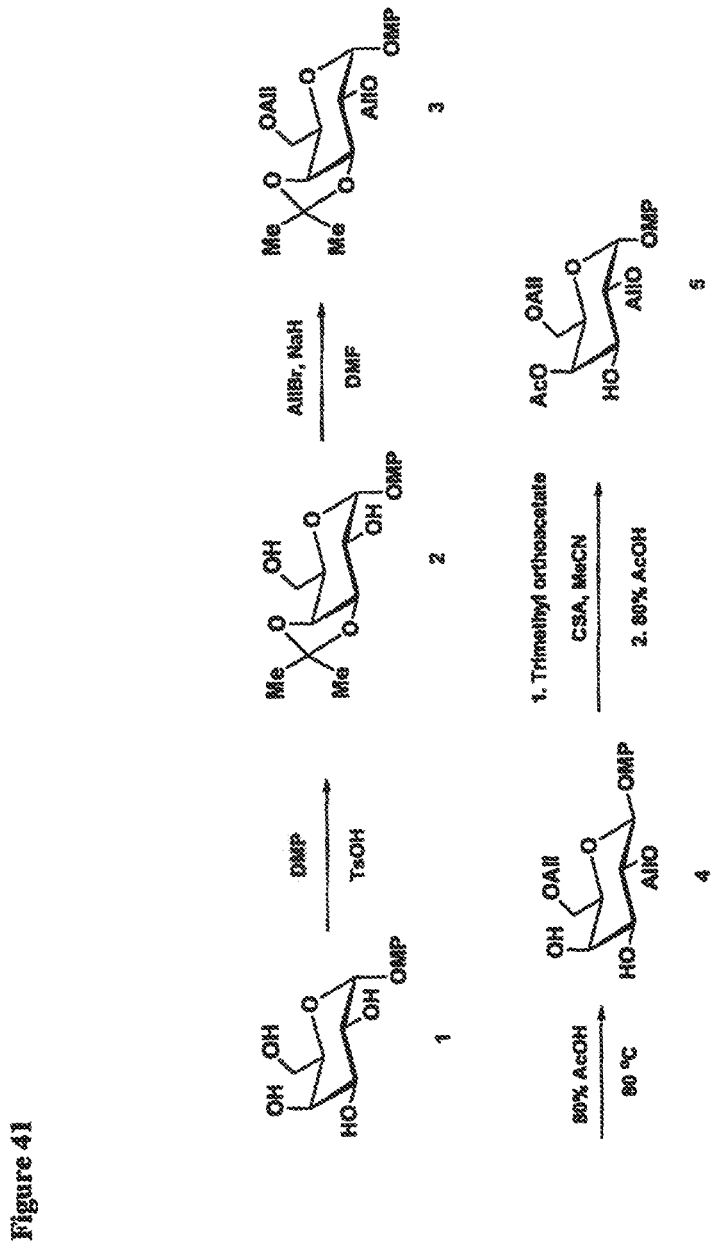
FIG. 41 depicts Scheme 1, the synthesis of galactosyl acceptor 5 in the creation of a disaccharide containing MeOPN-4-Gal described in Example 13. OMP: 4-methoxyphenyl group; DMP: 2,2-Dimethoxypropane; TsOH: p-Toluenesulfonic acid; AllBr: allyl bromide; DMF: Dimethylformamide; NaH: Sodium hydride; AcOH: Acetic acid; CSA: Camphorsulfonic acid; MeCN: Acetonitrile.

Details for the synthesis of a synthetic construct comprising a MeOPN-4-Gal epitope is provided below and detailed in FIGS. 41-43. Briefly, as depicted in FIG. 41, the synthesis toward galactosyl acceptor 5 begins with α-galactoside 1. Isopropylidene is used to selectively protect O-3 and O-4 position generating compound 2. Both O-2 and O-6 positions are then protected with allyl groups, generating compound 3. To distinguish O-3 and O-4 positions, isopropylidene is first removed generating compound 4. Position 4 is then selectively protected with O—Ac through orthoacetate chemistry, leaving 3-OH for glycosylation.

Figure 42:
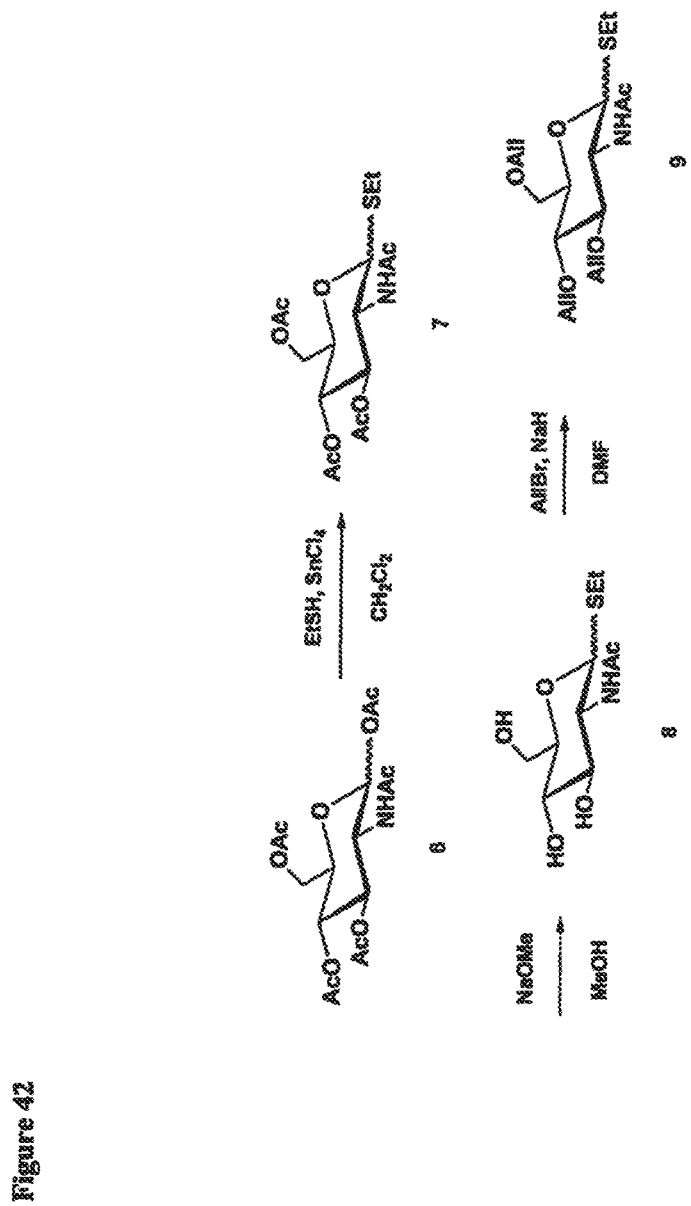
FIG. 42 depicts Scheme 2, the synthesis of NAc-glucosaminyl donor 9 in the creation of a disaccharide containing MeOPN-4-Gal described in Example 13. EtSH: Ethanethiol; SnCl$_4$: Tin (IV) chloride; CH$_2$Cl$_2$: Dichloromethane; SEt: Ethylthiol group; NaOMe: Sodium methoxide; MeOH: Methanol; AllBr: allyl bromide; NaH: Sodium hydride; DMF: Dimethylformamide.

As depicted in FIG. 42, synthesis of donor 9 starts with per-acetylated GlcNAc 6. Anomeric position can be replaced with ethanethiol generating thioglycoside 7. For the ease of deprotection of the disaccharide product, O—Ac groups are removed generating 8 and replaced with allyl groups generating 9.

Figure 43:
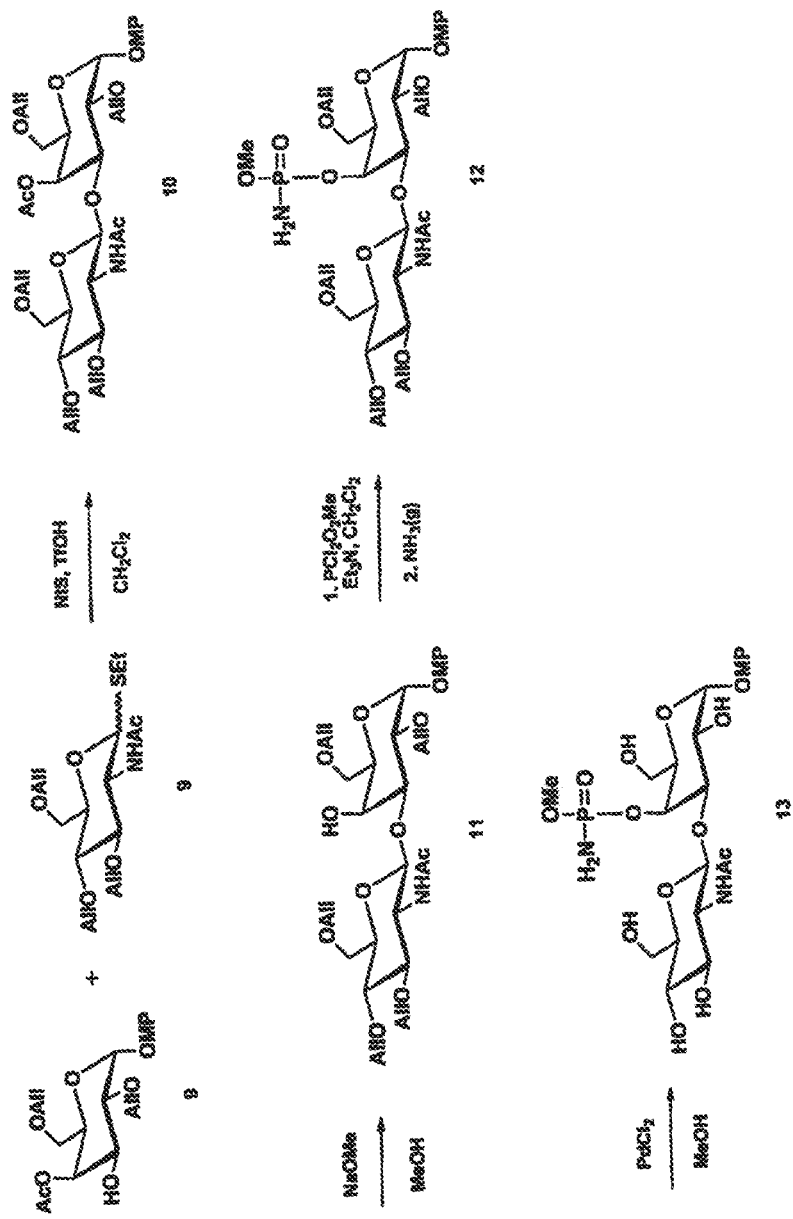
FIG. 43 depicts Scheme 3, the synthesis of MeOPN-containing GlcNAc-(1→3)-Gal disaccharide described in Example 13. SEt: Ethylthiol group; NIS: N-Iodosuccinirnide; TfOH: Trifluoromethanesulfonic acid (triflic acid); CH$_2$Cl$_2$: Dichloromethane; NaOMe: Sodium methoxide; MeOH: Methanol; PCl$_2$O$_2$Me: Methyl dichlorophosphate; Et$_3$N: Triethylamine; NH3: Ammonia; PdCl$_2$: Palladium (II) chloride.

As depicted in FIG. 43, Glycosylation between acceptor 5 and donor 9 is achieved with NIS/TfOH as promoter. O-Acetyl group is then selectively removed from disaccharide 10 giving compound 11 with a free 4-OH for MeOPN introduction. Finally, allyl protecting groups in compound 12 are removed generating MeOPN-containing disaccharide 13. Abbreviations found in FIGS. 41-43 are as follows: DMP: 2,2-Dimethoxypropane; TsOH: p-Toluenesulfonic acid; AllBr: Allyl bromide; NaH: Sodium hydride; DMF: Dimethylformamide; AcOH: Acetic acid; CSA: Camphorsulfonic acid; MeCN: Acetonitrile; EtSH: Ethanethiol; $SnCl_4$; Tin (IV) chloride; $CH_2Cl_2$: Dichloromethane; NaOMe: Sodium methoxide; MeOH: Methanol; DMF: Dimethylformamide; NIS: N-Iodosuccinimide; TfOH: Trifluoromethanesulfonic acid (triflic acid); $PCl_2O_2Me$: Methyl dichlorophosphate; $Et_3N$: Triethylamine; NH3: Ammonia; $PdCl_2$: Palladium (II) chloride.

Example 14

Figure 24:
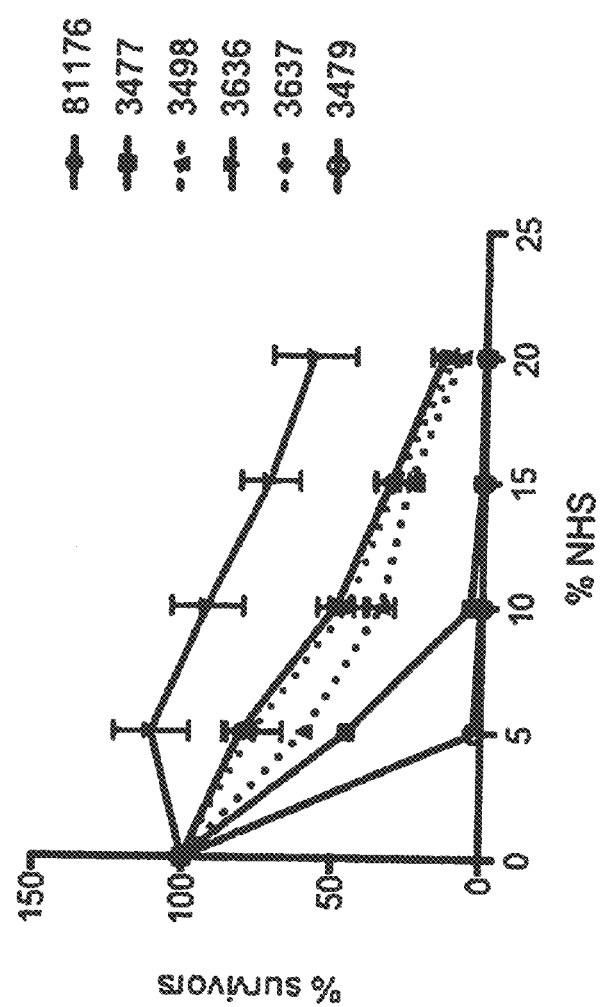
FIG. 24 depicts the resistance of C. jejuni strains to increasing amounts of normal human sera (NHS). Bacteria were exposed to increasing amounts of NHS for 1 h at 37° C. and survivors enumerated by plate counts. Genotypes of the strains are shown in Table 1. Strain 3636 was significantly different from wildtype at all four concentration of NHS ($P<0.05$). Strain 3477 was significantly less serum resistant than wildtype at 5% NHS ($P<0.05$), 10% ($P<0.005$) and 15% ($P<0.05$). There was no significant difference in the complements of the two mutants, 3498 and 3637, with wildtype at any concentration of NHS. The double transferase mutant, 3479, was significantly lower than wildtype at 5% ($P<0.0005$), 10% ($P<0.005$), and 15% NHS ($P<0.05$).

Methods to Induce Serum Bactericidal Killing Comprising the Use of Antibodies Directed to MeOPN-Sugar Moieties in Conjugate Vaccines We have demonstrated that naturally occurring antibodies in normal human sera (NHS) that cross react with the capsular polysaccharide in C. jejuni can induce the complement cascade (see FIG. 24). It appears that the presence of MeOPN moieties on the capsule prevents these anti-polysaccharide antibodies from binding to the cell surface. We have also determined that epitopes containing MeOPN are the immunodominant epitopes in HS23/36 capsule conjugate vaccines. In view of these data, we developed a serum bactericidal assay to determine if these anti-MeOPN antibodies generated to a capsule conjugate vaccine could induce serum bactericidal antibodies.

Materials and Methods

Preparation of *Campylobacter jejuni*: Bacterial strain 81-176 was grown on Muller Hinton agar plates (MHP; Muller Hinton Broth 21 g/liter and Bacto Agar 15 g/liter [Becton Dickinson, Sparks, Md.]) at 37° C. In a microaerophilic (Nitrogen 85%, Carbon Dioxide 10%, and Oxygen 5%) environment for 20 h overnight. Cells are harvested in Dextrose-Gelatin-Veronal (DGV; Lonza, Walkersville, Md.) and set to an $OD_{600}$ of 0.1 (0.095-0.105) equal to a concentration of $3\times10^8$ CFU/ml.

Serum Samples: The serum samples used were from a rabbit, hyper-immunized with a preparation of an HS23/36 CPS-$CRM_{197}$ vaccine known as CCV (described above). Pre-immunization and post-immunization serum from each rabbit was heat inactivated (HI) in a 56° C. water bath for 30 minutes to inactivate native complement and stored at −20° C.

Serum bactericidal assay: Heat inactivated (HI) pre-immunization and post-immunization serum samples were diluted in 50 μl DGV extrapolated to numerous dilutions based on the day the sample was taken. A mixture of 2700 μl DGV and 800 μl baby rabbit complement (BRC, C'; Cedarlane Laboratories, Burlington, N.C.) was made and 70 μl of this mixture was added to each well except the control wells, one which did not receive any BRC or serum and one that did not receive any serum. 20 μl of each serum dilution was then added to the sample wells. 100 μl of 1:1000 diluted *C. jejuni* 81-176 cells at an $OD_{600}$ of 0.1 were then added to each well and mixed. The plate was then incubated microaerobically, at 37° C., for 1 h. After incubation, 25 μl of each well was plated in duplicate on MHP plates. Plates were incubated microaerobically, at 37° C., for 48 h. CFUs were then counted, percentage killing was calculated, and the titer was defined.

Calculating percentage of killing: Each well was plated in duplicate and the average of those two plates was taken. For each well that contained serum, the average was divided by the average of the well that contained complement only. This number was then multiplied by 100 and given was the percentage of viability of the cells. When the viability percentage was subtracted from 100%, this yielded the percentage of killing in that well.

Serum bactericidal assay titer definition: Serum bactericidal assay antibody titers are defined as the reciprocal of the serum dilution that results in greater than 50% killing when compared to the complement control.

Figure 39:
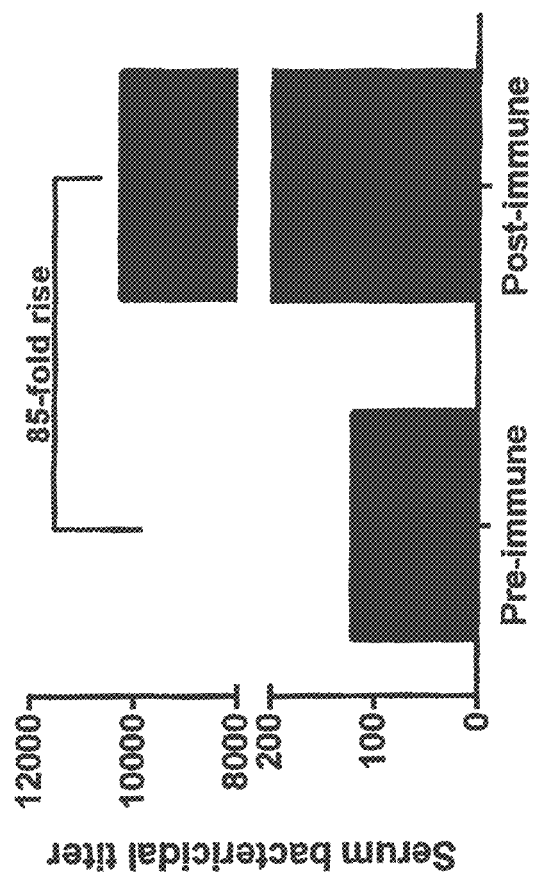
FIG. 39 depicts serum bactericidal activity in a rabbit immunized with an HS23/36 CPS-CRM$_{197}$ conjugate vaccine.

Serum bactericidal antibody activity in a rabbit immunized with an HS23/36 CPS-CRM197 conjugate vaccine: Pre-immune or post-immune sera were analyzed by serum bactericidal assay and the titers of each time point are shown as a bar graph in FIG. 39. As depicted in FIG. 39, an 85-fold rise in SBA titer between pre- and post-immune sera was observed.

Results

The serum of the rabbit prior to immunization (labeled "pre-immune" in FIG. 39) was compared to the serum following three immunizations with the vaccine ("post-immune"). There was a slight titer pre-existing in the serum prior to immunization, but there was an 85-fold increase in serum bactericidal antibody titer following administration of the vaccine.

These data demonstrate that anti-conjugate antibodies are capable of inducing serum bactericidal antibodies. The observations that MeOPN-containing epitopes are immunodominant and are capable of inducing SBA also suggests that antibodies to synthetic MeOPN-sugar epitopes, as described herein, may also induce SBA.

Having described the invention, one of skill in the art will appreciate that many modifications and variations of the present invention are possible in light of the above teachings. It is therefore, to be understood that, within the scope of the appended claims, the invention may be practiced otherwise than as specifically described.

What is claimed is:

1. An immunogenic synthetic construct capable of inducing an immune response against *Campylobacter jejuni* (*C. jejuni*) in a subject, wherein said immunogenic synthetic construct comprises one or more monosaccharides comprising one or more O-methyl phosphoramidate (MeOPN) moieties, wherein said one or more monosaccharides comprising one or more MeOPN moieties is MeOPN-4-Gal.

2. The immunogenic synthetic construct of claim 1 wherein said immunogenic synthetic construct further comprises one or more MeOPN moieties selected from the group consisting of MeOPN-2-Gal and MeOPN-6-Gal.

3. The immunogenic synthetic construct of claim 1 or claim 2 wherein said immunogenic synthetic construct is conjugated to a carrier protein.

4. The immunogenic synthetic construct of claim 3 wherein the carrier protein contains at least one T-cell epitope.

5. The immunogenic synthetic construct of claim 4 wherein the carrier protein is $CRM_{197}$.

6. The immunogenic synthetic construct of claim 1 or claim 2 wherein the subject is a human.

7. A composition comprising the immunogenic synthetic construct of claim 1 or claim 2.

8. The composition of claim 7 wherein the composition is a pharmaceutical composition.

9. The composition of claim 8 wherein said pharmaceutical composition is a vaccine formulation.

10. The composition of claim 9 wherein the vaccine formulation further comprises an immune-effective amount of one or more adjuvants.

11. The composition of claim 10 wherein the one or more adjuvants is selected from the group consisting of toll-like receptor ligands, aluminum phosphate, aluminum hydroxide, monophosphoryl lipid A, liposomes, and derivatives and combinations thereof.

12. The composition of claim 7 wherein the composition further comprises one or more additional immunoregulatory agents.

13. The composition of claim 12 wherein the one or more additional immunoregulatory agents is a substance selected from the group consisting of antigens of one or more strains of *C. jejuni*, antigens of ETEC, *Shigella* lipopolysaccharide structures, and unconjugated carrier proteins.

14. The composition of claim 7 wherein the subject is a human.

15. A method of inducing an immune response against *C. jejuni* in a subject comprising administering to the subject an effective amount of the immunogenic synthetic construct of claim 1 or claim 2.

16. The method of claim 15 wherein the subject is human.

17. A method of inducing an immune response against *C. jejuni* in a subject comprising administering to the subject an effective amount of the composition of claim 7.

18. The method of claim 17 wherein the subject is human.

19. A method of inducing an immune response against *C. jejuni* in a subject comprising administering to the subject an effective amount of the composition of claim 8.

20. The method of claim 19 wherein said subject is a human.

21. A method of inducing an immune response against *C. jejuni* in a subject, said method comprising
  (a.) administering to the subject an effective amount of the immunogenic synthetic construct of claim 1 or claim 2; and
  (b.) optionally administering to the subject one or more boosting doses of the immunogenic synthetic construct administered in step (a).

22. The method of claim 21 wherein the effective amount administered in step (a) is from about 0.1 µg to about 10 mg of the immunogenic synthetic construct.

23. The method of claim 21 wherein said method further comprises administering an immune-effective amount of one or more adjuvants with the construct in step (a) and/or step (b).

24. A method of inducing an immune response against *C. jejuni* in a subject, said method comprising
  (a). administering to the subject an effective amount of the composition of claim 8; and
  (b). optionally administering to the subject one or more boosting doses of the composition administered in step (a).

25. The method of claim 24 wherein the effective amount administered in step (a) is from about 0.1 µg to about 10 mg of the immunogenic synthetic construct.

26. The method of claim 24 wherein said method further comprises administering an immune-effective amount of one or more adjuvants with the construct in step (a) and/or step (b).

27. The method of claim 19 wherein the composition is a vaccine formulation.

28. The method of claim 24 wherein the composition is a vaccine formulation.

29. A method of treating or ameliorating a *C. jejuni* bacterial infection in a subject in need thereof comprising administering to the subject one or more doses of immunoglobulins, wherein said immunoglobulins recognize MeOPN-4-Gal and optionally recognize one or more additional MeOPN moieties, in the capsule of said *C. jejuni* bacteria.

30. The method of claim 29 wherein said one or more additional MeOPN moieties are selected from the group consisting of MeOPN-2-Gal and MeOPN-6-Gal.

31. The method of claim 29 or claim 30 wherein said subject is human.

* * * * *

SEQUENCE LISTING

```
<160> NUMBER OF SEQ ID NOS: 23

<210> SEQ ID NO 1
<211> LENGTH: 41
<212> TYPE: DNA
<213> ORGANISM: Artificial Sequence
<220> FEATURE:
<223> OTHER INFORMATION: C. Jejuni

<400> SEQUENCE: 1
ggaattcgat gattatttta tagatattgg tgtgcctgag g                41

<210> SEQ ID NO 2
<211> LENGTH: 46
<212> TYPE: DNA
<213> ORGANISM: Artificial Sequence
<220> FEATURE:
<223> OTHER INFORMATION: C. jejuni

<400> SEQUENCE: 2
ccctcgaggg gatattacta tcgactatat cgtaactatt acaacc          46

<210> SEQ ID NO 3
<211> LENGTH: 24
```

-continued

```
<212> TYPE: DNA
<213> ORGANISM: Artificial Sequence
<220> FEATURE:
<223> OTHER INFORMATION: C. jejuni

<400> SEQUENCE: 3
ccagctgaac ttgcttggga gatg                                              24

<210> SEQ ID NO 4
<211> LENGTH: 38
<212> TYPE: DNA
<213> ORGANISM: Artificial Sequence
<220> FEATURE:
<223> OTHER INFORMATION: C. jejuni

<400> SEQUENCE: 4
gggatattac tatcgactat atcgtaacta ttacaacc                               38

<210> SEQ ID NO 5
<211> LENGTH: 30
<212> TYPE: DNA
<213> ORGANISM: Artificial Sequence
<220> FEATURE:
<223> OTHER INFORMATION: C. jejuni

<400> SEQUENCE: 5
gtgtgatgtg gtggttacgt tgaattcggg                                        30

<210> SEQ ID NO 6
<211> LENGTH: 39
<212> TYPE: DNA
<213> ORGANISM: Artificial Sequence
<220> FEATURE:
<223> OTHER INFORMATION: C. jejuni

<400> SEQUENCE: 6
ctcaaatcta tagtaagtgg catgattaac atgccaagc                              39

<210> SEQ ID NO 7
<211> LENGTH: 26
<212> TYPE: DNA
<213> ORGANISM: Artificial Sequence
<220> FEATURE:
<223> OTHER INFORMATION: C. jejuni

<400> SEQUENCE: 7
catccttatc cttcattact tgatcc                                            26

<210> SEQ ID NO 8
<211> LENGTH: 27
<212> TYPE: DNA
<213> ORGANISM: Artificial Sequence
<220> FEATURE:
<223> OTHER INFORMATION: C. jejuni

<400> SEQUENCE: 8
cgtggaacat gtttatttat catatgc                                           27

<210> SEQ ID NO 9
<211> LENGTH: 28
<212> TYPE: DNA
<213> ORGANISM: Artificial Sequence
<220> FEATURE:
<223> OTHER INFORMATION: C. jejuni

<400> SEQUENCE: 9
```

```
catgaaaatc ctgagcttgg ttttgatg                                          28
```

<210> SEQ ID NO 10
<211> LENGTH: 29
<212> TYPE: DNA
<213> ORGANISM: Artificial Sequence
<220> FEATURE:
<223> OTHER INFORMATION: C. jejuni

<400> SEQUENCE: 10

```
gtattttaaa actagcttcg cataataac                                         29
```

<210> SEQ ID NO 11
<211> LENGTH: 42
<212> TYPE: DNA
<213> ORGANISM: Artificial Sequence
<220> FEATURE:
<223> OTHER INFORMATION: C. jejuni

<400> SEQUENCE: 11

```
gcgcccatgg gttaacggag cacttccatg accacctctt cc                          42
```

<210> SEQ ID NO 12
<211> LENGTH: 50
<212> TYPE: DNA
<213> ORGANISM: Artificial Sequence
<220> FEATURE:
<223> OTHER INFORMATION: C. jejuni

<400> SEQUENCE: 12

```
gcgcccatgg tctagaagat ctcctattta tgctgcttct ttgcttctgg                  50
```

<210> SEQ ID NO 13
<211> LENGTH: 42
<212> TYPE: DNA
<213> ORGANISM: Artificial Sequence
<220> FEATURE:
<223> OTHER INFORMATION: C. jejuni

<400> SEQUENCE: 13

```
cgggatccaa aggagaaacc ctatgtataa cccaaactca gc                          42
```

<210> SEQ ID NO 14
<211> LENGTH: 55
<212> TYPE: DNA
<213> ORGANISM: Artificial Sequence
<220> FEATURE:
<223> OTHER INFORMATION: C. jejuni

<400> SEQUENCE: 14

```
ggaattcgta aaatccccctt gtttcatatt gattcctttc tctaattta aacac           55
```

<210> SEQ ID NO 15
<211> LENGTH: 57
<212> TYPE: DNA
<213> ORGANISM: Artificial Sequence
<220> FEATURE:
<223> OTHER INFORMATION: C. jejuni

<400> SEQUENCE: 15

```
gctatgattg agtttacaaa caatggagga ggatatatag cattatttaa aaaactc          57
```

<210> SEQ ID NO 16
<211> LENGTH: 57
<212> TYPE: DNA
<213> ORGANISM: Artificial Sequence

```
<220> FEATURE:
<223> OTHER INFORMATION: C. jejuni

<400> SEQUENCE: 16 gagttttta aataatgcta tatatcctcc tccattgttt gtaaactcaa tcatagc      57

<210> SEQ ID NO 17
<211> LENGTH: 44
<212> TYPE: DNA
<213> ORGANISM: Artificial Sequence
<220> FEATURE:
<223> OTHER INFORMATION: C. jejuni

<400> SEQUENCE: 17
ggaattccta tattataaga taataacaca attcgcctcc tatg                   44

<210> SEQ ID NO 18
<211> LENGTH: 40
<212> TYPE: DNA
<213> ORGANISM: Artificial Sequence
<220> FEATURE:
<223> OTHER INFORMATION: C. jejuni

<400> SEQUENCE: 18
cgggatccag gagaaaccct atgtataacc caaactcagc                        40

<210> SEQ ID NO 19
<211> LENGTH: 57
<212> TYPE: DNA
<213> ORGANISM: Artificial Sequence
<220> FEATURE:
<223> OTHER INFORMATION: C. jejuni

<400> SEQUENCE: 19
gctatgattg agtttacaaa caatggagga ggatatatag cattatttaa aaaactc     57

<210> SEQ ID NO 20
<211> LENGTH: 55
<212> TYPE: DNA
<213> ORGANISM: Artificial Sequence
<220> FEATURE:
<223> OTHER INFORMATION: C. jejuni

<400> SEQUENCE: 20
agttttttaa ataatgctat atacctcctc ctttgtttgt aaactcaatc atagc       55

<210> SEQ ID NO 21
<211> LENGTH: 31
<212> TYPE: DNA
<213> ORGANISM: Artificial Sequence
<220> FEATURE:
<223> OTHER INFORMATION: C. jejuni

<400> SEQUENCE: 21
atgtataacc caaactcagc tatagaaaga g                                 31

<210> SEQ ID NO 22
<211> LENGTH: 31
<212> TYPE: DNA
<213> ORGANISM: Artificial Sequence
<220> FEATURE:
<223> OTHER INFORMATION: C. jejuni

<400> SEQUENCE: 22
gagaattgag gatactatgt ccagttaatc c                                 31
```

```
<210> SEQ ID NO 23
<211> LENGTH: 26
<212> TYPE: DNA
<213> ORGANISM: Artificial Sequence
<220> FEATURE:
<223> OTHER INFORMATION: C. jejuni

<400> SEQUENCE: 23
gctttctctc ctgttccatg gcctcc                                              26
```